(12) United States Patent
Cooper et al.

(10) Patent No.: US 12,371,463 B2
(45) Date of Patent: Jul. 29, 2025

(54) METHODS AND COMPOSITIONS FOR TREATMENT OF ANTIBIOTIC-RESISTANT BACTERIAL INFECTIONS

(71) Applicant: University of Pittsburgh—Of the Commonwealth System of Higher Education, Pittsburgh, PA (US)

(72) Inventors: Vaughn Cooper, Wexford, PA (US); Alfonso Santos López, Madrid (ES)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/724,927

(22) Filed: Apr. 20, 2022

(65) Prior Publication Data

US 2022/0332777 A1     Oct. 20, 2022

Related U.S. Application Data

(60) Provisional application No. 63/287,686, filed on Dec. 9, 2021, provisional application No. 63/177,046, filed on Apr. 20, 2021.

(51) Int. Cl.
| | |
|---|---|
| *C07K 14/47* | (2006.01) |
| *A61K 38/00* | (2006.01) |
| *A61P 31/04* | (2006.01) |
| *C12N 9/10* | (2006.01) |
| *C12N 9/12* | (2006.01) |

(52) U.S. Cl.
CPC .......... *C07K 14/4723* (2013.01); *A61P 31/04* (2018.01); *C12N 9/1007* (2013.01); *C12N 9/1048* (2013.01); *C12N 9/12* (2013.01); *A61K 38/00* (2013.01); *C12Y 207/13003* (2013.01); *C12Y 301/01061* (2013.01)

(58) Field of Classification Search
None
See application file for complete search history.

(56) References Cited

U.S. PATENT DOCUMENTS

| | | |
|---|---|---|
| 5,504,190 A | 4/1996 | Houghten et al. |
| 5,714,577 A | 2/1998 | Montelaro et al. |
| 5,945,507 A | 8/1999 | Montelaro et al. |
| 5,981,698 A | 11/1999 | Brittain |
| 6,835,713 B2 | 12/2004 | Montelaro et al. |
| 6,887,847 B2 | 5/2005 | Montelaro et al. |
| 6,974,701 B2 | 12/2005 | Bouboulis |
| 8,071,540 B2 | 12/2011 | Montelaro et al. |
| 8,357,394 B2 | 1/2013 | Flanner et al. |
| 2003/0036627 A1 | 2/2003 | Montelaro et al. |
| 2004/0043041 A1 | 3/2004 | Baker, Jr. et al. |
| 2005/0025761 A1 | 2/2005 | Thorpe et al. |
| 2005/0282239 A1 | 12/2005 | Allbritton et al. |
| 2007/0225213 A1 | 9/2007 | Kosak |
| 2009/0053278 A1 | 2/2009 | Fatora et al. |
| 2009/0099533 A1 | 4/2009 | Montelaro et al. |
| 2009/0198200 A1 | 8/2009 | Tumey et al. |
| 2010/0210506 A1 | 8/2010 | Quay et al. |
| 2013/0261534 A1 | 10/2013 | Niezgoda et al. |
| 2015/0118183 A1 | 4/2015 | Baumhof |
| 2020/0071361 A1 | 3/2020 | Steckbeck |
| 2020/0121495 A1 | 4/2020 | Nelson et al. |
| 2020/0277334 A1 | 9/2020 | Steckbeck |
| 2022/0054589 A1 | 2/2022 | Urish et al. |

FOREIGN PATENT DOCUMENTS

| | | | |
|---|---|---|---|
| EP | 0273716 B1 | 7/1988 | |
| WO | WO-02066608 A2 * | 8/2002 | ............ A01N 63/00 |
| WO | 03103718 A2 | 12/2003 | |
| WO | 2008070083 A2 | 6/2008 | |
| WO | 2010112848 A2 | 10/2010 | |
| WO | 2013169264 A1 | 11/2013 | |
| WO | 2018125746 A1 | 7/2018 | |
| WO | 2018160997 A1 | 9/2018 | |
| WO | 2018187617 A1 | 10/2018 | |
| WO | 2019178274 A1 | 9/2019 | |
| WO | 2021130390 A1 | 7/2021 | |

OTHER PUBLICATIONS

Santos-Lopez et al. (Experimental evolution to identify undescribed mechanisms 1 of resistance to a novel cationic, bioRxiv 2020.12.16.423161) (Year: 2020).*
Sanz-Garcia et al. (Front Genet. Oct. 18, 2018;9:451) (Year: 2018).*
Moskowitz et al. (Antimicrob Agents Chemother. Feb. 2012; 56(2): 1019-1030) (Year: 2012).*
Swedan et al., Synergism of cationic antimicrobial peptide WLBU2 with antibacterial agents against biofilms of multi-drug resistant Acinetobacter baumannii and Klebsiella pneumoniae, Infection and Drug Resistance, 2019, pp. 2019-2030, vol. 12, Dove Medical Press Limited.
Tam et al., Disulfide Bond Formation in Peptides by Dimethyl Sulfoxide. Scope and Applications, J. Am. Chem. Soc., 1991, pp. 6657-6662, vol. 113, American Chemical Society.
Tande et al., Clinical Presentation, Risk Factors, and Outcomes of Hematogenous Prosthetic Joint Infection in Patients with *Staphylococcus aureus* Bacteremia, 2016, The American Journal of Medicine, pp. 1-10, vol. 129, Elsevier Inc.
Tande et al., Prosthetic Joint Infection, Clinical Microbiology Reviews, 2014, pp. 302-345, vol. 27, No. 2, American Society for Microbiology.

(Continued)

*Primary Examiner* — Sergio Coffa
(74) *Attorney, Agent, or Firm* — The Webb Law Firm

(57) ABSTRACT

Provided in this disclosure are methods of treating a bacterial infection comprising administering a formulation comprising an antimicrobial peptide described herein when administered to a subject. Further provided herein are methods of treating a bacterial infection wherein the bacterial infection comprises a bacterium with a mutation in a gene resulting in antibiotic resistance.

18 Claims, 7 Drawing Sheets
(3 of 7 Drawing Sheet(s) Filed in Color)
Specification includes a Sequence Listing.

(56) References Cited

OTHER PUBLICATIONS

Tencza et al., Lentivirus-derived antimicrobial peptides: increased potency by sequence engineering and dimerization, Journal of Antimicrobial Chemotherapy, 1999, pp. 33-41, vol. 44, The British Society for Antimicrobial Chemotherapy.

Tencza et al., Calmodulin-Binding Function of LLP Segments from the HIV Type 1 Transmembrane Protein Is Conserved among Natural Sequence Variants, Aids Research and Human Retroviruses, 1997, pp. 263-269, vol. 13, No. 3, Mary Ann Liebert, Inc.

Tencza et al., Novel Antimicrobial Peptides Derived from Human Immunodeficiency Virus Type 1 and Other Lentivirus Transmembrane Proteins, Antimicrobial Agents and Chemotherapy, 1997, pp. 2394-2398, vol. 41, No. 11, American Society for Microbiology.

Tencza et al., Effect of Amino Acid Substitutions on Calmodulin Binding and Cytolytic Properties of the LLP-1 Peptide Segment of Human Immunodeficiency Virus Type 1 Transmembrane Protein, Journal of Virology, 1995, pp. 5199-5202, vol. 69, No. 8, American Society for Microbiology.

Toprak et al., Evolutionary paths to antibiotic resistance under dynamically sustained drug selection, Nature Genetics, 2012, pp. 101-106, vol. 44, No. 1, Nature America, Inc.

Trampari et al., Antibiotics select for novel pathways of resistance in biofilms, bioRxiv, 2019, pp. 1-67.

Urish et al., Antibiotic-tolerant *Staphylococcus aureus* Biofilm Persists on Arthroplasty Materials, Clin Orthop Relat Res, 2016, pp. 1649-1656, vol. 474, The Association of Bone and Joint Surgeons.

Venable et al., Theoretically Determined Three-Dimensional Structures for Amphipathic Segments of the HIV-1 gp41 Envelope Protein, AIDS Research and Human Retroviruses, 1989, pp. 7-22, vol. 5, No. 1, Mary Ann Liebert, Inc., Publishers.

Vogwill et al., Testing the Role of Genetic Background in Parallel Evolution Using the Comparative Experimental Evolution of Antibiotic Resistance, Mol. Biol. Evol., 2014, pp. 3314-3323.

Von Eiff et al., Infections Associated with Medical Devices: Pathogenesis, Management and Prophylaxis, Drugs, 2005, pp. 179-214, vol. 65, Adis Data Information BV.

Wachinger et al., Influence of amphipathic peptides on the HIV-1 production in persistently infected T lymphoma cells, 1992, pp. 235-241, vol. 309, No. 3, Elsevier Science Publishers B.V.

Wachinger et al., Antimicrobial peptides melittin and cecropin inhibit replication of human immunodeficiency virus 1 by suppressing viral gene expression, Journal of General Virology, 1998, p. 731-740, vol. 79, SGM.

Walkenhorst et al., pH Dependence of Microbe Sterilization by Cationic Antimicrobial Peptides, Antimicrobial Agents and Chemotherapy, 2013, pp. 3312-3320, vol. 57, No. 7, American Society for Microbiology.

Ward et al., Inhibition of protein kinase C by a synthetic peptide corresponding to cytoplasmic domain residues 828-848 of the human immunodeficiency virus type 1 envelope glycoprotein, Cancer Letters, 1995, pp. 37-40, vol. 88, Elsevier Science Ireland Ltd.

Wheeler et al., Intracellular delivery of HSP70 using HIV-1 Tat protein transduction domain, Biochemical and Biophysical Research Communications, 2003, pp. 54-59, vol. 301, Elsevier Science (USA).

Wild et al., A synthetic peptide inhibitor of human immunodeficiency virus replication: Correlation between solution structure and viral inhibition, Proc. Natl. Acad. Sci. USA, 1992, pp. 10537-10541, vol. 89, Medical Sciences.

Wu et al., Adsorption, structural alteration and elution of peptides at pendant PEO layers, Colloids Surf B Biointerfaces, 2013, pp. 1-18, vol. 112, Elsevier B.V.

Wu et al., Sequential and competitive adsorption of peptides at pendant PEO layers, Colloids Surf B Biointerfaces, 2015, pp. 69-76, vol. 130, Elsevier B.V.

Wu et al., Concentration effects on peptide elution from pendant PEO layers, Colloids Surf B Biointerfaces, 2014, pp. 210-217, vol. 118, Elsevier B.V.

Yang et al., Antimicrobial peptide-modified liposomes for bacteria targeted delivery of temoporfin in photodynamic antimicrobial chemotherapy, Photochem. Photobiol. Sci., 2011, pp. 1593-1601, vol. 10, The Royal Society of Chemistry and Owner Societies.

Yasin et al., Evaluation of the Inactivation of Infectious Herpes Simplex Virus by Host-Defense Peptides, Eur J Clin Micobiol Infect Dis, 2000, pp. 187-194, vol. 19, Springer-Verlag.

Yuan et al., Characterization of the Calmodulin Binding Domain of SIV Transmembrane Glycoprotein by NMR and CD Spectroscopy, Biochemistry, 1995, pp. 10690-10696, vol. 34, American Chemical Society.

Zabner et al., Adenovirus-Mediated Gene Transfer to Ciliated Airway Epithelia Requires Prolonged Incubation Time, Journal of Virology, 1996, pp. 6994-7003, vol. 70, No. 10, American Society for Microbiology.

Zanetti et al., Cathelicidins: a novel protein family with a common proregion and a variable C-terminal antimicrobial domain, FEBS Letters, 1995, pp. 1-5, vol. 374, Federation of European Biochemical Societies.

Zasloff, Antimicrobial peptides of multicellular organisms, Nature, 2002, pp. 389-395, vol. 415, Macmillan Magazines Ltd.

Zhang et al., Interactions of Bacterial Cationic Peptide Antibiotics with Outer and Cytoplasmic Membranes of Pseudomonas aeruginosa, Antimicrobial Agents and Chemotherapy, 2000, pp. 3317-3321, vol. 44, No. 12, American Society for Microbiology.

Zhang et al., Amphipathic domains in the C terminus of the transmembrane protein (gp41) permeabilize HIV-1 virions: A molecular mechanism underlying natural endogenous reverse transcription, Proc. Natl. Acad. Sci. USA, 1996, pp. 12519-12524, vol. 93, Medical Sciences.

Ziegler et al., The Cationic Cell-Penetrating Peptide CPP(TAT) Derived from the HIV-1 Protein TAT Is Rapidly Transported into Living Fibroblasts: Optical, Biophysical, and Metabolic Evidence, Biochemistry, 2005, pp. 138-148, vol. 44, American Chemical Society.

Zimmerli et al., Prosthetic-Joint Infections, The New England Journal of Medicine, 2004, pp. 1645-1654, vol. 351, Massachusetts Medical Society.

Zmistowski et al., Periprosthetic Joint Infection Increases the Risk of One-Year Mortality, J Bone Joint Surg Am, 2013, pp. 2177-2184, vol. 95, The Journal of Bone and Joint Surgery.

Abdelbaqi et al., Novel engineered cationic antimicrobial peptides display broad-spectrum activity against Francisella tularensis, Yersinia pestis and Burkholderia pseudomallei, Journal of Medical Microbiology, 2016, pp. 188-194, vol. 65, Great Britain.
Ahmed et al., Evolution of Antibiotic Resistance in Biofilm and Planktonic Pseudomonas aeruginosa Populations Exposed to Subinhibitory Levels of Ciprofloxacin, Antimicrobial Agents and Chemotherapy, 2018, pp. 1-12, vol. 62, Issue 8, American Society for Microbiology.
Arroyo et al., Membrane Permeabilization by Different Regions of the Human Immunodeficiency Virus Type 1 Transmembrane Glycoprotein gp41, Journal of Virology, 1995, pp. 4095-4102, vol. 69, No. 7, American Society for Microbiology, Madrid, Spain.
Bailey et al., The Effect of Selection Environment on the Probability of Parallel Evolution, Mol. Biol. Evol. 2015, pp. 1436-1448, vol. 32.
Barbosa et al., Evolutionary stability of collateral sensitivity to antibiotics in the model pathogen Pseudomonas aeruginosa, eLife, 2019, pp. 1-22.
Barrick et al., Identifying structural variation in haploid microbial genomes from short-read resequencing data using preseq, BMC Genomics, 2014, pp. 1-17, vol. 15.
Baym et al., Inexpensive Multiplexed Library Preparation for Megabase-Sized Genomes, PLOS ONE, 2015, pp. 1-15, vol. 10, No. 5.
Beary et al., Interruption of T-cell signal transduction by lentivirus lytic peptides from HIV-1 transmembrane protein, J. Peptide Res., 1998, pp. 75-79, vol. 51, Munksgaard.
Bell et al., The Search for 'Evolution-Proof' Antibiotics, Trends in Microbiology, 2018, pp. 471-483, vol. 26, No. 6, Elsevier Ltd.
Berge et al., Pharmaceutical Salts, Journal of Pharmaceutical Sciences, 1977, pp. 1-19, vol. 66, No. 1.

(56) References Cited

OTHER PUBLICATIONS

Beumer et al., Mass Balance Study of the Engineered Cationic Antimicrobial Peptide, WLBU2, Following a Single Intravenous Dose of 14C-WLBU2 in Mice, Current Reviews in Clinical and Experimental Pharmacology, 2021, pp. 263-272, vol. 16, Bentham Science Publishers.
Blondelle et al., Design of Model Amphipathic Peptides Having Potent Antimicrobial Activities, Biochemistry, 1992, pp. 12688-12694, vol. 31.
Bolger et al., Trimmomatic: a flexible trimmer for Illumina sequence data, Bioinformatics, 2014, pp. 2114-2120, vol. 30, No. 15, Oxford University Press.
Brockhurst et al., Assessing evolutionary risks of resistance for new antimicrobial therapies, Nature Ecology & Evolution, 2019, pp. 515-517, vol. 3.
Brown et al., Dilute Betadine Lavage Before Closure for the Prevention of Acute Postoperative Deep Periprosthetic Joint Infection, The Journal of Arthroplasty, 2012, pp. 27-30, vol. 27, No. 1, Elsevier Inc.
Brutlag et al., Improved sensitivity of biological sequence database searches, Cabios, 1990, pp. 237-245, vol. 6, No. 3, Oxford University Press.
Bucki et al., Resistance of the antibacterial agent ceragenin CSA-13 to inactivation by DNA or F-actin and its activity in cystic fibrosis sputum, Journal of Antimicrobial Chemotherapy, 2007, pp. 1-12.
Bucki et al., Salivary mucins inhibit antibacterial activity of the cathelicidin-derived LL-37 peptide but not the cationic steroid CSA-13, Journal of Antimicrobial Chemotherapy, 2008, pp. 329-335, vol. 62, Oxford University Press.
Burton et al., Antibiofilm Activity of GlmU Enzyme Inhibitors against Catheter-Associated Uropathogens, Antimicrobial Agents and Chemotherapy, 2006, pp. 1835-1840, vol. 50, No. 5, American Society for Microbiology.
Byfield et al., Cathelicidin LL-37 Increases Lung Epithelial Cell Stiffness, Decreases Transepithelial Permeability, and Prevents Epithelial Invasion by Pseudomonas aeruginosa, The Journal of Immunology, 2011, pp. 6402-6409, vol. 187, The American Association of Immunologists, Inc.
Cannatelli et al., An allelic variant of the PmrB sensor kinase reponsible for colistin resistance in an *Escherichia coli* strain of clinical origin, Scientific Reports, 2017, pp. 1-6.
Caron et al., Intracellular Delivery of a Tat-eGFP Fusion Protein into Muscle Cells, Molecular Therapy, 2001, pp. 310-318, vol. 3, No. 3, The American Society of Gene Therapy.
Chan et al., Selective Permeabilization of Gram-Negative Bacterial Membranes Using Multivalent Peptide Constructs for Antibiotic Sensitization, ACS Infectious Diseases, 2021, pp. 721-732, vol. 7, American Chemical Society.
Chen et al., Enhanced efficacy of the engineered antimicrobial peptide WLBU2 via direct airway delivery in a murine model of Pseudomonas aeruginosa pneumonia, Clinical Microbiology and Infection, 2018, pp. 547e1-547e8, vol. 24, Elsevier Ltd.
Chernomordik et al., An amphipathic Peptide from the C-Terminal Region of the Human Immunodeficiency Virus Envelope Glycoprotein Causes Pore Formation in Membranes, Journal of Virology, 1994, pp. 7115-7123, vol. 68, No. 11, American Society for Microbiology.
Chou et al., Prediction of the Secondary Structure of Proteins from their amino acid sequence, Adv Enzymol Relat Areas Mol Biol., 1978, pp. 45-148, vol. 47.
Chou et al., Prediction of Protein Conformation, Biochemistry, 1974, pp. 222-245, vol. 13, No. 2.
Cirioni et al., Pre-treatment of central venous catheters with the cathelicidin BMAP-28 enhances the efficacy of antistaphylococcal agents in the treatment of experimental catheter-related infection, Peptides, 2006, pp. 2104-2110, vol. 27, Elsevier Inc.
Comardelle et al., A Synthetic Peptide Corresponding to the Carboxy Terminus of Human Immunodeficiency Virus Type 1 Transmembrane Glycoprotein Induces Alterations in the Ionic Permeability of Xenopus laevis Oocytes, AIDS Research and Human Retroviruses, 1997, pp. 1525-1532, vol. 13, No. 17, Mary Ann Liebert, Inc.
Cooper, Experimental Evolution as a High-Throughput Screen for Genetic Adaptations, mSphere, 2018, pp. 1-7, vol. 3, issue 3.
Deatherage et al., Identification of mutations in laboratory evolved microbes from next-generation sequencing data using breseq, Methods Mol Biol., 2014, pp. 165-188, vol. 1151.
Deslouches et al., De Novo Generation of Cationic Antimicrobial Peptides: Influence of Length and Tryptophan Substitution on Antimicrobial Activity, Antimicrobial Agents and Chemotherapy, 2005, pp. 316-322, vol. 49, No. 1, American Society for Microbiology.
Deslouches et al., Comparative functional properties of engineered cationic antimicrobial peptides consisting exclusively of tryptophan and either lysine or arginine, Journal of Medical Microbiology, 2016, pp. 554-565, vol. 65, Great Britain.
Deslouches et al., De novo-derived cationic antimicrobial peptide activity in a murine model of Pseudomonas aeruginosa bacteraemia, Journal of Antimicrobial Chemotherapy, 2007, pp. 669-672, vol. 60, Oxford University Press.
Deslouches et al., Engineered Cationic Antimicrobial Peptides to Overcome Multidrug Resistance by ESKAPE Pathogens, Antimicrobial Agents and Chemotherapy, 2015, pp. 1329-1333, vol. 59, No. 2, American Society for Microbiology.
Deslouches et al., Rational Design of Engineered Cationic Antimicrobial Peptides Consisting Exclusively of Arginine and Tryptophan, and Their Activity against Multidrug-Resistant Pathogens, Antimicrobial Agents and Chemotherapy, 2013, pp. 2511-2521, vol. 57, No. 6, American Society for Microbiology.
Deslouches et al., Activity of the De Novo Engineered Antimicrobial Peptide WLBU2 against Pseudomonas aeruginosa in Human Serum and Whole Blood: Implications for Systemic Applications, Antimicrobial Agents and Chemotherapy, 2005, pp. 3208-3216, vol. 49, No. 8, American Society for Microbiology.
De Visser et al., Diminishing Returns from Mutation Supply Rate in Asexual Populations, Science, 1999, pp. 404-407, vol. 283.
Di et al., Enhanced therapeutic index of an antimicrobial peptide in mice by increasing safety and activity against multidrug-resistant bacteria, Science Advances, 2020, pp. 1-10, vol. 6.
Dietz et al., Delivery of bioactive molecules into the cell: the Trojan horse approach, Mol. Cell. Neurosci., 2004, pp. 35-131, vol. 27, Elsevier Inc.
Dillon et al., Genome-Wide Biases in the Rate and Molecular Spectrum of Spontaneous Mutations in Vibrio cholerae and Vibrio fischeri, Mol. Biol. Evol., 2016, pp. 93-109, vol. 34, Oxford University Press.
Donlan et al., Biofilms: Survival Mechanisms of Clinically Relevant Microorganisms, Clinical Microbiology Reviews, 2002, pp. 167-193, vol. 15, No. 2, American Society for Microbiology.
Eisenberg et al., Analysis of Membrane and Surface Protein Sequences with the Hydrophobic Moment Plot, J. Mol. Biol., 1984, pp. 125-142, vol. 179, Academic Press Inc (London) Ltd.
Eisenberg et al., The hydrophobic moment detects periodicity in protein hydrophobicity, Proc. Natl. Acad. Sci., 1984, pp. 140-144, vol. 81.
Eisenberg et al., The Most Highly Amphiphilic a-Helices Include Two Amino Acid Segments in Human Immunodeficiency Virus Glycoprotein 41, Biopolymers, 1990, pp. 171-177, vol. 29, John Wiley & Sons, Inc.
El-Ghannam et al., Nanoporous Delivery System to Treat Osteomyelitis and Regenerate Bone: Gentamicin Release Kinetics and Bactericidal Effect, J Biomed Mater Res Part B: Appl Biomater, 2005, pp. 277-284, vol. 73B, Wiley Periodicals, Inc.
Ellman, Tissue Sulfydryl Groups, Archives of Biochemistry and Biophysics, 1959, pp. 70-77, vol. 82.
Redefining STEM Learning, EvolvingSTEM, 2020, https://web.archive.org/web/20201125222559/https://evolvingstem.org/.
Falagas et al., Rifampicin-impregnated central venous catheters: a meta-analysis of randomized controlled trials, Journal of Antimicrobial Chemotherapy, 2007, pp. 359-369, vol. 59.
Fernandez et al., Characterization of the Polymyxin B Resistome of Pseudomonas aeruginosa, Antimicrobial Agents and Chemotherapy, 2013, pp. 110-119, vol. 57.

(56) References Cited

OTHER PUBLICATIONS

Maltas et al., Pervasive and diverse collateral sensitivity profiles inform optimal strategies to limit antibiotic resistance, PLOS Biology, 2019, pp. 1-34, vol. 17, No. 10.
Mandell et al., Elimination of Antibiotic Resistant Surgical Implant Biofilms Using an Engineered Cationic Amphipathic Peptide WLBU2, Scientific Reports, 2017, pp. 1-9, vol. 7.
Mandell et al., Direct antimicrobial activity of cationic amhipathic peptide WLBU2 against Staphylococcus aureus biofilms is enhanced in physiologic buffered saline, Journal of Orthopaedic Research, 2020, pp. 2657-2563, vol. 38, Wiley Periodicals LLC.
Mcclanahan et al., Bioactivity of WLBU2 peptide antibiotic in combination with bioerodible polymer, Int J Antimicrob Agents, 2011, pp. 530-533, vol. 38, Elsevier B.v. and the International Society of Chemotherapy.
Mehta et al., Using experimental evolution to identify druggable targets that could inhibit the evolution of antimicrobial resistance, J Antibiot (Tokyo), pp. 279-286, vol. 71.
Melvin et al., Simultaneous Antibiofilm and Antiviral Activities of an Engineered Antimicrobial Peptide during Virus-Bacterium Coinfection, mSphere, 2016, pp. 1-11, vol. 1, issue 3.
Mena et al., Genetic Adaptation of Pseudomonas aeruginosa to the Airways of Cystic Fibrosis Patients Is Catalyzed by Hypermutation, Journal of Bacteriology, 2008, pp. 7910-7917, vol. 190, No. 24, American Society for Microbiology.
Merrifield et al., Design and synthesis of antimicrobial peptides, Antimicrobial peptides, 1994, pp. 5-26, Wiley, Chichester.
Mi et al., Characterization of a Class of Cationic Peptides Able to Facilitate Efficient Protein Transduction in Vitro and in Vivo, Molecular Therapy, 2000, pp. 339-347, vol. 2, No. 4, The American Society of Gene Therapy.
Miller et al., Alterations in Cell Membrane Permeability by the Lentivirus Lytic Peptide (LLP-1) of HIV-1 Transmembrane Protein, Virology, 1993, pp. 89-100, vol. 196, Academic Press, Inc.
Miller et al., A Structural Correlation Between Lentivirus Transmembrane Proteins and Natural Cytolytic Peptides, AIDS Research and Human Retroviruses, 1991, pp. 511-519, vol. 7, No. 6, Mary Ann Liebert, Inc., Publishers.
Miller et al., Identification of a Calmodulin-Binding and Inhibitory Peptide Domain in the HIV-1 Transmembrane Glycoprotein, Aids Research and Human Retroviruses, 1993, 1057-1066, vol. 9, No. 11, Mary Ann Liebert, Inc., Publishers.
Moore et al., Preliminary Experimental Anticancer Activity of Cecropins, Peptide Research, 1994, pp. 265-269, vol. 7, No. 5.
Moran et al., The diagnosis and management of prosthetic joint infections, J Antimicrob Chemother, 2010, pp. ii45-ii54, vol. 65, Oxford University Press.
Morris et al., A peptide carrier for the delivery of biologically active proteins into mammalian cells, Nature Biotechnology, 2001, pp. 1173-1176, vol. 19, Nature Publishing Group.
Moskowitz et al., PmrB Mutations Promote Polymyxin Resistance of Pseudomonas aeruginosa Isolated from Colistin-Treated Cystic Fibrosis Patients, Antimicrobial Agents and Chemotherapy, 2011, pp. 1019-1030, American Society for Microbiology.
Novak et al., Efficacy of the De Novo-Derived Antimicrobial Peptide WLBU2 against Oral Bacteria, Antimicrobial Agents and Chemotherapy, 2007, pp. 1837-1839, vol. 51, No. 5, American Society for Microbiology.
Oliver et al., High Frequency of Hypermutable Pseudomonas aeruginosa in Cystic Fibrosis Lung Infection, Science, 2000, pp. 1251-1253, vol. 288.
Palace et al., Determination of amino acids in diverse polymeric matrices using HPLC with emphasis on agars and agaroses, Biochimica et Biophysica Acta, 1999, pp. 509-518, vol. 1472, Elsevier Science B.V.
Papkou et al., Efflux pump activity potentiates the evolution of antibiotic resistance across S. aureus isolates, Nature Communications, 2020, pp. 1-15, vol. 11.

Paranjape et al., Modulation of proinflammatory activity by the engineered cationic antimicrobial peptide WLBU-2, F1000Research, 2013, pp. 1-9.
Pearson et al., Method for Reliable Determination of Minimal Lethal Antibiotic Concentrations, Antimicrobial Agents and Chemotherapy, 1980, pp. 699-708, vol. 18, No. 5.
Perron et al., Experimental evolution of resistance to an antimicrobial peptide, Proc. R. Soc. B, 2006, pp. 251-256, vol. 273, The Royal Society.
Pettit et al., Application of a high throughput Alamar blue biofilm susceptibility assay to Satphylococcus aureus biofilms, Annals of Clinical Microbiology and Antimicrobials, 2009, pp. 1-7, vol. 8.
Phadke et al., Selective toxicity of engineered lentivirus lytic peptides in a CF airway cell model, Peptides, 2003, pp. 1099-1107, vol. 24, Elsevier Inc.
Phadke et al., Antimicrobial Peptides in Mucosal Secretions: The Importance of Local Secretions in Mitigating Infection, Symposium: Innate Immunity and Human Milk, 2005, American Society for Nutritional Sciences.
Pulido et al., Periprosthetic Joint Infection, Clin Orthop Relat Res, 2008, pp. 1710-1715, vol. 466, The Association of Bone and Joint Surgeons.
Raman et al., Enhanced capture of bacteria and endotoxin by antimicrobial WLBU2 peptide tethered on polyethylene oxide spaces, Biointerphases, 2017, pp. 1-11, vol. 12, American Vacuum Society.
Remington: The Science and Practice of Pharmacy, Chs. 37, 41-45, and 47, 21st Edition, Lippincott Williams & Wilkins.
Ribeiro et al., Heme oxygenase-1 fused to a TAT peptide transduces and protects pancreatic beta-cells, Biochemical and Biophysical Research Communications, 2003, pp. 876-881, vol. 305, Elsevier Science (USA).
Robinson et al., Integrative Genomics Viewer, Nat Biotechnol, 2011, pp. 24-26, vol. 29.
Robinson Jr et al., Anti-HIV-1 activity of indolicidin, an antimicrobial peptide from neutrophils, Journal of Leukocyte Biology, 1998, pp. 94-100, vol. 63.
Rocchetta et al., Genetics of O-Antigen Biosynthesis in Pseudomonas aeruginosa, Microbiology and Molecular Biology Reviews, 1999, pp. 523-553, vol. 63, No. 3, American Society for Microbiology.
Ruder et al., Treatment of Periprosthetic Joint Infection Using Antimicrobials: Dilute Povidone-Iodine Lavage, J. Bone Joint Infect., 2017, pp. 10-14, vol. 2, Ivyspring International Publisher.
Rushlow et al., Lentivirus Genomic Organization: The Complete Nucleotide Sequence of the env Gene Region of Equine Infectious Anemia Virus, Virology, 1986, pp. 309-321, vol. 155, American Press.
Ryder et al., Binding Interactions of Bacterial Lipopolysaccharide and the Cationic Amphiphilic Peptides Polymyxin B and WLBU2, Colloids Surf B Biointerfaces, 2014, pp. 81-87, vol. 120, Elsevier B.V.
Santajit et al., Mechanisms of Antimicrobial Resistance in ESKAPE pathogens, BioMed Research International, 2016, pp. 1-8, Hindawi Publishing Corporation.
Santos-Lopez et al., Experimental evolution to identify undescribed mechanisms of resistance to a novel cationic peptide antibiotic, bioRxiv, 2020, pp. 1-21.
Santos-Lopez et al., Evolutionary pathways to antibiotic resistance are dependent upon environmental structure and bacterial lifestyle, eLife, 2019, pp. 1-23.
Santos-Lopez et al., Experimental evolution to identify undescribed mechanisms of resistance to a novel cationic peptide antibiotic, bioRxiv, 2021, pp. 1-26.
Sarin et al., Quantitative Monitoring of Solid-Phase Peptide Synthesis by the Ninhydrin Reaction, Analytical Biochemistry, 1981, pp. 147-157, vol. 117, Academic Press, Inc.
Scott et al. Biological Properties of Structurally Related alpha-Helical Cationic Antimicrobial Peptides, Infection and Immunity, 1999, pp. 2005-2009, vol. 67, No. 4, American Society for Microbiology.
Scribner et al., Parallel Evolution of Tobramycin Resistance across Species and Environments, mBio, 2020, pp. 1-17, vol. 11, issue 3.

(56) References Cited

OTHER PUBLICATIONS

Shaver et al., Fitness Evolution and the Rise of Mutator Alleles in Experimental *Escherichia coli* Populations, Genetics, 2002, pp. 557-566, vol. 162, Genetics Society of America.
Shen et al., Evaluation of Peptide-Mediated Transduction in Human CD34+ Cells, Human Gene Therapy, 2004, pp. 415-419, vol. 15, Mary Ann Liebert, Inc.
Skinner et al., Evaluation of WLBU2 Peptide and 3-O-Octyl-sn-Glycerol Lipid as Active Ingredients for a Topical Microbicide Formulation Targeting Chlamydia trachomatis, Antimicrobial Agents and Chemotherapy, 2010, pp. 627-636, vol. 54, No. 2, American Society for Microbiology.
Spohn et al., Integrated evolutionary analysis reveals antimicrobial peptides with limited resistance, Nature Communications, 2019, pp. 1-13.
Srinivas et al., Calmodulin Antagonists Inhibit Human Immunodeficiency Virus-Induced Cell Fusion but Not Virus Replication, AIDS Research and Human Retroviruses, 1994, pp. 1489-1496, vol. 10, No. 11.
Srinivas et al., Cytosolic Domain of the Human Immunodeficiency Virus Envelope Glycoproteins Binds to Calmodulin and Inhibits Calmodulin-regulated Proteins, The Journal of Biological Chemistry, 1993, pp. 22895-22899, vol. 268, No. 30, The American Society for Biochemistry and Molecular Biology, Inc.
Starkey et al., Pseudomonas aeruginosa Rugose Small-Colony Variants Have Adaptations That Likely Promote Persistence in the Cystic Fibrosis Lung, Journal of Bacteriology, 2009, pp. 3492-3503, vol. 191, No. 11, American Society for Microbiology.
File, Overview of Resistance in the 1990s, Chest, 1999, pp. 3S-8S, vol. 115, American College of Chest Physicians.
Flynn et al., Evolution of Ecological Diversity in Biofilms of Pseudomonas aeruginosa by Altered Cyclic Diguanylate Signaling, Journal of Bacteriology, 2016, pp. 2608-2618, vol. 198, No. 19.
Fontenot et al., A Survey of Potential Problems and Quality Control in Peptide Synthesis by the Fluorenylmethoxycarbonyl Procedure, Peptide Research, 1991, pp. 19-25, vol. 4, No. 1.
Friedrich et al., Salt-Resistant Alpha-Helical Cationic Antimicrobial Peptides, Antimicrobial Agents and Chemotherapy, 1999, pp. 1542-1548, vol. 43, No. 7, American Society for Microbiology.
Frisch et al., Intraoperative chlorhexidine irrigation to prevent infection in total hip and knee arthroplasty, Arthroplasty Today, 2017, pp. 294-297, vol. 3, Elsevier Inc.
Fujii et al., A molecular model for membrane fusion based on solution studies of an amphiphilic peptide from HIV gp41, Protein Science, 1992, pp. 1454-1464, The Protein Society.
Fux et al., Survival strategies of infectious biofilms, Trends in Microbiology, 2005, pp. 34-40, vol. 13, No. 1, Elsevier td.
Ganz et al., Antimicrobial peptides of leukocytes, Current Opinion in Hematology 1997, pp. 53-58, vol. 4, Rapid Science Publishers.
Garnier et al., Analysis of the Accuracy and Implications of Simple Methods for Predicting the Secondary Structure of Globular Proteins, J. Mol. Biol., 1978, pp. 97-120, vol. 120, Academic Press Inc. (London) Ltd.
Gawrisch et al., Interaction of Peptide Fragment 828-848 of the Envelope Glycoprotein of Human Immunodeficiency Virus Type I with Lipid Bilayers, Biochemistry, 1993, pp. 3112-3118, vol. 32, American Chemical Society.
George et al., Use of Chlorhexidine Preparations in Total Joint Arthroplasty, J. Bone Joint Infect., 2017, pp. 15-22, vol. 2, Ivyspring International Publisher.
Gifford et al., Mutators drive evolution of multi-resistance to antibiotics, bioRxiv, 2021, pp. 1-36.
Gloag et al., Pseudomonas aeruginosa Interstrain Dynamics and Selection of Hyperbiofilm Mutatnts during a Chronic Infection, mBio (ASM Journals), 2019, pp. 1-16, vol. 10, issue 4.
Golbek et al., Identifying the selectivity of antimicrobial peptides to cell membranes by sum frequency generation spectroscopy, Biointerphases, 2017, pp. 1-10, vol. 12, American Vacuum Society.

Guelen et al., TAT-apoptin is efficiently delivered and induces apoptosis in cancer cells, Oncogene, 2004, pp. 1153-1165, vol. 23, Nature Publishing Group.
Gullberg et al., Selection of Resistant Bacteria at Very Low Antibiotic Concentrations, PLOS Pathogens, 2011, pp. 1-9, vol. 7, issue 7.
Ha et al., c-di-GMP and its effects on biofilm formation and dispersion: a Pseudomonas aeruginosa review, Microbiol Spectr., 2015, pp. 1-20, vol. 3, issue 2.
Habermann, Bee and Wasp Venoms, Science, 1972, pp. 314-322, vol. 177, No. 4046, American Association for the Advancement of Science.
Hancock, Host Defence (Cationic) Peptides: What is Their Future Clinical Potential?, Drugs, 1999, pp. 469-473, vol. 57, issue 4, Adis International Limited.
Handbook of Pharmaceutical Excipients, Pharmaceutical Press, 2006, pp. 1-945, Fifth Edition, Pharmaceutical Press and the American Pharmacists Association.
Harris et al., Polygenic Adaption and Clonal Interference Enabled Sustained Diversity in Experimental Pseudomonas aeruginosa Populations, Mol. Biol. Evol., 2021, pp. 5359-5375, vol. 38, issue 12, Oxford University Press.
Heinrich et al., Synergistic Biophysical Techniques Reveal Structural Mechanisms of Engineered Cationic Antimicrobial Peptides in Lipid Model Membranes, Chemistry, 2020, pp. 6247-6256, vol. 26, issue 28.
Hernando-Amado et al., Antibiotic Resistance Evolution Is Contingent on the Quorum-Sensing Response in Pseudomonas aeruginosa, Mol. Biol. Evol., 2019, pp. 2238-2251, vol. 36, issue 10.
Hickman et al., A chemosensory system that regulates biofilm formation through modulation of cyclic diguanylate levels, PNAS, 2005, pp. 14422-14427, vol. 102, No. 40, The National Academy of Sciences of the USA.
Honig, Protein Folding: From the Levinthal Paradox to Structure Prediction, J. Mol. Biol., 1999, pp. 283-293, vol. 293, Academic Press.
Huangyutitham et al., Subcellular Clustering of the Phosphorylated WspR Response Regulator Protein Stimulates Its Diguanylate Cyclase Activity, mBio, 2013, pp. 1-8, vol. 4, issue 3.
Hughes et al., Evolutionary Trajectories to Antibiotic Resistance, Annual Review of Microbiology, 2017, pp. 579-596, vol. 71, Annual Reviews.
Hwang et al., Structure-function relationships of antimicrobial peptides, Biochem. Cell Biol., 1998, pp. 235-246, vol. 76, NRC Canada.
Ibacache-Quiroga et al., Parallel Evolution of High-Level Aminoglycoside Resistance in *Escherichia coli* Under Low and High Mutation Supply Rates, Frontiers in Microbiology, 2018, pp. 1-14, vol. 9.
Isaacs et al., Inactivation of Herpes Simplex Virus Clinical Isolates by Using a Combination Microbicide, Antimicrobial Agents and Chemotherapy, 2006, pp. 1063-1066, vol. 50, No. 3, American Society for Microbiology.
Jennings et al., Pel is a cationic exopolysaccharide that cross-links extracellular DNA in the Pseudomonas aeruginosa biofilm matrix, PNAS, 2015, pp. 11353-11358, vol. 112, No. 36.
Kalia et al., Rational Site-Directed Mutations of the LLP-1 and LLP-2 Lentivirus Lytic Peptide Domains in the Intracytoplasmic Tail of Human Immunodeficiency Virus Type 1 gp41 Indicate Common Functions in Cell-Cell Fusion but Distinct Roles in Virion Envelope Incorporation, Journal of Virology, 2003, pp. 3634-3646, vol. 77, No. 6, American Society for Microbiology.
Klevens et al., Estimating Health Care-Associated Infections and Deaths in U.S. Hospitals, 2002, Public Health Reports, 2007, pp. 160-166, vol. 122.
Koenig et al., Effect of the conformation of a peptide from gp41 on binding and domain formation in model membranes, Molecular Membrane Biology, 1995, pp. 77-82, vol. 12, Taylor & Francis.
Kumagai et al., Elastic behavior of model membranes with antimicrobial peptides depends on lipid specificity and D-enantiomers, Soft Matter, 2019, pp. 1860-1868, vol. 15, No. 8.
Labruere et al., Anti-Methicillin-Resistant *Staphylococcus aureus* Nanoantibiotics, Frontiers in Pharmacology, 2019, pp. 1-24, vol. 10.

(56) References Cited

OTHER PUBLICATIONS

Lampi et al., Structural attributes affecting peptide entrapment in PEO brush layers, Colloids Surf B Biointerfaces, 2013, pp. 79-85, vol. 106, Elsevier B.V.

Lashua et al., Engineered cationic antimicrobial peptide (eCAP) prevents Pseudomonas aeruginosa biofilm growth on airway epithelial cells, Journal Antimicrobial Chemotherapy, 2016, pp. 2200-2207, vol. 71, Oxford University Press.

Lehrer et al., Antibacterial Activity of Microbicidal Cationic Proteins 1 and 2, Natural Peptide Antibiotics of Rabbit ung Macrophages, Infection and Immunity, 1983, pp. 10-14, vol. 42, No. 1, American Society for Microbiology.

Leszczynska et al., Bactericidal activities of the cationic steroid CSA-13 and the cathelicidin peptide LL-37 against Helicobacter pylori in simulated gastric juice, BMC Microbiology, 2009, pp. 1-10, vol. 9, BioMed Central Ltd.

Li et al., Structural insights into YfiR sequestering by YfiB in Pseudomonas aeruginosa PAO1, Scientific Reports, 2015, pp. 1-14, vol. 5.

Li et al., Antibiofilm peptides as a promising strategy: comparative research, Applied Microbiology and Biotechnology, 2021, pp. 1647-1656, vol. 105, Springer.

Lieberman et al., Parallel bacterial evolution within multiple patients identifies candidate pathogenicity genes, Nature Genetics, 2011, pp. 1275-1281, vol. 43, No. 12, Nature America, Inc.

Lin et al., Prevention of ESKAPE pathogen biofilm formation by antimicrobial peptides WLBU2 and LL37, Int J Antimicrob Agents, 2018, pp. 667-672, vol. 52, issue 5.

Ling et al., A new antibiotic kills pathogens without detectable resistance, Nature, 2015, pp. 455-459, vol. 517.

Macia et al., Hypermutation Is a Key Factor in Development of Multiple-Antimicrobial Resistance in Pseudomonas aeruginosa Strains Causing Chronic Lung Infections, Antimicrobial Agents and Chemotherapy, 2005, pp. 3382-3386, vol. 49, No. 8, American Society for Microbiology.

Maclean, Assessing the Potenial for *Staphylococcus aureus* to Evolve Resistance to XF-73, Trends in Microbiology, 2020, pp. 432-435, vol. 28, No. 6.

Maclean et al., The evolution of antibiotic resistance, Science, 2019, pp. 1082-1083, vol. 365, issue 6458, AAAS.

Mai et al., Efficiency of Protein Transduction Is Cell Type-dependent and Is Enhanced by Dextran Sulfate, The Journal of Biological Chemistry, 2002, pp. 30208-30218, vol. 277, No. 33, The American Society for Biochemistry and Molecular Biology, Inc.

Malik et al., pH Dependent Antimicrobial Peptides and Proteins, Their Mechanisms of Action and Potential as Therapeutic Agents, Pharmaceuticals, 2016, pp. 1-35, vol. 9, No. 67.

Gagne, "Osmolarity." ScienceDirect, 2014, Section 2.1.6.

Lashua et al., "Engineered cationic antimicrobial peptide (eCAP) prevents Pseudomonas aeruginosa biofilm growth on airway epithelial cells", Journal of Antimicrobial Chemotherapy, 2016, pp. 2200-2207, vol. 71.

Sanz-Garcia et al., "Mutational Evolution of Pseudomonas aeruginosa Resistance to Ribosome-Targeting Antibiotics", frontiers in Genetics, 2018, pp. 1-13, vol. 9, Article 451.

* cited by examiner

|  | WT | Population 1 | | | Population 2 | |
|---|---|---|---|---|---|---|
|  | PA14 | Smooth | Wrinkly | | Smooth | Wrinkly |
| Mutations | | | | | | |
| LPS Modification | --- | pmrB P169L | pmrB P169L | | pmrB G184D | pmrB G184D |
| O-antigen | --- | orfN +G | wbpA +1bp | | orfN -G | orfN -G |
| Biofilm | --- | yfiR L20Q | wspF S159L | | --- | wspA -42bp |
| Additional | --- | PA14_67780 G237R | --- | | --- | --- |
| Colony morphologies | | | | | | |
| on Tryptic soy agar | | | | | | |
| on Morphological agar | | | | | | |

FIG. 5

| Annotation | Position | Mutation | | Population 1 Clone | | | Population 2 Clone | | | Freq(%) |
|---|---|---|---|---|---|---|---|---|---|---|
| | | | | WP | Sm | Wr | WP | Sm | Sc | |
| pmrB | 5,637,189 | C→T | P169L(CCG→CTG) | | | | | | | 100% |
| | 5,637,234 | G→A | G184D(GGC→GAC) | | | | | | | 50% |
| orfN | 2,040,286 | ΔG | coding(138/1017) | | | | | | | 0% |
| wbpM | 2,043,187 | Δ1bp | coding(1578/1998) | | | | | | | |
| wspA | 1,406,497 | Δ42bp | coding(853-894) | | | | | | | |
| wspF | 1,412,518 | C→T | S159L(TCG→TTG) | | | | | | | |
| PA14_05600/sahH | 497,428 | A→C | intergenic(-12/+29) | | | | | | | |
| trbL | 2,681,721 | G→A | V354V(GTC→GTT) | | | | | | | |
| PA14_37360 | 3,325,906 | A→C | L41V(TTG→GTG) | | | | | | | |
| yfiR | 4,434,917 | T→A | L20Q(CTG→CAG) | | | | | | | |
| PA14_67780 | 6,052,866 | G→A | G237R(GGG→AGG) | | | | | | | |

FIG. 7

SEQUENCE LISTING

```
<160> NUMBER OF SEQ ID NOS: 31

<210> SEQ ID NO 1
<211> LENGTH: 24
<212> TYPE: PRT
<213> ORGANISM: Artificial Sequence
<220> FEATURE:
<223> OTHER INFORMATION: WLBU2 antimicrobial peptide

<400> SEQUENCE: 1

Arg Arg Trp Val Arg Arg Val Arg Arg Val Trp Arg Arg Val Val Arg
1               5                   10                  15

Val Val Arg Arg Trp Val Arg Arg
            20

<210> SEQ ID NO 2
<211> LENGTH: 14
<212> TYPE: PRT
<213> ORGANISM: Artificial Sequence
<220> FEATURE:
<223> OTHER INFORMATION: antimicrobial peptide

<400> SEQUENCE: 2

Ile Arg Arg Arg Arg Arg Arg Ile Arg Arg Arg Arg Arg Arg
1               5                   10

<210> SEQ ID NO 3
<211> LENGTH: 21
<212> TYPE: PRT
<213> ORGANISM: Artificial Sequence
```

```
<220> FEATURE:
<223> OTHER INFORMATION: antimicrobial peptide

<400> SEQUENCE: 3

Ile Arg Arg Arg Ile Arg Arg Ile Arg Arg Ile Arg Arg Ile Arg
1               5                   10                  15

Arg Arg Ile Arg Arg
            20

<210> SEQ ID NO 4
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 4

Ile Arg Arg Ile Ile Arg Arg Ile Arg Arg Ile Ile Arg Arg Ile Arg
1               5                   10                  15

Arg Ile Ile Arg Arg
            20

<210> SEQ ID NO 5
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 5

Val Trp Arg Trp Val Arg Arg Val Trp Arg Trp Val Arg Val Trp
1               5                   10                  15

Arg Trp Val Arg Arg
            20

<210> SEQ ID NO 6
<211> LENGTH: 14
<212> TYPE: PRT
<213> ORGANISM: Artificial Sequence
<220> FEATURE:
<223> OTHER INFORMATION: antimicrobial peptide

<400> SEQUENCE: 6

Val Trp Arg Trp Val Arg Arg Val Trp Arg Trp Val Arg Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: antimicrobial peptide

<400> SEQUENCE: 7

Val Val Arg Val Val Arg Arg Val Val Arg Val Val Arg Arg
1               5                   10

<210> SEQ ID NO 8
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 8
```

```
Val Val Arg Val Arg Val Val Arg Val Val
1               5                  10                 15

Arg Val Val Arg Val
            20

<210> SEQ ID NO 9
<211> LENGTH: 11
<212> TYPE: PRT
<213> ORGANISM: Artificial Sequence
<220> FEATURE:
<223> OTHER INFORMATION: antimicrobial peptide

<400> SEQUENCE: 9

Arg Ser Arg Val Val Arg Ser Trp Ser Arg Val
1               5                  10

<210> SEQ ID NO 10
<211> LENGTH: 84
<212> TYPE: PRT
<213> ORGANISM: Artificial Sequence
<220> FEATURE:
<223> OTHER INFORMATION: antimicrobial peptide

<400> SEQUENCE: 10

Arg Phe Val Arg Arg Val Arg Arg Phe Val Arg Arg Val Arg Arg Phe
1               5                  10                 15

Val Arg Arg Val Arg Arg Phe Val Arg Arg Val Arg Arg Phe Val Arg
            20                  25                  30

Arg Val Arg Arg Phe Val Arg Arg Val Arg Arg Phe Val Arg Arg Val
        35                  40                  45

Arg Arg Phe Val Arg Arg Val Arg Arg Phe Val Arg Arg Val Arg Arg
    50                  55                  60

Phe Val Arg Arg Val Arg Arg Phe Val Arg Arg Val Arg Arg Phe Val
65                  70                  75                  80

Arg Arg Val Arg

<210> SEQ ID NO 11
<211> LENGTH: 20
<212> TYPE: PRT
<213> ORGANISM: Artificial Sequence
<220> FEATURE:
<223> OTHER INFORMATION: antimicrobial peptide

<400> SEQUENCE: 11

Arg Arg Thr Tyr Ser Arg Ser Arg Arg Thr Tyr Ser Arg Ser Arg Arg
1               5                  10                 15

Thr Tyr Ser Arg
            20

<210> SEQ ID NO 12
<211> LENGTH: 28
<212> TYPE: PRT
<213> ORGANISM: Artificial Sequence
<220> FEATURE:
<223> OTHER INFORMATION: antimicrobial peptide

<400> SEQUENCE: 12

Lys Val Val Ser Ser Ile Ile Glu Ile Ile Ser Ser Val Val Lys Val
1               5                  10                 15

Val Ser Ser Ile Ile Glu Ile Ile Ser Ser Val Val
            20                  25
```

```
<210> SEQ ID NO 13
<211> LENGTH: 20
<212> TYPE: PRT
<213> ORGANISM: Artificial Sequence
<220> FEATURE:
<223> OTHER INFORMATION: antimicrobial peptide

<400> SEQUENCE: 13

Lys Lys Thr His Thr Lys Thr Lys Thr His Thr Lys Thr Lys Lys
1               5                   10                  15

Thr His Thr Lys
            20

<210> SEQ ID NO 14
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 14

Val Val Arg Val Val Arg Arg Val Val Arg Val Val Arg Arg Val Val
1               5                   10                  15

Arg Val Val Arg Arg
            20

<210> SEQ ID NO 15
<211> LENGTH: 12
<212> TYPE: PRT
<213> ORGANISM: Artificial Sequence
<220> FEATURE:
<223> OTHER INFORMATION: antimicrobial peptide

<400> SEQUENCE: 15

Arg Val Val Arg Val Val Arg Arg Val Val Arg Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: antimicrobial peptide

<400> SEQUENCE: 16

Arg Val Val Arg Val Val Arg Arg Trp Val Arg Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: antimicrobial peptide

<400> SEQUENCE: 17

Arg Trp Trp Arg Trp Trp Arg Arg Trp Trp Arg Arg
1               5                   10

<210> SEQ ID NO 18
<211> LENGTH: 18
<212> TYPE: PRT
<213> ORGANISM: Artificial Sequence
<220> FEATURE:
<223> OTHER INFORMATION: antimicrobial peptide

<400> SEQUENCE: 18
```

Trp Arg Arg Trp Trp Arg Arg Trp Trp Arg Trp Trp Arg Arg Trp Trp
1               5                   10                  15

Arg Arg

<210> SEQ ID NO 19
<211> LENGTH: 24
<212> TYPE: PRT
<213> ORGANISM: Artificial Sequence
<220> FEATURE:
<223> OTHER INFORMATION: antimicrobial peptide

<400> SEQUENCE: 19

Arg Arg Val Val Arg Arg Val Arg Val Val Arg Val Arg Val Val Arg
1               5                   10                  15

Val Val Arg Arg Val Val Arg Arg
            20

<210> SEQ ID NO 20
<211> LENGTH: 24
<212> TYPE: PRT
<213> ORGANISM: Artificial Sequence
<220> FEATURE:
<223> OTHER INFORMATION: antimicrobial peptide

<400> SEQUENCE: 20

Arg Arg Trp Trp Arg Arg Trp Arg Arg Trp Trp Arg Arg Trp Trp Arg
1               5                   10                  15

Trp Trp Arg Arg Trp Trp Arg Arg
            20

<210> SEQ ID NO 21
<211> LENGTH: 36
<212> TYPE: PRT
<213> ORGANISM: Artificial Sequence
<220> FEATURE:
<223> OTHER INFORMATION: antimicrobial peptide

<400> SEQUENCE: 21

Val Arg Arg Val Val Arg Arg Val Val Arg Val Val Arg Arg Val Val
1               5                   10                  15

Arg Arg Val Arg Arg Val Val Arg Arg Val Val Arg Val Val Arg Arg
            20                  25                  30

Val Val Arg Arg
        35

<210> SEQ ID NO 22
<211> LENGTH: 36
<212> TYPE: PRT
<213> ORGANISM: Artificial Sequence
<220> FEATURE:
<223> OTHER INFORMATION: antimicrobial peptide

<400> SEQUENCE: 22

Val Arg Arg Val Trp Arg Arg Val Val Arg Val Val Arg Arg Trp Val
1               5                   10                  15

Arg Arg Val Arg Arg Val Trp Arg Arg Val Val Arg Val Val Arg Arg
            20                  25                  30

Trp Val Arg Arg
        35

<210> SEQ ID NO 23
<211> LENGTH: 42

```
<212> TYPE: PRT
<213> ORGANISM: Artificial Sequence
<220> FEATURE:
<223> OTHER INFORMATION: antimicrobial peptide

<400> SEQUENCE: 23

Arg Arg Val Val Arg Val Arg Val Val Arg Arg Val Val Arg
1               5                   10                  15

Val Val Arg Arg Val Val Arg Val Arg Arg Val Val Arg Arg Val
            20                  25                  30

Val Arg Val Val Arg Arg Val Val Arg Arg
        35                  40

<210> SEQ ID NO 24
<211> LENGTH: 48
<212> TYPE: PRT
<213> ORGANISM: Artificial Sequence
<220> FEATURE:
<223> OTHER INFORMATION: antimicrobial peptide

<400> SEQUENCE: 24

Arg Val Val Arg Val Val Arg Arg Val Val Arg Arg Val Arg Arg Val
1               5                   10                  15

Val Arg Arg Val Val Arg Val Val Arg Arg Val Val Arg Arg Val Arg
            20                  25                  30

Arg Val Val Arg Arg Val Val Arg Val Val Arg Arg Val Val Arg Arg
        35                  40                  45

<210> SEQ ID NO 25
<211> LENGTH: 48
<212> TYPE: PRT
<213> ORGANISM: Artificial Sequence
<220> FEATURE:
<223> OTHER INFORMATION: antimicrobial peptide

<400> SEQUENCE: 25

Arg Val Val Arg Val Val Arg Arg Trp Val Arg Arg Val Arg Arg Val
1               5                   10                  15

Trp Arg Arg Val Val Arg Val Val Arg Arg Trp Val Arg Arg Val Arg
            20                  25                  30

Arg Val Trp Arg Arg Val Val Arg Val Val Arg Arg Trp Arg Val Val
        35                  40                  45

<210> SEQ ID NO 26
<211> LENGTH: 363
<212> TYPE: PRT
<213> ORGANISM: Escherichia coli

<400> SEQUENCE: 26

Met His Phe Leu Arg Arg Pro Ile Ser Leu Arg Gln Arg Leu Ile Leu
1               5                   10                  15

Thr Ile Gly Ala Ile Leu Leu Val Phe Glu Leu Ile Ser Val Phe Trp
            20                  25                  30

Leu Trp His Glu Ser Thr Glu Gln Ile Gln Leu Phe Glu Gln Ala Leu
        35                  40                  45

Arg Asp Asn Arg Asn Asn Asp Arg His Ile Ile Arg Glu Ile Arg Glu
    50                  55                  60

Ala Val Ala Ser Leu Ile Val Pro Gly Val Phe Met Val Ser Leu Thr
65                  70                  75                  80

Leu Phe Ile Cys Tyr Gln Ala Val Arg Arg Ile Thr Arg Pro Leu Ala
                85                  90                  95
```

Glu Leu Gln Lys Glu Leu Glu Ala Arg Thr Ala Asp Asn Leu Thr Pro
            100                 105                 110

Ile Ala Ile His Ser Ala Thr Leu Glu Ile Glu Ala Val Val Ser Ala
            115                 120                 125

Leu Asn Asp Leu Val Ser Arg Leu Thr Ser Thr Leu Asp Asn Glu Arg
        130                 135                 140

Leu Phe Thr Ala Asp Val Ala His Glu Leu Arg Thr Pro Leu Ala Gly
145                 150                 155                 160

Val Arg Leu His Leu Glu Leu Ala Lys Thr His His Ile Asp Val
            165                 170                 175

Ala Pro Leu Val Ala Arg Leu Asp Gln Met Met Glu Ser Val Ser Gln
            180                 185                 190

Leu Leu Gln Leu Ala Arg Ala Gly Gln Ser Phe Ser Ser Gly Asn Tyr
            195                 200                 205

Gln His Val Lys Leu Leu Glu Asp Val Ile Leu Pro Ser Tyr Asp Glu
            210                 215                 220

Leu Ser Thr Met Leu Asp Gln Arg Gln Gln Thr Leu Leu Pro Glu
225                 230                 235                 240

Ser Ala Ala Asp Ile Thr Val Gln Gly Asp Ala Thr Leu Leu Arg Met
            245                 250                 255

Leu Leu Arg Asn Leu Val Glu Asn Ala His Arg Tyr Ser Pro Gln Gly
            260                 265                 270

Ser Asn Ile Met Ile Lys Leu Gln Glu Asp Asp Gly Ala Val Met Ala
            275                 280                 285

Val Glu Asp Glu Gly Pro Gly Ile Asp Glu Ser Lys Cys Gly Glu Leu
            290                 295                 300

Ser Lys Ala Phe Val Arg Met Asp Ser Arg Tyr Gly Gly Ile Gly Leu
305                 310                 315                 320

Gly Leu Ser Ile Val Ser Arg Ile Thr Gln Leu His His Gly Gln Phe
            325                 330                 335

Phe Leu Gln Asn Arg Gln Glu Thr Ser Gly Thr Arg Ala Trp Val Arg
            340                 345                 350

Leu Lys Lys Asp Gln Tyr Val Ala Asn Gln Ile
            355                 360

<210> SEQ ID NO 27
<211> LENGTH: 346
<212> TYPE: PRT
<213> ORGANISM: Pseudomonas aeruginosa

<400> SEQUENCE: 27

Met Met Asn Leu Trp Leu Leu Leu Pro Ala Val Ala Ala Leu Ser Leu
1               5                   10                  15

Leu Leu Thr Ala Gly Leu Arg Arg Tyr Ala Ile Ala Arg Ser Leu Ile
            20                  25                  30

Asp Val Pro Asn Ala Arg Ser Ser His Gln Val Pro Thr Pro Thr Gly
            35                  40                  45

Gly Gly Val Ala Ile Val Leu Ser Phe Leu Leu Ala Val Leu Leu Ala
        50                  55                  60

Ala Ile Leu Gly Ala Val Lys Pro Asp Leu Ala Thr Gly Ile Leu Gly
65                  70                  75                  80

Ala Gly Ile Gly Ile Ala Leu Leu Gly Phe Leu Asp Asp His Gly His
            85                  90                  95

Ile Ala Ala Arg Trp Arg Leu Leu Gly His Phe Ala Gly Ala Cys Trp

```
            100                 105                 110
Leu Leu Tyr Trp Leu Gly Gly Leu Pro Ala Leu Ala Phe Phe Gly Leu
            115                 120                 125

Val Val Asp Leu Gly Trp Val Gly His Ile Ala Ala Ala Phe Tyr Leu
            130                 135                 140

Val Trp Met Leu Asn Leu Tyr Asn Phe Met Asp Gly Ile Asp Gly Ile
145                 150                 155                 160

Ala Ser Val Glu Ala Val Cys Val Cys Val Gly Ala Ala Leu Leu Val
            165                 170                 175

Val Val Ser Gly Val Gly Ser Asp Glu Ala Ser Gln Gly Val Trp Leu
            180                 185                 190

Ala Ala Leu Leu Ala Ala Ala Val Thr Gly Phe Leu Phe Trp Asn Phe
            195                 200                 205

Pro Pro Ala Arg Ile Phe Met Gly Asp Ala Gly Ser Gly Phe Leu Gly
            210                 215                 220

Val Ile Ile Gly Gly Leu Ser Leu Gln Ala Ala Trp Val Ser Pro Gln
225                 230                 235                 240

Leu Phe Trp Gly Trp Leu Ile Leu Leu Gly Val Phe Ile Val Asp Ala
            245                 250                 255

Thr Leu Thr Leu Leu Arg Arg Leu Leu Arg Gly Asp Lys Val Tyr Glu
            260                 265                 270

Ala His Arg Ser His Ala Tyr Gln Tyr Ala Ser Arg His Tyr Gly Arg
            275                 280                 285

His Leu Pro Val Thr Leu Ala Val Gly Gly Ile Asn Ile Phe Trp Leu
            290                 295                 300

Leu Pro Leu Ala Leu Leu Val Ala Ala Gly Lys Ile Asp Gly Met Leu
305                 310                 315                 320

Ala Leu Leu Ile Gly Tyr Leu Pro Leu Ala Phe Leu Ala Leu Arg Phe
            325                 330                 335

Lys Ala Gly Val Leu Glu Ser Arg Ala Ala
            340                 345

<210> SEQ ID NO 28
<211> LENGTH: 336
<212> TYPE: PRT
<213> ORGANISM: Pseudomonas ogarae

<400> SEQUENCE: 28

Met Lys Ile Ala Ile Val Asn Asp Met Pro Leu Ala Val Glu Ala Leu
1               5                   10                  15

Arg Arg Ala Leu Ala Phe Glu Pro Ala His Gln Leu Val Trp Val Ala
            20                  25                  30

Ala Asn Gly Ala Glu Ala Val Gln Arg Ser Ala Glu Tyr Thr Pro Asp
            35                  40                  45

Leu Ile Leu Met Asp Leu Phe Met Pro Val Met Asp Gly Val Glu Ala
            50                  55                  60

Thr Arg Arg Ile Met Ala Asp Ser Pro Cys Ala Ile Val Ile Val Thr
65                  70                  75                  80

Gly Asp Ser Gln Gln Asn Val His Arg Val Phe Glu Ala Met Gly His
            85                  90                  95

Gly Ala Leu Asp Val Val Asp Thr Pro Ala Leu Gly Val Gly Asn Pro
            100                 105                 110

Ala Asp Ala Ala Ala Pro Leu Leu Arg Lys Ile Thr Asn Ile Gly Trp
            115                 120                 125
```

Leu Ile Gly Glu Arg Asn Lys Arg Glu Arg Pro Ala Pro Ala Ala Gln
130                 135                 140

Arg Ala Val Ser Arg Lys Ser Leu Val Ala Ile Gly Ser Ser Ala
145                 150                 155                 160

Gly Gly Pro Ala Ala Leu Glu Val Leu Lys Ala Leu Pro Arg Asp
            165                 170                 175

Phe Thr Pro Ala Ile Val Leu Val Gln His Val Asp Glu Val Phe Ala
            180                 185                 190

Ala Gly Met Ala Glu Trp Leu Gly Ser Val Ser Gly His Thr Val Arg
            195                 200                 205

Leu Ala Arg Gln Gly Glu Thr Pro Gln Ser Gly Thr Val Leu Leu Ala
210                 215                 220

Gly Thr Asn His His Leu Arg Leu Leu Lys Asp Gly Thr Leu Ala Tyr
225                 230                 235                 240

Thr Ala Glu Pro Val Asn Glu Ile Tyr Arg Pro Ser Ile Asp Val Phe
                245                 250                 255

Phe Glu Ser Val Ala Gln Tyr Trp Ser Gly Asp Ala Val Gly Val Leu
                260                 265                 270

Leu Thr Gly Met Gly Arg Tyr Gly Ala Gln Gly Leu Lys Leu Met Arg
            275                 280                 285

Gln Gln Gly Tyr Val Thr Ile Ala Gln Asp Gln Arg Ser Ser Ala Val
290                 295                 300

Tyr Gly Met Pro Lys Ala Ala Ala Ile Asp Ala Ala His Ile
305                 310                 315                 320

Leu Ala Leu Asp Ala Ile Ala Pro Arg Leu Leu Glu Ile Phe Thr Pro
            325                 330                 335

<210> SEQ ID NO 29
<211> LENGTH: 477
<212> TYPE: PRT
<213> ORGANISM: Pseudomonas aeruginosa

<400> SEQUENCE: 29

Met Ser Arg Ala Ala Val Pro Ser Val Arg Arg Leu Leu Val Asn
1               5                   10                  15

Leu Leu Val Gly Phe Val Leu Cys Trp Leu Ser Val Ala Ala Leu Thr
                20                  25                  30

Tyr His Leu Ser Leu Lys Gln Val Asn Arg Leu Phe Asp Asp Met
            35                  40                  45

Val Asp Phe Gly Glu Ala Ala Leu Arg Leu Leu Asp Leu Ala Thr Glu
        50                  55                  60

Asp Gln Ala Gly Glu Asp Gly Ser Ile Thr Glu Ile Ile Glu Arg Ser
65                  70                  75                  80

Arg Glu Ala Ile Gln Gly Leu Pro Leu Leu Arg Arg Glu Ser Ala Leu
                85                  90                  95

Gly Tyr Ala Leu Trp Arg Asp Gly Gln Pro Leu Leu Ser Ser Leu Asn
            100                 105                 110

Leu Pro Pro Glu Ile Thr Ala Gln Gly Pro Gly Phe Ser Thr Val Glu
            115                 120                 125

Ala Gln Gly Thr His Trp Arg Val Leu Gln Leu Asn Ile Asp Gly Phe
130                 135                 140

Gln Ile Trp Ile Ser Glu Asn Leu Ile Tyr Arg Gln His Thr Met Asn
145                 150                 155                 160

Leu Leu Leu Phe Tyr Ser Leu Phe Pro Leu Leu Leu Ala Leu Pro Leu
                165                 170                 175

Leu Gly Gly Leu Val Trp Phe Gly Val Ala Arg Gly Leu Ala Pro Leu
            180                 185                 190

Arg Glu Val Gln Ala Glu Val Gln Gln Arg Ser Ala Arg His Leu Gln
            195                 200                 205

Pro Ile Ala Val Glu Ala Val Pro Leu Glu Ile Arg Gly Leu Ile Asp
210                 215                 220

Glu Leu Asn Leu Leu Glu Arg Leu Arg Thr Ala Leu Glu Ala Glu
225                 230                 235                 240

Arg Arg Leu Thr Ser Asp Ala Ala His Glu Ile Arg Thr Pro Leu Ala
                245                 250                 255

Ser Leu Arg Thr His Ala Gln Val Ala Leu Arg Ser Glu Asp Pro Lys
                260                 265                 270

Ala His Ala Arg Gly Leu Leu Gln Val Ser Arg Ser Val Glu Arg Ile
                275                 280                 285

Ser Thr Leu Met Glu Gln Ile Leu Leu Leu Ala Arg Leu Asp Gly Asp
            290                 295                 300

Ala Leu Leu Glu Gln Phe His Pro Val Asn Leu Ala Thr Leu Ala Glu
305                 310                 315                 320

Asp Val Leu Ser Glu Leu Ala Arg Gln Ala Ile Asp Lys Asp Ile Glu
                325                 330                 335

Leu Ser Leu His Gln Glu Thr Val Tyr Val Met Gly Ile Asp Leu Trp
            340                 345                 350

Leu Lys Ala Met Val Gly Asn Leu Val Gly Asn Ala Leu Arg Tyr Thr
            355                 360                 365

Pro Ala Gly Gly Gln Val Glu Ile Arg Val Glu Asn Arg Ala Gln His
            370                 375                 380

Ala Val Leu Arg Val Arg Asp Asn Gly Pro Gly Val Ala Leu Glu Glu
385                 390                 395                 400

Gln Gln Ala Ile Phe Thr Arg Phe Tyr Arg Ser Pro Ala Thr Ser Ser
                405                 410                 415

Gly Glu Gly Ser Gly Leu Gly Leu Pro Ile Val Lys Arg Ile Val Glu
            420                 425                 430

Leu His Phe Gly Ser Ile Gly Leu Gly Lys Gly Leu Glu Gly Lys Gly
            435                 440                 445

Leu Glu Val Gln Val Phe Leu Pro Lys Thr Gln Pro Asp Ala Thr Arg
450                 455                 460

Pro Pro Ala Arg Gly Pro Asp Ser Gly Arg Ser His Ile
465                 470                 475

<210> SEQ ID NO 30
<211> LENGTH: 346
<212> TYPE: PRT
<213> ORGANISM: Pseudomonas aeruginosa

<400> SEQUENCE: 30

Met Met Asn Leu Trp Leu Leu Leu Pro Ala Val Ala Ala Leu Ser Leu
1               5                   10                  15

Leu Leu Thr Ala Gly Leu Arg Arg Tyr Ala Ile Ala Arg Ser Leu Ile
            20                  25                  30

Asp Val Pro Asn Ala Arg Ser Ser His Gln Val Pro Thr Pro Arg Gly
            35                  40                  45

Gly Gly Val Ala Ile Val Leu Ser Phe Leu Leu Ala Val Leu Leu Ala
        50                  55                  60

Ala Ile Leu Gly Ala Val Lys Pro Asp Leu Ala Thr Gly Ile Leu Gly

```
            65                  70                  75                  80
        Ala Gly Ile Gly Ile Ala Leu Leu Gly Phe Leu Asp Asp His Gly His
                            85                  90                  95

Ile Ala Ala Arg Trp Arg Leu Leu Gly His Phe Ala Gly Ala Cys Trp
                        100                 105                 110

Leu Leu Tyr Trp Leu Gly Gly Leu Pro Ala Leu Ala Phe Phe Gly Leu
                        115                 120                 125

Val Val Asp Leu Gly Trp Val Gly His Ile Ala Ala Phe Tyr Leu
                    130                 135                 140

Val Trp Met Leu Asn Leu Tyr Asn Phe Met Asp Gly Ile Asp Gly Ile
        145                 150                 155                 160

Ala Ser Val Glu Ala Val Cys Val Cys Val Gly Ala Ala Leu Leu Val
                        165                 170                 175

Val Val Ser Gly Val Gly Ser Asp Glu Ala Ser Gln Gly Val Trp Leu
                    180                 185                 190

Ala Ala Leu Leu Ala Ala Ala Val Thr Gly Phe Leu Phe Trp Asn Phe
                    195                 200                 205

Pro Pro Ala Arg Ile Phe Met Gly Asp Ala Gly Ser Gly Phe Leu Gly
                    210                 215                 220

Val Ile Ile Gly Gly Leu Ser Leu Gln Ala Ala Trp Val Ser Pro Gln
        225                 230                 235                 240

Leu Phe Trp Gly Trp Leu Ile Leu Leu Gly Val Phe Ile Val Asp Ala
                    245                 250                 255

Thr Leu Thr Leu Leu Arg Arg Leu Leu Arg Gly Asp Lys Val Tyr Glu
                    260                 265                 270

Ala His Arg Ser His Ala Tyr Gln Tyr Ala Ser Arg His Tyr Gly Arg
                    275                 280                 285

His Leu Pro Val Thr Leu Ala Val Gly Gly Ile Asn Ile Phe Trp Leu
                    290                 295                 300

Leu Pro Leu Ala Leu Leu Val Ala Ala Gly Lys Ile Asp Gly Met Leu
        305                 310                 315                 320

Ala Leu Leu Ile Gly Tyr Leu Pro Leu Ala Phe Leu Ala Leu Arg Phe
                        325                 330                 335

Lys Ala Gly Val Leu Glu Ser Arg Ala Ala
                        340                 345

<210> SEQ ID NO 31
<211> LENGTH: 335
<212> TYPE: PRT
<213> ORGANISM: Pseudomonas aeruginosa

<400> SEQUENCE: 31

Met Arg Ile Gly Ile Val Asn Asp Met Pro Leu Ala Val Glu Ala Leu
        1               5                   10                  15

Arg Arg Ala Leu Ala Phe Glu Pro Gln His Gln Ile Val Trp Val Ala
                        20                  25                  30

Ser Asn Gly Ala Glu Ala Val Thr Gln Cys Ala Ala Asp Thr Pro Asp
                    35                  40                  45

Val Val Leu Met Asp Leu Leu Met Pro Val Met Asp Gly Val Glu Ala
                50                  55                  60

Thr Arg Arg Ile Met Ala Glu Ser Pro Cys Ala Ile Val Ile Val Thr
        65                  70                  75                  80

Val Asp Ile Glu Gln Asn Val His Arg Val Phe Glu Ala Met Gly Tyr
                        85                  90                  95
```

-continued

```
Gly Ala Leu Asp Ala Val Asn Thr Pro Ala Leu Gly Ile Gly Asn Pro
            100                 105                 110

Gln Thr Ala Ala Ala Pro Leu Leu Arg Lys Ile Gln Asn Val Gly Trp
        115                 120                 125

Leu Ile Gly Gln Arg Asp Asn Arg Gly Lys Val Gln Val Val Pro Pro
        130                 135                 140

Lys Ala Gly Gly Ala Arg Gln Arg Leu Val Ala Ile Gly Ala Ser Ala
145                 150                 155                 160

Gly Gly Pro Ala Ser Leu Ala Val Leu Leu Lys Gln Leu Pro Ala Ser
                165                 170                 175

Phe Asn Ala Ala Val Val Leu Val Gln His Val Asp Glu Val Phe Ala
            180                 185                 190

Ala Gly Met Ala Glu Trp Leu Ala Ser Glu Ser Lys Leu Pro Val Arg
        195                 200                 205

Leu Ala Arg Asp Gly Glu Pro Pro Ile Pro Gly Gln Ile Leu Leu Ala
        210                 215                 220

Gly Thr Asn Asn His Ile Arg Leu Leu Arg Asn Gly Ser Leu Val Tyr
225                 230                 235                 240

Thr Ala Glu Pro Arg Ser Phe Val Tyr Arg Pro Ser Ile Asp Val Phe
                245                 250                 255

Phe Glu Ser Val Ala Asn Tyr Trp Arg Gly Asp Ala Val Gly Val Leu
                260                 265                 270

Leu Thr Gly Met Gly Arg Asp Gly Ala Gln Gly Leu Lys Gln Met Arg
            275                 280                 285

Glu Arg Gly Phe Leu Thr Ile Ala Gln Asp Gln Ala Ser Cys Ala Val
    290                 295                 300

Tyr Gly Met Pro Lys Ala Ala Ala Ile Asp Ala Ala Val Gln Ile
305                 310                 315                 320

Leu Ser Leu Glu Lys Ile Ala Pro Arg Leu Ala Glu Val Phe Asp
                325                 330                 335
```

METHODS AND COMPOSITIONS FOR TREATMENT OF ANTIBIOTIC-RESISTANT BACTERIAL INFECTIONS

CROSS REFERENCE TO RELATED APPLICATIONS

This application claims the benefit of U.S. Provisional Patent Application No. 63/287,686 filed Dec. 9, 2021, and U.S. Provisional Patent Application No. 63/177,046 filed Apr. 20, 2021, the disclosure of each of which is incorporated herein by reference in its entirety.

STATEMENT AS TO FEDERALLY SPONSORED RESEARCH

This invention was made with government support under Grant No. AI124302 awarded by the National Institutes of Health. The government has certain rights in the invention.

REFERENCE TO A SEQUENCE LISTING SUBMITTED VIA EFS-WEB

The sequence Listing associated with this application is filed in electronic format via Patent Center and is hereby incorporated by reference into the specification in its entirety. The name of the text file containing the Sequence Listing is 2201587_ST25.txt. The size of the text file is 28,138 bytes, and the text filed was created on Nov. 7, 2023.

The ability of a bacterial population to evolve resistance to an antibiotic depends on several factors including the availability of mutations that increase resistance and the strength of selection imposed by the compound.

WLBU2 (also called PLG0206) is an example of an engineered peptide, derived from and inspired by the LL-37 peptide produced by our own bodies, which inserts into the bacterial membrane and leads to cell death. Antimicrobial peptides derived from the LL-37 peptide, as exemplified by WLBU2, can be highly effective against ESKAPE (*Enterococcus faecium, Staphylococcus aureus, Klebsiella pneumoniae, Acinetobacter baumannii, Pseudomonas aeruginosa* and *Enterobacter* spp.) pathogens in vitro and in vivo. Antibiotic activity is typically measured against planktonic cells as biofilms are highly antibiotic tolerant, but WLBU2 has demonstrated a high activity against *P. aeruginosa* and *S. aureus* biofilms.

Despite the exhibition of high antimicrobial activity, resistance to such antimicrobial peptides is possible, though seen only in *P. aeruginosa*. Understanding the mechanism of development of resistance to LL-37-derived polypeptides is therefore desirable in order to inform clinical antibiotic treatment options.

SUMMARY

Disclosed herein are methods that be used for treating a bacterial infection in a subject in need thereof, comprising administering to the subject a formulation comprising an antimicrobial peptide or salt thereof in a therapeutically effective amount to treat the bacterial infection, wherein the therapeutically effective amount is sufficient to reduce a level of bacteria that comprise a mutation in a pmrABC operon in an in vitro assay to a greater extent than administration of a comparable antimicrobial polypeptide comprising a polymyxin peptide.

In some embodiments, the method of treating a bacterial infection in a subject in need thereof can comprise administering to the subject a formulation comprising an antimicrobial peptide or salt thereof, wherein the bacteria requires at least two mutations to develop resistance against the antimicrobial peptide or salt thereof, and wherein the administering is sufficient to treat the bacterial infection in bacteria with mutations with only a single mutation, as determined by an in vitro assay, and wherein the administering is sufficient to treat the bacterial infection. In some embodiments, at least two mutations are in genes selected from the group consisting of pmrB, wspA, wspF, yfiR, wbpM, orfN, trbL, and morA.

Further disclosed herein are methods that can be used for treating a bacterial infection in a subject in need thereof, comprising administering to the subject a formulation comprising an antimicrobial peptide or salt thereof, wherein the bacteria are selected from the group consisting of *A. baumannii* ATCC 17978, *P. aeruginosa* PA14, and a combination thereof, and wherein the administering is sufficient to treat the bacterial infection.

In some aspects, the antimicrobial peptide or salt thereof can comprise from about 70% to about 100% homology to a polypeptide of sequence:

```
                                          (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-
Arg-Arg-Trp-Trp-Arg-Arg;

(SEQ ID NO: 19)
Arg-Arg-Val-Val-Arg-Arg-Val-Arg-Arg-Val-Val-Arg-
Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-
Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-
Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-
Arg-Arg-Val-Val-Arg-Arg-Val-Arg-Arg-Val-Val-Arg-
Arg-Val-Val-Arg-Val-Val-Arg-Arg-Val-Val-Arg-Arg;

(SEQ ID NO: 22)
Val-Arg-Arg-Val-Trp-Arg-Arg-Val-Val-Arg-Val-Val-
Arg-Arg-Trp-Val-Arg-Arg-Val-Arg-Arg-Val-Trp-Arg-
Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-
Arg-Val-Val-Arg-Val-Val-Arg-Arg-Val-Val-Arg-Arg-
Val-Arg-Arg-Val-Val-Arg-Arg-Val-Val-Arg-Val-Val-
Arg-Arg-Val-Val-Arg-Arg;
```

-continued

```
                                           (SEQ ID NO: 24)
Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-

Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Arg-Val-Val.
```

In some embodiments, the formulation described herein can be a wash. In some embodiments, administering the formulation described here in can comprise a local application of the wash to a body part of the subject. In some aspects, the local application can comprise contacting a device present in the body part of the subject with the wash. In some embodiments, device can be a prosthetic joint. In some embodiments, the formulation can be an oral formulation. In some aspects, the formulation can be an injectable formulation. In some aspects, the bacteria can be present in a biofilm. In some embodiments, the device can be implanted in the subject and the wash occurs on the device. In some embodiments, the device can be an intraocular lens, an intrastromal corneal ring segment; a cochlear implant; a tympanostomy tube; a neurostimulator; an artificial heart; an artificial heart valve; an implantable cardioverter-defibrillator; a cardiac pacemaker; a coronary stent; an intrauterine device; a breast implant; a nose prosthesis; an ocular prosthesis; an injectable filler; an implantable gastric stimulator; a diaphragmatic/phrenic nerve stimulator; a neurostimulator; a surgical mesh; a penile prosthesis; or a part thereof. In some aspects, the bacteria can be a multiple drug resistant bacteria that is resistant to at least one antibiotic. In some embodiments, the at least one antibiotic can be selected from the group consisting of a cephalosporin, a fluoroquinolone, a carbapenem, a colistin, an aminoglycoside, vancomycin, streptomycin, and methicillin. In some aspects, the subject can have a disease or condition selected from the group consisting of a cataract, glaucoma, a keratoconus, a visual impairment, otosclerosis, hearing loss otitis media, epilepsy, Parkinson's disease, treatment-resistant depression, heart failure, cardiac arrhythmia ventricular tachycardia, valvular heart disease, angina pectoris, atherosclerosis, a bone fracture, osteoarthritis, rheumatoid arthritis, avascular necrosis (AVN) or osteonecrosis (ON) congenital dislocation of the hip joint (CDH), hip dysplasia, acetabular dysplasia (shallow hip socket), frozen shoulder, loose shoulder, traumatized and malaligned joint, joint stiffness, scoliosis, spinal stenosis, chronic pain, unintended pregnancy, menorrhagia, skin trauma, gastroesophageal reflux disease, gastroparesis, respiratory failure, sleep apnea, urinary and fecal incontinence, erectile dysfunction, urinary tract infection, hospital acquired pneumonia, ventilator acquired pneumonia, an intra-abdominal infection, a blood stream infection, a periprosthetic joint infection, and any combination thereof. In some aspects, the antimicrobial peptide or salt thereof can further comprises water. In some aspects, the antimicrobial peptide or salt thereof can further comprises an excipient, a diluent, or a carrier. In some embodiments, the antimicrobial peptide or salt thereof can further comprise a cysteamine, a surfactant, or a small molecule.

According to another aspect or embodiment, a method of treating a bacterial infection in a subject in need thereof is provided. The method comprises administering to the subject a formulation comprising an antimicrobial peptide or salt thereof in a therapeutically effective amount to treat the bacterial infection, wherein the antimicrobial peptide or salt thereof does not comprise a polymyxin peptide, wherein the formulation reduces a level of bacteria that comprises a mutation in the pmrABC operon gene, relative to a wildtype pmrABC operon gene present in a wild type *A. baumannii* ATCC 17978 or *P. aeruginosa* PA14 bacteria strain, to an extent comparable to a reduction by the formulation of a level of a bacteria strain with the wildtype pmrABC operon gene, as determined by an in vitro assay.

According to another aspect or embodiment, a method of treating a bacterial infection in a subject in need thereof is provided. The method comprises administering to the subject a formulation comprising an antimicrobial peptide or salt thereof, wherein: the administering is sufficient to treat the bacterial infection by inhibiting growth of bacteria with only a perturbation in a single gene, as determined by an in vitro assay; and after an extended exposure to said antimicrobial peptide, when the bacteria acquires a perturbation in at least two genes, the bacteria develop resistance against said antimicrobial peptide, wherein one of the at least two genes affects an outer membrane of the bacterial and one of the at least two genes affects aggregation of the bacteria.

According to another aspect or embodiment, a method of treating a bacterial infection in a subject in need thereof is provided. The method comprises administering to the subject a formulation comprising an antimicrobial peptide or salt thereof, wherein the bacteria is selected from the group consisting of *A. baumannii*, *P. aeruginosa*, and a combination thereof, and wherein the administering is sufficient to treat the bacterial infection.

According to another aspect or embodiment, a method for treating a bacterial infection in a subject in need thereof is provided. The method comprises administering to the subject a formulation comprising an antimicrobial peptide or salt thereof in a therapeutically effective amount to treat the bacterial infection, wherein the antimicrobial peptide or salt thereof comprises from about 70% to about 100% homology to a polypeptide of sequence:

```
                                           (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-

Arg-Arg-Trp-Trp-Arg-Arg;

(SEQ ID NO: 19)
Arg-Arg-Val-Val-Arg-Arg-Val-Arg-Arg-Val-Val-Arg-

Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-

Arg-Val-Val-Arg-Val-Val-Arg-Arg-Trp-Val-Arg-Arg;
```

-continued (SEQ ID NO: 20)
Arg-Arg-Trp-Trp-Arg-Arg-Trp-Arg-Arg-Trp-Trp-Arg-

Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Val-Val-Arg-Val-Arg;

(SEQ ID NO: 22)
Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-

Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg;

(SEQ ID NO: 24)
Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-

Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Arg-Arg-Val-Val-Arg-Arg-Trp-Arg-Val-Val;

and wherein the bacterial infection comprises a bacteria strain with a higher mutation rate compared to the bacteria strain's ancestor (non-mutator) strain.

According to another aspect or embodiment, a method of treating a bacterial infection comprising a bacteria, such as a gram-negative bacteria, such as an *A. baumannii* or *P. aeruginosa* bacteria, comprising a mutation in at least one gene affecting an outer membrane of the bacteria species and/or aggregation of the bacteria species or a hypermutator bacteria strain of the bacteria, in a subject, is provided. The method comprises: obtaining a sample of the bacteria of the bacterial infection from the subject; administering to the subject a formulation comprising an antimicrobial peptide or salt thereof in a therapeutically effective amount to treat the bacterial infection; and monitoring a bacterial species obtained from the patient at one or more times after administration of the formulation for development of one or more additional mutations in at least one gene affecting an outer membrane of the bacteria species and/or aggregation of the bacteria species.

Non-limiting aspects or embodiments of the present invention will now be described in the following numbered clauses:

Clause 1: A method of treating a bacterial infection in a subject in need thereof, comprising administering to the subject a formulation comprising an antimicrobial peptide or salt thereof in a therapeutically effective amount to treat the bacterial infection, wherein the antimicrobial peptide or salt thereof does not comprise a polymyxin peptide, wherein the formulation reduces a level of bacteria that comprises a mutation in the pmrABC operon gene, relative to a wildtype pmrABC operon gene present in a wild type *A. baumannii* ATCC 17978 or *P. aeruginosa* PA14 bacteria strain, to an extent comparable to a reduction by the formulation of a level of a bacteria strain with the wildtype pmrABC operon gene, as determined by an in vitro assay.

Clause 2: A method of treating a bacterial infection in a subject in need thereof, comprising administering to the subject a formulation comprising an antimicrobial peptide or salt thereof, wherein: the administering is sufficient to treat the bacterial infection by inhibiting growth of bacteria with only a perturbation in a single gene, as determined by an in vitro assay; and after an extended exposure to said antimicrobial peptide, when the bacteria acquires a perturbation in at least two genes, the bacteria develop resistance against said antimicrobial peptide, wherein one of the at least two genes affects an outer membrane of the bacterial and one of the at least two genes affects aggregation of the bacteria.

Clause 3: The method of clause 2, wherein the at least two mutations are in a gene selected from the group consisting of a pmrB gene, a wspA gene, a wspF gene, a yfiR gene, a wbpM gene, a orfN gene, a trbL gene, and a morA gene.

Clause 4: The method of clause 3, wherein the at least two mutations are in the pmrB gene, wherein the pmrB gene encodes a histidine kinase, wherein the at least two mutations in the pmrB gene occur in at least two codons of the pmrB gene, and wherein each of the at least two mutations occur in the histidine kinase at a position in SEQ ID No. 26 individually selected from the group consisting of 18, 28, 44, 47, 180, 185, 248, 296, 318, 480, and equivalent positions thereof.

Clause 5: The method of clause 4, wherein the at least two mutations in the pmrB gene result in at least two different changes in the histidine kinase selected from the group consisting of V28L, L18P, A248T, L180P, V28A, D47G, F44L, L318P, V185A, L296P, and F408P.

Clause 6: The method of clause 3, wherein the at least two mutations are in the orfN gene, wherein the orfN gene encodes a putative group 4 glycosyl transferase, wherein the at least two mutations in the orfN gene in at least two codons of the orfN gene, and wherein one of the at least two mutations occur in the putative group 4 glycosyl transferase at position at position 10 or an equivalent position thereof in SEQ ID NO: 27.

Clause 7: The method of clause 6, wherein the at least two mutations in the orfN gene result in at least two different changes in the glycosyl transferase, wherein one of the at least two mutations comprise (10)G to (9)G.

Clause 8: The method of clause 3, wherein the at least two mutations are in the wspF gene, wherein the wspF gene encodes a protein-glutamate methylesterase, wherein the at least two mutations in the wspF gene occur in at least two codons of the wspF gene, and wherein each of the at least two mutations occur in the protein-glutamate methylesterase at a position in SEQ ID NO: 28 individually selected from the group consisting of 20, 51, 159, 199, 222, 274, 280, 282, 283, 299, and 319, or the equivalent positions.

Clause 9: The method of clause 8, wherein the at least two mutations in the wspF gene result in at least two different changes in the protein-glutamate methylesterase selected from the group consisting of L20P, L51P, S159L, L199P, L222P, T274I, G280D, and G283D.

Clause 10: A method of treating a bacterial infection in a subject in need thereof, comprising administering to the subject a formulation comprising an antimicrobial peptide or salt thereof, wherein the bacteria is selected from the group consisting of *A. baumannii*, *P. aeruginosa*, and a combination thereof, and wherein the administering is sufficient to treat the bacterial infection.

Clause 11: The method of any one of clauses 1-10, wherein the antimicrobial peptide or salt thereof comprises from about 70% to about 100% homology to a polypeptide of sequence:

```
                                       (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-

Arg-Arg-Trp-Trp-Arg-Arg;

(SEQ ID NO: 19)
Arg-Arg-Val-Val-Arg-Arg-Val-Arg-Arg-Val-Val-Arg-

Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-

Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;

(SEQ ID NO: 22)
Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-

Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg;

(SEQ ID NO: 24)
Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-

Val-Arg-Arg-Val-Trp-Arg-Arg-Val-Arg-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Arg-Val-Val.
```

Clause 12: The method of any one of clauses 1-11, wherein the formulation is a wash.

Clause 13: The method of clause 12, wherein the administering comprises a local application of the wash to a body part of the subject.

Clause 14: The method of clause 13, wherein the local application comprises contacting a device present in the body part of the subject with the wash.

Clause 15: The method of clause 14, wherein the device is a prosthetic joint.

Clause 16: The method of any one of clauses 1-11, wherein the formulation is an oral formulation.

Clause 17: The method of any one of clauses 1-11, wherein the formulation is an injectable formulation.

Clause 18: The method of any one of clauses 1-17, wherein the bacteria is present in a biofilm.

Clause 19: The method of clause 14, wherein the device is implanted in the subject and the wash occurs on the device.

Clause 20: The method of clause 14, the device is an intraocular lens, an intrastromal corneal ring segment; a cochlear implant; a tympanostomy tube; a neurostimulator; an artificial heart; an artificial heart valve; an implantable cardioverter-defibrillator; a cardiac pacemaker; a coronary stent; an intrauterine device; a breast implant; a nose prosthesis; an ocular prosthesis; an injectable filler; an implantable gastric stimulator; a diaphragmatic/phrenic nerve stimulator; a neurostimulator; a surgical mesh; a penile prosthesis; or a part thereof.

Clause 21: The method of any one of clauses 1-20, wherein the bacteria is a multiple drug resistant bacteria that is resistant to at least one antibiotic.

Clause 22: The method of clause 21, wherein the at least one antibiotic is selected from the group consisting of a cephalosporin, a fluoroquinolone, a carbapenem, a colistin, an aminoglycoside, vancomycin, streptomycin, and methicillin.

Clause 23: The method of any one of clauses 1-22, wherein the subject has a disease or condition selected from the group consisting of a cataract, glaucoma, a keratoconus, a visual impairment, otosclerosis, hearing loss otitis media, epilepsy, Parkinson's disease, treatment-resistant depression, heart failure, cardiac arrhythmia ventricular tachycardia, valvular heart disease, angina pectoris, atherosclerosis, a bone fracture, osteoarthritis, rheumatoid arthritis, avascular necrosis (AVN) or osteonecrosis (ON) congenital dislocation of the hip joint (CDH), hip dysplasia, acetabular dysplasia (shallow hip socket), frozen shoulder, loose shoulder, traumatized and malaligned joint, joint stiffness, scoliosis, spinal stenosis, chronic pain, unintended pregnancy, menorrhagia, skin trauma, gastroesophageal reflux disease, gastroparesis, respiratory failure, sleep apnea, urinary and fecal incontinence, erectile dysfunction, urinary tract infection, hospital acquired pneumonia, ventilator acquired pneumonia, an intra-abdominal infection, a blood stream infection, a periprosthetic joint infection, and any combination thereof.

Clause 24: The method of clause 11, wherein the antimicrobial peptide or salt thereof further comprises water.

Clause 25: The method of clause 11, wherein the antimicrobial peptide or salt thereof further comprises an excipient, a diluent, or a carrier.

Clause 26: The method of clause 11, wherein the antimicrobial peptide or salt thereof further comprises a cysteamine, a surfactant, or a small molecule.

Clause 27: A method for treating a bacterial infection in a subject in need thereof, comprising administering to the subject a formulation comprising an antimicrobial peptide or salt thereof in a therapeutically effective amount to treat the bacterial infection, wherein the antimicrobial peptide or salt thereof comprises from about 70% to about 100% homology to a polypeptide of sequence:

```
                                           (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-

Arg-Arg-Trp-Trp-Arg-Arg;

(SEQ ID NO: 19)
Arg-Arg-Val-Val-Arg-Arg-Val-Arg-Arg-Val-Val-Arg-

Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-

Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;

(SEQ ID NO: 22)
Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-

Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg;

(SEQ ID NO: 24)
Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-

Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Arg-Val-Val;
``` and wherein the bacterial infection comprises a bacteria strain with a higher mutation rate compared to the bacteria strain's ancestor (non-mutator) strain.

Clause 28: A method of treating a bacterial infection comprising a bacteria, such as a gram-negative bacteria, such as an *A. baumannii* or *P. aeruginosa* bacteria, comprising a mutation in at least one gene affecting an outer membrane of the bacteria species and/or aggregation of the bacteria species or a hypermutator bacteria strain of the bacteria, in a subject, comprising: obtaining a sample of the bacteria of the bacterial infection from the subject; administering to the subject a formulation comprising an antimicrobial peptide or salt thereof in a therapeutically effective amount to treat the bacterial infection; and monitoring a bacterial species obtained from the patient at one or more times after administration of the formulation for development of one or more additional mutations in at least one gene affecting an outer membrane of the bacteria species and/or aggregation of the bacteria species.

Clause 29: The method of clause 28, wherein the bacteria is *A. baumannii* or *P. aeruginosa*.

Clause 30: The method of clause 28 or 29, further comprising before and/or during administering the formulation to the patient, determining if bacteria obtained from the patient comprises a mutation in at least one gene affecting an outer membrane of the bacteria species and/or aggregation of the bacteria species.

Clause 31: The method of any one of clauses 28-30, wherein if one or more mutations in at least one gene affecting an outer membrane of the bacteria species and/or aggregation of the bacteria species is present in the bacteria, the subject is administered a dose of the formulation comprising the antimicrobial peptide or salt thereof in amounts exceeding a minimum inhibitory concentration (MIC) for the bacterial species.

Clause 32: The method of any one of clauses 28-31, wherein if the bacterial species develops resistance to the formulation comprising the antimicrobial peptide or salt thereof, or develops one or more additional mutations in at least one gene affecting an outer membrane of the bacteria species and/or aggregation of the bacteria species, discontinuing administering of the formulation to the subject.

Clause 33: The method of any one of clauses 28-32, wherein the gene affecting an outer membrane of the bacteria species and/or aggregation of the bacteria species is a pmrB gene, a WspA gene, a wspF gene, a yfiR gene, a wbpM gene, a orfN gene, a trbL gene, a morA gene, or a combination thereof.

Clause 34: The method of clause 33, wherein the bacteria comprises a mutation in the pmrB gene and in the orfN gene.

Clause 35: The method of clause 34, wherein the bacteria comprises a mutation mutation in the wspF gene.

Clause 36: The method of clause 33, wherein one or more of the one or more mutations is in the pmrB gene, wherein the pmrB gene encodes a histidine kinase, wherein the mutations in the pmrB gene occur in at least one codon of the pmrB gene, and wherein each of the one or more mutations occur in the histidine kinase at a position in SEQ ID NO: 26 individually selected from the group consisting of 18, 28, 44, 47, 180, 185, 248, 296, 318, 480, and equivalent positions thereof.

Clause 37: The method of clause 36, wherein the one or more mutations in the pmrB gene includes one or more of: V28L, L18P, A248T, L180P, V28A, D47G, F44L, L318P, V185A, L296P, and F408P.

Clause 38: The method of clause 33, wherein one or more of the one or more mutations is in the orfN gene, wherein the orfN gene encodes a putative group 4 glycosyl transferase, wherein the at least one mutation in the orfN gene is in at least one codon of the orfN gene, and wherein the at least one mutation occurs in the putative group 4 glycosyl transferase at position at position 10 or an equivalent position thereof in SEQ ID NO: 27.

Clause 39: The method of clause 38, wherein the mutation in the orfN gene result in at least two different changes in the glycosyl transferase, wherein one of the at least two mutations comprise (10)G to (9)G.

Clause 40: The method of clause 33, wherein one or more of the one or more mutations is in the wspF gene, wherein the wspF gene encodes a protein-glutamate methylesterase, wherein the at least one mutation in the wspF gene occurs in one or more codons of the wspF gene, and wherein each of the at least one mutation occurs in the protein-glutamate methylesterase at a position in SEQ ID NO: 28, or an equivalent position.

Clause 41: The method of clause 40, wherein the one or more mutations in the wspF gene includes one or more of: L20P, L51P, S159L, L199P, L222P, T274I, G280D, and G283D.

Clause 42: The method of any one of clauses 28-41, wherein the antimicrobial peptide or salt thereof comprises from about 70% to about 100% homology to a polypeptide of sequence:

```
                                         (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-

Arg-Arg-Trp-Trp-Arg-Arg;

(SEQ ID NO: 19)
Arg-Arg-Val-Val-Arg-Arg-Val-Arg-Arg-Val-Val-Arg-

Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-

Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;

(SEQ ID NO: 22)
Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-

Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg;

(SEQ ID NO: 24)
Arg-Val-Val-Arg-Val-Val-Arg-Arg-Val-Val-Arg-Arg-

Val-Arg-Arg-Val-Val-Arg-Arg-Val-Val-Arg-Val-Val-

Arg-Arg-Val-Val-Arg-Arg-Val-Arg-Arg-Val-Val-Arg-

Arg-Val-Val-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-

Val-Arg-Arg-Val-Trp-Arg-Arg-Val-Val-Arg-Val-Val-

Arg-Arg-Trp-Val-Arg-Arg-Val-Arg-Arg-Val-Trp-Arg-

Arg-Val-Arg-Val-Val-Arg-Arg-Trp-Arg-Val-Val.
```

Clause 43: The method of any one of clauses 28-41, wherein the antimicrobial peptide or salt thereof comprises SEQ ID NO: 1.

Clause 44: The method of any of clauses 28-43, wherein the bacterial species is a bacterial species with a higher mutation rate as compared to the bacterial species ancestor (non-mutator) strain.

Clause 45: The method of any one of clauses 28-44, further comprising determining that the bacterial species is resistant to Polymyxin B prior to administering the formulation comprising the antimicrobial peptide or salt thereof.

Clause 46: The method of clause 45, wherein bacterial species further comprises a mutation in a pmrABC operon gene.

Clause 47: The method of any one of clauses 28-46, wherein the formulation comprising the antimicrobial peptide or salt thereof reduces the level of bacteria that comprises the mutation in the pmrABC operon gene, relative to a wildtype pmrABC operon gene present in a wild type bacteria species, to an extent comparable to a reduction of a level of the bacteria that comprises the wildtype pmrABC operon gene by the formulation comprising the antimicrobial peptide or salt thereof, as determined by an in vitro assay.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the features and advantages of the present disclosure will be obtained by reference to the following detailed description that sets forth illustrative embodiments, in which the principles of the disclosure are utilized, and the accompanying drawings of which:

FIG. 5 are photographs showing isolated clones have at least two mutations involving LPS modification and O-antigen synthesis, some with additional biofilm mutations, affecting colony morphologies. Each wrinkly clone has a specific mutation that was not detected at the population level (wbpM and wspA), but they still fall into the functional categories associated with resistance shown in FIG. 4. The two wrinkly colonies have expected wsp mutations, while the two smooth morphotypes differ from their wild-type ancestor in size, shape, and coloration. It is notable that 3 of the 4 isolates acquired biofilm-associated mutations despite no explicit biofilm selection.

FIG. 7 is a diagram showing mutations selected in the presence of subinhibitory concentrations of WLBU2 (SEQ ID NO: 1) and their frequencies. Each column shows the mutations present in one population or clone: WP=whole population; Sm and Wr are the smooth and wrinkly clones isolated from population 1; Sm and Sc are smooth and small colonies isolated from population 2. Only mutated genes that evolved in WLBU2 (SEQ ID NO: 1) treated populations above 10% frequency found in the clones and not present in the non-WLBU2 (SEQ ID NO: 10) controls are shown.

DETAILED DESCRIPTION

Figure 1:
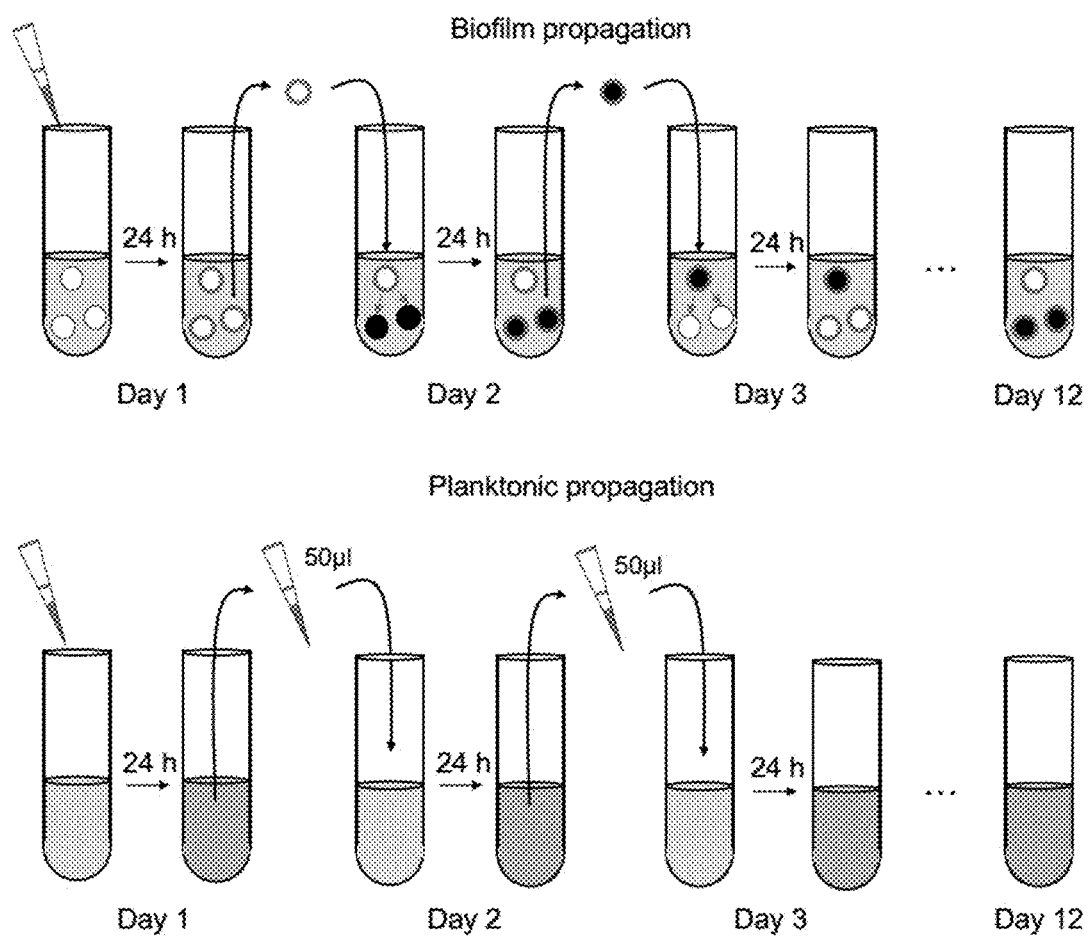
FIG. 1 is a schematic presentation of the biofilm propagation (top) and the planktonic propagation (bottom) used to propagate the sensitive strain in presence of WLBU2 (SEQ ID NO: 1).

The ability of a bacterial population to evolve resistance to an antibiotic may depend on several factors including the availability of mutations that increase resistance and the strength of selection imposed by the compound. Experimental evolution (EE) coupled with whole genome sequence (WGS) is a powerful strategy to characterize the genetic mechanisms of resistance. Propagation of a bacterial population in the presence of an antibiotic may eventually select those clones that are capable of surviving antibiotic exposure, and WGS of these populations or clones may reveal genetic causes of the resistance phenotype. This method is especially powerful when studying cationic peptides, as multiple mutations may be needed to revolve resistance to them.

WLBU2 (SEQ ID NO: 1) is an engineered amphipathic alpha helix derived from the LL-37 peptide that inserts into the bacterial membrane and leads to cell death. WLBU2 (SEQ ID NO: 1) was shown to be highly effective against ESKAPE (*Enterococcus faecium, Staphylococcus aureus, Klebsiella pneumoniae, Acinetobacter baumannii, Pseudomonas aeruginosa* and *Enterobacter* spp.) pathogens in vitro and in vivo even when the bacterial populations are protected by biofilms. Despite challenging several Gram-negative and Gram-positive pathogens with WLBU2 (SEQ ID NO: 1) in vitro and in animal models, only one study has shown that *P. aeruginosa* was able to increase resistance following long exposure to WLBU2 (SEQ ID NO:1). However, no mechanism of resistance have been described yet. Identifying the genes and the subsequent mutations that confer resistance to novel antibiotics is crucial as it enables more comprehensive understanding of this new antimicrobial compound's action and how resistance evolves to them. Further, these discoveries can increase the ability to predict emergence of antimicrobial resistance in clinical scenarios.
Peptides The development of antimicrobial agents is paramount due to the emergence of pathogens resistant to traditional antimicrobial compounds. Disclosed herein are peptides that comprise antimicrobial, antiviral, antifungal or antitumor activity when administered to a subject. A peptide described herein can be used to disrupt the integrity of a membrane by (a) binding to a negatively charged surface on a membrane; and/or (b) integrating into a membrane. The ability of a peptide disclosed herein to bind to a negatively charged surface on a membrane and/or integrate into a membrane can allow a peptide to act as a toxic agent to cells with a negatively charged surface by disrupting membrane integrity. In other embodiments, a peptide disclosed herein can have anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, and/or protozoicidal properties. Furthermore, while a peptide as described herein can bind and/or integrate into a bacterial membrane of both gram-positive and gram-negative membranes, a peptide can also have the surprising and unexpected ability to bind to and block the action of lipopolysaccharides (LPS) on the surface gram-negative bacteria. LPS are large molecules consisting of a lipid and a polysaccharide composed of O-antigen, outer core and inner core joined by a covalent bond. LPS can be found in the outer membrane of gram-negative bacteria. In some cases, LPS can elicit a strong immune response in animals. By binding to LPS molecules on the surface of a gram-negative bacterial strain, it is envisaged that the endotoxic activity of LPS can be mitigated The methods of treating a disease or condition described herein can be by administering to a subject a peptide or formulation containing a peptide as disclosed therein. For example, a peptide or formulation comprising a peptide described herein can be administered as an antimicrobial agent in order to at least partially inhibit the growth of a pathogen, such as bacteria, through disruption of the structural integrity of the bacterial cell membrane. A peptide described herein can be screened for broad spectrum activity against a variety of pathogens for broad utility when administered to a subject.

An antimicrobial peptide described herein can also be used as a means to produce an antimicrobial film for coating a device. In some embodiments, the peptides disclosed herein can be used to coat the interior and/or exterior of a medical device, for example, an implantable medical device. The coating of a device with a peptide disclosed herein can reduce the growth and proliferation of cells, bacteria, fungi or virus on a surface coated with a peptide. In some embodiments, coating an implantable medical device with a peptide disclosed herein can reduce the risk of an infection to a subject upon implanting the medical device in a subject.

It is further envisaged that a peptide described herein or formulation comprising a peptide described herein can be included in a kit. The kit can be utilized, for example, by a subject or healthcare professional to coat a device or to treat a condition or disease described herein.

The use of a protein scaffold based on lentiviral lytic proteins (LLPs) as a model for engineering broad spectrum antimicrobial compounds is described in U.S. Pat. No. 6,887,847. LLP based peptide analogs can be designed utilizing, for example, the following principles: (i) optimizing amphipathicity, (ii) substituting arginine (Arg) on the charged face and/or valine (Val) or tryptophan (Trp) on the hydrophobic face with another amino acid, and (iii) increasing peptide length.

The antimicrobial peptides may be derived from, and are analogs of, the LLP-1 peptide parent sequence corresponding to amino acids 828-856 of the HIV-1 viral isolate HXB2R Env, (see Table 1 below). The antimicrobial activity of other LLP-1 peptide analogues has been previously described (see, Tencza et al., 1999, Journal of Antimicrobial Chemotherapy 44:33-41, U.S. Pat. No. 5,714,577 of Montelaro et al. and U.S. Pat. No. 5,945,507 of Montelaro et al., the disclosures of which are incorporated herein by reference). The antimicrobial peptides may be LLP-1 analogs having modifications based on the following principles: (i) optimizing amphipathicity, (ii) substituting arginine (Arg) on the charged face and/or valine (Val) or tryptophan (Trp) on the hydrophobic face with another amino acid, and (iii) increasing peptide length; see Table 1). Amino acid sequences are provided, left-to-right, from their N-terminus to their C-terminus in 1 letter designations and 3 letter designations.

TABLE 1

Antimicrobial Peptides

| SEQ ID NO: | Amino Acid Sequence |
|---|---|
| 1 (WLBU-2) | RRWVRRVRRVWRRVVRVVRRWVRR<br>Arg-Arg-Trp-Val-Arg-Arg-Val-Arg-Arg-Val-Trp-Arg-Arg-Val-Val-Arg-Val-Val-Arg-Arg-Trp-Val-Arg-Arg |
| 2 | IRRRRRIRRRRRR<br>Ile-Arg-Arg-Arg-Arg-Arg-Ile-Arg-Arg-Arg-Arg-Arg-Arg |
| 3 | IRRRIRRIRRRIRRRIRR<br>Ile-Arg-Arg-Arg-Ile-Arg-Arg-Ile-Arg-Arg-Arg-Ile-Arg-Arg-Ile-Arg-Arg-Arg-Ile-Arg-Arg |
| 4 | IRRIIRRIRRIIRRIRRIIRR<br>Ile-Arg-Arg-Ile-Ile-Arg-Arg-Ile-Arg-Arg-Ile-Ile-Arg-Arg-Ile-Arg-Arg-Ile-Ile-Arg-Arg |
| 5 | VWRWVRRVWRWVRRVWRWVRR<br>Val-Trp-Arg-Trp-Val-Arg-Arg-Val-Trp-Arg-Trp-Val-Arg-Arg-Val-Trp-Arg-Trp-Val-Arg-Arg |
| 6 | VWRWVRRVWRWVRR<br>Val-Trp-Arg-Trp-Val-Arg-Arg-Val-Trp-Arg-Trp-Val-Arg-Arg |
| 7 | VVRVVRRVVRVVRR<br>Val-Val-Arg-Val-Val-Arg-Arg-Val-Val-Arg-Val-Val-Arg-Arg |
| 8 | VVRVVRVVRVVRVVRVVRV<br>Val-Val-Arg-Val-Val-Arg-Val-Val-Val-Arg-Val-Val-Arg-Val-Val-Val-Arg-Val-Val-Arg-Val |
| 9 | RSRVVRSWSRV<br>Arg-Ser-Arg-Val-Val-Arg-Ser-Trp-Ser-Arg-Val |
| 10 | RFVRRVRRFVRRVRRFVRRVRRFVRRVRRFVRRVR RFVRRVRRFVRRVRRFVRRVRRFVRRVRRFVRRVR RFVRRVRRFVRRVR<br>Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg-Arg-Phe-Val-Arg-Arg-Val-Arg |
| 11 | RRTYSRSRRTYSRSRRTYSR<br>Arg-Arg-Thr-Tyr-Ser-Arg-Ser-Arg-Arg-Thr-Tyr-Ser-Arg-Ser-Arg-Arg-Thr-Tyr-Ser-Arg |
| 12 | KVVSSIIEIISSVVKVVSSIIEIISSVV<br>Lys-Val-Val-Ser-Ser-Ile-Ile-Glu-Ile-Ile-Ser-Ser-Val-Val-Lys-Val-Val-Ser-Ser-Ile-Ile-Glu-Ile-Ile-Ser-Ser-Val-Val |
| 13 | KKTHTKTKKTHTKTKKTHTK<br>Lys-Lys-Thr-His-Thr-Lys-Thr-Lys-Lys-Thr-His-Thr-Lys-Thr-Lys-Lys-Thr-His-Thr-Lys |
| 14 | VVRVVRRVRVVRRVRVVRR<br>Val-Val-Arg-Val-Val-Arg-Arg-Val-Val-Arg-Val-Val-Arg-Arg-Val-Val-Arg-Val-Val-Arg-Arg |

TABLE 1-continued

Antimicrobial Peptides

| SEQ ID NO: | Amino Acid Sequence |
|---|---|
| 15 | RVVRVVRRVVRR<br>Arg-Val-Val-Arg-Val-Val-Arg-Arg-<br>Val-Val-Arg-Arg |
| 16 | RVVRVVRRWVRR<br>Arg-Val-Val-Arg-Val-Val-Arg-Arg-<br>Trp-Val-Arg-Arg |
| 17 | RWWRWWRRWWRR<br>Arg-Trp-Trp-Arg-Trp-Trp-Arg-Arg-<br>Trp-Trp-Arg-Arg |
| 18 | WRRWWRRWWRWWRRWWRR<br>Trp-Arg-Arg-Trp-Trp-Arg-Arg-Trp-<br>Trp-Arg-Trp-Trp-Arg-Arg-Trp-Trp-<br>Arg-Arg |
| 19 | RRVVRRVRRVVRRVVRVVRRVVRR<br>Arg-Arg-Val-Val-Arg-Arg-Val-Arg-<br>Arg-Val-Val-Arg-Arg-Val-Val-Arg-<br>Val-Val-Arg-Arg-Val-Val-Arg-Arg |
| 20 | RRWWRRWRRWWRRWWRWWRRWWRR<br>Arg-Arg-Trp-Trp-Arg-Arg-Trp-Arg-<br>Arg-Trp-Trp-Arg-Arg-Trp-Trp-Arg-<br>Trp-Trp-Arg-Arg-Trp-Trp-Arg-Arg |
| 21 | VRRVVRRVVRVVRRVVRRVRRVVRRVVRVVRRVVR<br>R<br>Val-Arg-Arg-Val-Val-Arg-Arg-Val-<br>Val-Arg-Val-Val-Arg-Arg-Val-Val-<br>Arg-Arg-Val-Arg-Arg-Val-Val-Arg-<br>Arg-Val-Val-Arg-Val-Val-Arg-Arg-<br>Val-Val-Arg-Arg |
| 22 | VRRVWRRVVRVVRRWVRRVRRVWRRVVRVVRRWVR<br>R<br>Val-Arg-Arg-Val-Trp-Arg-Arg-Val-<br>Val-Arg-Val-Val-Arg-Arg-Trp-Val-<br>Arg-Arg-Val-Arg-Arg-Val-Trp-Arg-<br>Arg-Val-Val-Arg-Val-Val-Arg-Arg-<br>Trp-Val-Arg-Arg |
| 23 | RRVVRRVRRVVRRVRVVRRVVRRVRRVVRRVVRV<br>VRRVVRR<br>Arg-Arg-Val-Val-Arg-Arg-Val-Arg-<br>Arg-Val-Val-Arg-Arg-Val-Arg-Val-<br>Val-Arg-Arg-Val-Val-Arg-Arg-Val-<br>Arg-Arg-Val-Val-Arg-Arg-Val-Val-<br>Val-Arg-Arg-Val-Val-Arg-Arg-Val-Val-<br>Arg-Arg |
| 24 | RVVRVVRRVVRRVRRVVRVVRRVVRRVRRVV<br>RRVVRVVRRVVRR<br>Arg-Val-Val-Arg-Val-Val-Arg-Arg-<br>Val-Val-Arg-Arg-Val-Arg-Arg-Val-<br>Val-Arg-Arg-Val-Val-Arg-Val-Val-<br>Arg-Arg-Val-Val-Arg-Arg-Val-Arg-<br>Arg-Val-Val-Arg-Arg-Val-Val-Arg-<br>Val-Val-Arg-Arg-Val-Val-Arg-Arg |
| 25 | RVVRVVRRWVRRVRRVWRRVVRVVRRWVRRVRRVW<br>RRVVRVVRRWRVV<br>Arg-Val-Val-Arg-Val-Val-Arg-Arg-<br>Trp-Val-Arg-Arg-Val-Arg-Arg-Val-<br>Trp-Arg-Arg-Val-Val-Arg-Val-Val-<br>Arg-Arg-Trp-Val-Arg-Arg-Val-Arg-<br>Arg-Val-Trp-Arg-Arg-Val-Val-Arg-<br>Val-Val-Arg-Arg-Trp-Arg-Val-Val |

In some embodiments, the peptide or pharmaceutically acceptable salt thereof as described herein comprises SEQ ID NO: 1. In some embodiments, the peptide or pharmaceutically acceptable salt thereof as described herein comprises SEQ ID NO: 2. In some embodiments, the peptide or pharmaceutically acceptable salt thereof as described herein comprises SEQ ID NO: 3. In some embodiments, the peptide or pharmaceutically acceptable salt thereof as described herein comprises SEQ ID NO: 4. In some embodiments, the peptide or pharmaceutically acceptable salt thereof as described herein comprises SEQ ID NO: 5. In some embodiments, the peptide or pharmaceutically acceptable salt thereof as described herein comprises SEQ ID NO: 6. In some embodiments, the peptide or pharmaceutically acceptable salt thereof as described herein comprises SEQ ID NO: 7. In some embodiments, the peptide or pharmaceutically acceptable salt thereof as described herein comprises SEQ ID NO: 8. In some embodiments, the peptide or pharmaceutically acceptable salt thereof as described herein comprises SEQ ID NO: 9. In some embodiments, the peptide or pharmaceutically acceptable salt thereof as described herein comprises SEQ ID NO: 10. In some embodiments, the peptide or pharmaceutically acceptable salt thereof as described herein comprises SEQ ID NO: 11. In some embodiments, the peptide or pharmaceutically acceptable salt thereof as described herein comprises SEQ ID NO: 12. In some embodiments, the peptide or pharmaceutically acceptable salt thereof as described herein comprises SEQ ID NO: 13. In some embodiments, the peptide or pharmaceutically acceptable salt thereof as described herein comprises SEQ ID NO: 14. In some embodiments, the peptide or pharmaceutically acceptable salt thereof as described herein comprises SEQ ID NO: 15. In some embodiments, the peptide or pharmaceutically acceptable salt thereof as described herein comprises SEQ ID NO: 16. In some embodiments, the peptide or pharmaceutically acceptable salt thereof as described herein comprises SEQ ID NO: 17. In some embodiments, the peptide or pharmaceutically acceptable salt thereof as described herein comprises SEQ ID NO: 18. In some embodiments, the peptide or pharmaceutically acceptable salt thereof as described herein comprises SEQ ID NO: 19. In some embodiments, the peptide or pharmaceutically acceptable salt thereof as described herein comprises SEQ ID NO: 20. In some embodiments, the peptide or pharmaceutically acceptable salt thereof as described herein comprises SEQ ID NO: 21. In some embodiments, the peptide or pharmaceutically acceptable salt thereof as described herein comprises SEQ ID NO: 22. In some embodiments, the peptide or pharmaceutically acceptable salt thereof as described herein comprises SEQ ID NO: 23. In some embodiments, the peptide or pharmaceutically acceptable salt thereof as described herein comprises SEQ ID NO: 24. In some embodiments, the peptide or pharmaceutically acceptable salt thereof as described herein comprises SEQ ID NO: 25.

In some embodiments, the peptide or pharmaceutically acceptable salt thereof has at least 70% sequence identify to a polypeptide sequence of SEQ ID NO: 1, at least 70% sequence identify to a polypeptide sequence of SEQ ID NO: 2, at least 70% sequence identify to a polypeptide sequence of SEQ ID NO: 3, at least 70% sequence identify to a polypeptide sequence of SEQ ID NO: 4, at least 70% sequence identify to a polypeptide sequence of SEQ ID NO: 5, at least 70% sequence identify to a polypeptide sequence of SEQ ID NO: 6, at least 70% sequence identify to a polypeptide sequence of SEQ ID NO: 7, at least 70% sequence identify to a polypeptide sequence of SEQ ID NO: 8, at least 70% sequence identify to a polypeptide sequence of SEQ ID NO: 9, at least 70% sequence identify to a polypeptide sequence of SEQ ID NO: 10, at least 70% sequence identify to a polypeptide sequence of SEQ ID NO:

11, at least 70% sequence identify to a polypeptide sequence of SEQ ID NO: 12, at least 70% sequence identify to a polypeptide sequence of SEQ ID NO: 13, at least 70% sequence identify to a polypeptide sequence of SEQ ID NO: 14, at least 70% sequence identify to a polypeptide sequence of SEQ ID NO: 15, at least 70% sequence identify to a polypeptide sequence of SEQ ID NO: 16, at least 70% sequence identify to a polypeptide sequence of SEQ ID NO: 17, at least 70% sequence identify to a polypeptide sequence of SEQ ID NO: 18, at least 70% sequence identify to a polypeptide sequence of SEQ ID NO: 19, at least 70% sequence identify to a polypeptide sequence of SEQ ID NO: 20, at least 70% sequence identify to a polypeptide sequence of SEQ ID NO: 21, at least 70% sequence identify to a polypeptide sequence of SEQ ID NO: 22, at least 70% sequence identify to a polypeptide sequence of SEQ ID NO: 23, at least 70% sequence identify to a polypeptide sequence of SEQ ID NO: 24, or at least 70% sequence identify to a polypeptide sequence of SEQ ID NO: 25. In some embodiments, the peptide or pharmaceutically acceptable salt thereof has at least 70%, 75%, 80%, 85%, 90%, 95%, or 99% sequence identify to a polypeptide sequence listed in Table 1 and any increments of percentage therebetween.

In some embodiments, the pharmaceutical formulation comprises at least one peptide described herein as listed in Table 1. In some embodiments, the pharmaceutical formulation comprises one or more peptides described herein as listed in Table 1. In some embodiments, the pharmaceutical formulation comprises two or more peptides described herein as listed in Table 1. In some embodiments, the pharmaceutical formulation comprises three or more peptides described herein as listed in Table 1. In some embodiments, the pharmaceutical formulation comprises four or more peptides described herein as listed in Table 1. In some embodiments, the pharmaceutical formulation comprises five or more peptides described herein as listed in Table 1. In some embodiments, the pharmaceutical formulation comprises six or more peptides described herein as listed in Table 1. In some embodiments, the pharmaceutical formulation comprises seven or more peptides described herein as listed in Table 1. In some embodiments, the pharmaceutical formulation comprises eight or more peptides described herein as listed in Table 1. In some embodiments, the pharmaceutical formulation comprises nine or more peptides described herein as listed in Table 1. In some embodiments, the pharmaceutical formulation comprises ten or more peptides described herein as listed in Table 1. In some embodiments, the pharmaceutical formulation comprises eleven or more peptides described herein as listed in Table 1. In some embodiments, the pharmaceutical formulation comprises twelve or more peptides described herein as listed in Table 1. In some embodiments, the pharmaceutical formulation comprises thirteen or more peptides described herein as listed in Table 1. In some embodiments, the pharmaceutical formulation comprises fourteen or more peptides described herein as listed in Table 1. In some embodiments, the pharmaceutical formulation comprises fifteen or more peptides described herein as listed in Table 1.

In some specific embodiments, a peptide or salt thereof can comprise from about 60% to about 70%, from about 60% to about 80%, from about 60% to about 90%, from about 60% to about 91%, from about 60% to about 95%, or from about 60% to about 100% homology to a LLP homolog sequence selected from the group consisting of:

(SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-Arg-Arg-Trp-Trp-Arg-Arg;

(SEQ ID NO: 19)
Arg-Arg-Val-Val-Arg-Arg-Val-Arg-Arg-Val-Val-Arg-Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg;

(SEQ ID NO: 22)
Val-Arg-Arg-Val-Trp-Arg-Arg-Val-Val-Arg-Val-Val-Arg-Arg-Trp-Val-Arg-Arg-Val-Arg-Arg-Val-Arg-Arg-Val-Trp-Arg-Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-Arg-Val-Val-Arg-Arg-Val-Val-Arg-Arg-Val-Val-Arg-Val-Val-Arg-Arg-Val-Arg-Arg-Val-Val-Arg-Val-Val-Arg-Arg-Val-Val-Arg-Arg;

(SEQ ID NO: 24)
Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg;
and (SEQ ID NO: 25)
Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Val-Val-Arg-Arg-Val-Arg-Arg-Val-Val-Arg-Val-Val-Arg-Arg-Trp-Arg-Val-Val-Arg-Arg-Trp-Arg-Val-Val-Arg-Arg-Trp-Arg-Val.

In some specific embodiments, a peptide can comprise about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% homology to a LLP homolog sequence selected from the group consisting of:

(SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-Arg-Arg-Trp-Trp-Arg-Arg;

(SEQ ID NO: 19)
Arg-Arg-Val-Val-Arg-Arg-Val-Arg-Val-Val-Arg-Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Arg-Val-Val-Arg-Val-Val-Arg-Arg;

(SEQ ID NO: 22)
Val-Arg-Arg-Val-Trp-Arg-Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg;

(SEQ ID NO: 24)
Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Arg;
and (SEQ ID NO: 25)
Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Arg-Val-Arg-Arg-Val-Arg-Arg-Val-Trp-Arg-Arg-Val-Val-Arg-Val-Val-Arg-Arg-Trp-Arg-Val-Val.

In some specific embodiments, a peptide or salt thereof can be of formula (SEQ ID NO: 15)
Arg-Val-Val-Arg-Val-Val-Arg-Arg-Val-Val-Arg-Arg;

(SEQ ID NO: 16)
Arg-Val-Val-Arg-Val-Val-Arg-Arg-Trp-Val-Arg-Arg;

(SEQ ID NO: 17)
Arg-Trp-Trp-Arg-Trp-Trp-Arg-Arg-Trp-Trp-Arg-Arg;

(SEQ ID NO: 18)
Trp-Arg-Arg-Trp-Trp-Arg-Arg-Trp-Trp-Arg-Trp-Trp-Arg-Arg-Trp-Trp-Arg-Arg;

(SEQ ID NO: 19)
Arg-Arg-Val-Val-Arg-Arg-Val-Arg-Arg-Val-Val-Arg-Arg-Val-Val-Arg-Val-Val-Arg-Arg-Val-Val-Arg-Arg;

(SEQ ID NO: 1)
Arg-Arg-Trp-Val-Arg-Arg-Val-Arg-Arg-Val-Trp-Arg-Arg-Val-Val-Arg-Val-Val-Arg-Arg-Trp-Val-Arg-Arg;

(SEQ ID NO: 20)
Arg-Arg-Trp-Trp-Arg-Arg-Trp-Arg-Arg-Trp-Trp-Arg-Arg-Trp-Trp-Arg-Trp-Trp-Arg-Arg-Trp-Trp-Arg-Arg;

(SEQ ID NO: 21)
Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Arg-Val-Val-Arg-Val-Val-Arg-Arg;

(SEQ ID NO: 22)
Val-Arg-Arg-Val-Trp-Arg-Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Arg;

(SEQ ID NO: 23)
Arg-Arg-Val-Val-Arg-Arg-Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg;

(SEQ ID NO: 24)
Arg-Val-Val-Arg-Val-Val-Arg-Arg-Val-Val-Arg-Arg-Val-Arg-Arg-Val-Val-Arg-Arg-Val-Val-Arg-Val-Val-Arg-Arg-Val-Val-Arg-Arg-Val-Arg-Arg-Val-Val-Arg-Arg-Val-Val-Arg-Arg;
or (SEQ ID NO: 25)
Arg-Val-Val-Arg-Val-Val-Arg-Arg-Trp-Val-Arg-Arg-Val-Arg-Arg-Val-Trp-Arg-Arg-Val-Val-Arg-Val-Val-Arg-Arg-Trp-Val-Arg-Arg-Val-Arg-Arg-Val-Arg-Arg-Val-Trp-Arg-Arg-Val-Val-Arg-Val-Val-Arg-Arg-Trp-Arg-Val-Val;

and can comprise at least one Arg, Val, or Trp in a D-configuration.

A peptide disclosed herein can be a salt thereof. In some embodiments, recitation of the phrases "peptide" or "polypeptide" should be construed to include a salt thereof even if not explicitly recited. In some embodiments, a salt can include a carboxylate salt (e.g. formate, acetate, trifluoroacetate, trichloroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, pamoate, nicotinate, isonicotinate, cinnamate, oxalate, malonate, succinate, suberate, sebacate, fumarate, malate, maleate, hydroxymaleate, hippurate, phthalate or a terephthalate salts); a halide salt (e.g. chloride, bromide or iodide salts); a sulfonate salt (e.g. benzene sulfonate, methyl-, bromo- or chloro-benzenesulfonate, xylenesulfonate, methanesulfonate, trifluoromethanesulfonate, ethanesulfonate, propanesulfonate, hydroxyethanesulfonate, 1- or 2-naphthalene-sulfonate or 1,5-naphthalenedisulfonate salts); a sulfate salt; a pyrosulfate salt; a bisulfate salt; a sulfite salt; a bisulfite salt; a phosphate salt; a monohydrogenphosphate salt; a dihydrogenphosphate salt; a metaphosphate salt; a pyrophosphate salt; a nitrate salt; and the like.

In some embodiments, amino acids of the peptides described herein can be L-amino acids. In some embodiments, amino acids of the peptides described herein can be D-amino acids. In some embodiments, the peptides can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 D-amino acids and the rest are L-amino acids within the peptide sequence. In some embodiments, the peptides can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 L-amino acids and the rest are D-amino acids within the peptide sequence.

In some embodiments, a peptide can be formulated with one or more pharmaceutically acceptable salts. In some embodiments, a pharmaceutically acceptable salt can be a salt described in Monkhouse, D. C., et al. "Pharmaceutical Salts." *J. Pharm. Sci* 66.1 (1977): 1-19. In some embodiments, a pharmaceutically acceptable salts can include those salts prepared by reaction of a peptide with a mineral, organic acid or inorganic base, such salts including, acetate, acrylate, adipate, alginate, aspartate, benzoate, benzenesulfonate, bisulfate, bisulfite, bitartrate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, 7-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undeconate and xylenesulfonate.

In some embodiments, a peptide can be formulated as a cleavable prodrug. The term "prodrug" as used herein, can refer to a drug precursor that, following administration to a subject and subsequent absorption, can be converted to an active, or a more active species via some process, such as conversion by a metabolic pathway. Thus, the term can encompass a derivative, which, upon administration to a recipient, can be capable of providing, either directly or indirectly, a peptide, pharmaceutically acceptable salt or a metabolite or residue thereof. Some prodrugs can have a chemical group present on a prodrug that renders it less active and/or confers solubility or some other property to the drug. Once the chemical group has been cleaved and/or modified from the prodrug the active drug can be generated. a prodrugs can be a prodrug that can increase the bioavailability of a peptide when administered to a subject (e.g. by allowing an administered peptide to be more readily absorbed) or which enhance delivery of the peptide to a biological compartment (e.g. the brain or lymphatic system).

WASH

A pharmaceutical formulation as described herein can be present as a wash. A wash can be a liquid formulation containing a peptide that can display antimicrobial activity as described herein. In some cases, a wash can be a coating that can be applied and can remain on an article.

A washing method can include an incision to open a site of infection. After an incision, a wash can be applied to the open site to treat or prevent infection. In some cases, a wash method can include irrigation of an open site with a wash. In some cases, a wash method can include drainage of an open site before, during, or after contacting the open site with a wash.

In some cases, a wash can be different than a coating. In some embodiments, a wash is contacted with an article, but does not remain associated or attached to the article after, for example, rinsing with an aqueous buffer. A wash can contain a diluent such as water, glycerol, methanol, ethanol, and other similar biocompatible diluents. In some cases, a diluent can be an aqueous acid such as acetic acid, citric acid, maleic acid, hydrochloric acid, phosphoric acid, nitric acid, sulfuric acid, or similar. In some instances, a diluent can be used to titrate a pH of a peptide to a pH such as physiological pH to produce a salt as described above. In other cases, a diluent can be selected from a group comprising alkaline metal carbonates such as calcium carbonate; alkaline metal phosphates such as calcium phosphate; alkaline metal sulfates such as calcium sulfate; cellulose derivatives such as cellulose, microcrystalline cellulose, cellulose acetate; magnesium oxide, dextrin, fructose, dextrose, glyceryl palmitostearate, lactitol, caoline, lactose, maltose, mannitol, simethicone, sorbitol, starch, pregelatinized starch, talc, xylitol and/or anhydrates, hydrates and/or pharmaceutically acceptable derivatives thereof or combinations thereof.

In some cases, a wash can contain other agents. Such agents can have an additive effect with an active agent such as a peptide as described herein. In some cases, the effect can be a synergistic effect between a peptide and an additional agent. For example, a compound such as a biofilm disruptor as described herein may provide enhanced activity of a peptide due to the synergistic effect of partial biofilm disruption.

Additional agents can include an antibiotic such as Ceftobiprole, Ceftaroline, Clindamycin, Dalbavancin, Daptomycin, Linezolid, Mupirocin, Oritavancin, Tedizolid, Telavancin, Tigecycline, Vancomycin, an Aminoglycoside, a Carbapenem, Ceftazidime, Cefepime, Ceftobiprole, a Fluoroquinolone, Piperacillin, Ticarcillin, Linezolid, a Streptogramin, Tigecycline, Daptomycin, or a salt of any of these; an antiviral compound such as Acyclovir, Brivudine, Docosanol, Famciclovir, Idoxuridine, Penciclovir, Trifluridine, Valacyclovir, Amantadine, Rimantadine, a neuraminidase inhibitor, Oseltamivir, Zanamivir, or a salt of any of these; an antifungal agent such as antifungal agents such as ciclopirox olamine, haloprogin, tolnaftate, undecylenate, topical nysatin, amorolfine, butenafine, naftifine, terbinafine; a surfactant such as polyoxyethylene sorbitan fatty acid esters (polysorbates), sodium lauryl sulphate, sodium stearyl fumarate, polyoxyethylene alkyl ethers, sorbitan fatty acid esters, polyethylene glycols (PEG), polyoxyethylene castor oil derivatives, docusate sodium, sugar esters of fatty acids, and glycerides of fatty acids; a quaternary ammonium compound such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; small molecules such as imidazole, indoles, nitric oxide, triazoles, phenols, sulfides, polysaccharides, furanones, and bromopyrroles; amino acids and their derivatives such as L-leucine, cysteamine, and additional peptides described herein. In some cases, an additional agent can be curcumin, apple cider vinegar, oregano, garlic, berberine, activated charcoal, or a proteolytic enzyme.

In some cases, a wash can be present in the form of a hydrogel. A hydrogel can include a carbomer; hyaluronic acid, a poloxamer; sodium carboxymethylcellulose, a polysaccharide, agar, starch, gelatin, acrylamide, agarose, acrylic acid, bisacrylamide, poly(acrylic acid), poly(vinyl alcohol), poly(vinylpyrrolidone), poly(ethylene glycol), poly(vinyl pyrrolidone), poly(methyl vinyl ether-alt-maleic anhydride), carboxymethylcellulose, pectin, an elastomer, an adhesive, and salts of any of these.

Pharmaceutically Acceptable Excipients

At least one peptide disclosed herein can be formulated as a pharmaceutical formulation. In some embodiments, a pharmaceutical formulation can comprise a peptide described herein and at least one excipient. By "pharmaceutically acceptable", it is meant that the carrier, diluent, or excipient must be compatible with the other ingredients of the formulation and not deleterious to the recipient thereof. The term "compatible", as used herein, means that the components of the formulation are capable of being commingled with the subject compound, and with each other, in a manner such that there is no interaction that would substantially reduce the pharmaceutical efficacy of the formulation under ordinary use situations.

In some embodiments, a pharmaceutical formulation can comprise an excipient. An excipient can be an excipient described in the Handbook of Pharmaceutical Excipients, American Pharmaceutical Association (1986).

Non-limiting examples of suitable excipients can include a buffering agent, a preservative, a stabilizer, a binder, a compaction agent, a lubricant, a chelator, a dispersion enhancer, a disintegration agent, a flavoring agent, a sweetener, and/or a coloring agent. In some embodiments, the pharmaceutical formulation further comprises one or more additional pharmaceutically acceptable excipients. See, e.g., *Remington: The Science and Practice of Pharmacy* (Gennaro, 21$^{st}$ Ed. Mack Pub. Co., Easton, PA (2005) for a list of pharmaceutically acceptable excipients. In some embodiments, the pharmaceutically acceptable excipient is of sufficiently high purity and sufficiently low toxicity to render them suitable for administration preferably to an animal, preferably a mammal, being treated.

In some embodiments, an excipient can comprise a preservative. Non-limiting examples of suitable preservatives can include antioxidants, such as alpha-tocopherol and ascorbate, and antimicrobials, such as parabens, chlorobutanol, and phenol. Antioxidants can further include but not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some embodiments a preservatives can include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments, an excipient can comprise a binder. Non-limiting examples of suitable binders can include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. The binders that can be used in a pharmaceutical formulation can be selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or a combination thereof.

In some embodiments, an excipient can comprise a lubricant. Non-limiting examples of suitable lubricants can include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that can be used in a pharmaceutical formulation can be selected from metallic stearates (such as magnesium stearate, calcium stearate, aluminum stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments, an excipient can comprise a dispersion enhancer. Non-limiting examples of suitable dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, an excipient can comprise a disintegrant. In some embodiments a disintegrant can be a non-effervescent disintegrant. Non-limiting examples of suitable non-effervescent disintegrants can include starches such as corn starch, potato starch, pregelatinized and modified starches thereof, sweeteners, and clays, such as bentonite, micro-crystalline cellulose, alginates, sodium starch glycolate, gums such as agar, guar, locust bean, karaya, pecitin, and tragacanth. In some embodiments a disintegrant can be an effervescent disintegrant. Non-limiting examples of suitable effervescent disintegrants can include sodium bicarbonate in combination with citric acid, and sodium bicarbonate in combination with tartaric acid.

In some embodiments, an excipient can comprise a flavoring agent. Flavoring agents incorporated into an outer layer can be chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; *eucalyptus*; vanilla; citrus oil such as lemon oil, orange oil, grape and grapefruit oil; and fruit essences including apple, peach, pear, strawberry, raspberry, cherry, plum, pineapple, and apricot.

In some embodiments, an excipient can comprise a sweetener. Non-limiting examples of suitable sweeteners can include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like. In some embodiments, the excipient may be a sugar. Non-limiting examples of suitable sugars can include glucose, sucrose, dextrose, lactose, maltodextrin, fructose, and mixtures thereof.

In some embodiments, an excipient can comprise a coloring agent. Non-limiting examples of suitable color agents can include food, drug and cosmetic colors (FD&C), drug and cosmetic colors (D&C), and external drug and cosmetic colors (Ext. D&C). A coloring agent can be used as dyes.

In some embodiments, an excipient can comprise an isotonicity agent. Examples can include, but are not limited to: sodium chloride, calcium chloride, potassium chloride, sodium lactate, copper chloride, copper sulfate, monopotassium phosphate, sucrose, dextrose, or glucose. In some embodiments, the isotonicity agent is sodium chloride.

In some embodiments, an excipient can comprise a chelator. In some embodiments, a chelator can be a fungicidal chelator. Examples can include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis (2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl) ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris (methylenephosphoric acid); 7,19,30-trioxa-1,4,10,13,16, 22,27,33-octaazabicyclo[11,11,11] pentatriacontane hexahydrobromide; or triethylenetetramine-N,N,N',N'',N'',N''-hexaacetic acid.

In some embodiments, an excipient can comprise a diluent. Non-limiting examples of diluents can include water, glycerol, methanol, ethanol, and other similar biocompatible diluents. In some embodiments, a diluent can be an aqueous acid such as acetic acid, citric acid, maleic acid, hydrochloric acid, phosphoric acid, nitric acid, sulfuric acid, or similar. In other cases, a diluent can be selected from a group comprising alkaline metal carbonates such as calcium carbonate; alkaline metal phosphates such as calcium phosphate; alkaline metal sulphates such as calcium sulphate; cellulose derivatives such as cellulose, microcrystalline cellulose, cellulose acetate; magnesium oxide, dextrin, fructose, dextrose, glyceryl palmitostearate, lactitol, caoline, lactose, maltose, mannitol, simethicone, sorbitol, starch, pregelatinized starch, talc, xylitol and/or anhydrates, hydrates and/or pharmaceutically acceptable derivatives thereof or combinations thereof.

In other embodiments, an excipient can comprise a surfactant. Surfactants can be selected from, but not limited to, polyoxyethylene sorbitan fatty acid esters (polysorbates), sodium lauryl sulphate, sodium stearyl fumarate, polyoxyethylene alkyl ethers, sorbitan fatty acid esters, polyethylene glycols (PEG), polyoxyethylene castor oil derivatives, docusate sodium, quaternary ammonium compounds, amino acids such as L-leucine, sugar esters of fatty acids, glycerides of fatty acids or a combination thereof.

In some embodiments, an excipient can comprise an aqueous carrier.

In some embodiments, the pharmaceutical formulation is in the form of a tablet, a liquid, a syrup, an oral formulation, an intravenous formulation, an intranasal formulation, an ocular formulation, an otic formulation, a subcutaneous formulation, an inhalable respiratory formulation, a suppository, and any combination thereof. A weight fraction of an excipient or combination of excipients in a pharmaceutical formulation can be less than about 80%, 70%, 60%, 50%, 45%, 40%, 35%, 30%, 25%, 20%, 15%, 10%, 5%, 4%, 3%, 2%, or 1% as compared to a total weight of a pharmaceutical formulation. See, e.g., *Remington: The Science and Practice of Pharmacy* (Gennaro, 21$^{st}$ Ed. Mack Pub. Co., Easton, PA (2005).

Methods of Treatment

A peptide disclosed herein, salt thereof, or a composition containing a peptide or salt thereof can be administered to a subject in order to at least partially ameliorate a disease or condition. A subject can be in need of a treatment of a disease or condition. In some cases, a subject may have been previously diagnosed with a disease or condition described herein, and/or may be at risk of developing a disease or condition as described herein.

As previously discussed, a peptide disclosed herein, salt thereof, or a composition containing a peptide or salt thereof can be engineered to provide a therapeutic effect by disruption of integrity of a membrane of a target. This disruption of structural integrity can occur through (a) binding to a negatively charged surface on a membrane; and/or (b) integrating into a membrane. The ability of a peptide to bind to a negatively charged surface on a membrane and/or integrate into a membrane can allow a peptide to act as a toxic agent through disruption of membrane integrity.

Administration

A pharmaceutical formulation disclosed herein can be formulated into a variety of forms and administered by a number of different means. A pharmaceutical formulation can be administered orally, rectally, or parenterally, in formulations containing conventionally acceptable carriers, adjuvants, and vehicles as desired. The term "parenteral" as used herein can include subcutaneous, intravenous, intramuscular, or intrasternal injection and infusion techniques. Administration can include injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), transdermal, transmucosal, sublingual, buccal and topical (including epicutaneous, dermal, enema, eye drops, ear drops, intranasal, vaginal) administration. In some exemplary embodiments, a route of administration can be via an injection such as an intramuscular, intravenous, subcutaneous, or intraperitoneal injection.

Solid dosage forms for oral administration can include capsules, tablets, caplets, pills, troches, lozenges, powders, and granules. A capsule can comprise a core material comprising a nutritive protein or formulation and a shell wall that encapsulates a core material. In some embodiments a core material can comprise at least one of a solid, a liquid, and an emulsion. In some embodiments a shell wall material can comprise at least one of a soft gelatin, a hard gelatin, and a polymer. Suitable polymers can include but not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer can function as taste-masking agents. Tablets, pills, and the like can be compressed, multiply compressed, multiply layered, and/or coated. A coating can be single or multiple. In some embodiments, a coating material can comprise at least one of a saccharide, a polysaccharide, and glycoproteins extracted from at least one of a plant, a fungus, and a microbe. Non-limiting examples can include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments a coating material can comprise a protein. In some embodiments, a coating material can comprise at least one of a fat and/or an oil. In some embodiments the at least one of a fat and/or an oil can be high temperature melting. In some embodiments the at least one of a fat and/or an oil can be hydrogenated or partially hydrogenated. In some embodiments the at least one of a fat and/or an oil can be derived from a plant. In some embodiments the at least one of a fat and/or an oil can comprise at least one of glycerides, free fatty acids, and fatty acid esters. In some embodiments a coating material can comprise at least one edible wax. An edible wax can be derived from animals, insects, or plants. Non-limiting examples can include beeswax, lanolin, bayberry wax, carnauba wax, and rice bran wax. Tablets and pills can additionally be prepared with enteric coatings. In some embodiments, a tablet, pill, and the like can be formulated for an extended release profile.

In some embodiments, a peptide described herein or pharmaceutically acceptable salt thereof can be administered in a formulation for topical administration. For topical administration, an active agent may be formulated as is known in the art for direct application to a target area. Forms chiefly conditioned for topical application can take the form, for example, of creams, milks, gels, powders, dispersion or microemulsions, lotions thickened to a greater or lesser extent, impregnated pads, ointments or sticks, soaps, detergents, lotions or cakes of soap. Other conventional forms for this purpose include wound dressings, coated bandages or other polymer coverings, ointments, creams, lotions, pastes, jellies. Thus, a therapeutic peptide disclosed herein can be delivered via patches or bandages for dermal administration. Alternatively, a peptide can be formulated to be part of an adhesive polymer, such as polyacrylate or acrylate/vinyl acetate copolymer. For long-term applications it might be desirable to use microporous and/or breathable backing laminates, so hydration or maceration of a skin can be minimized. A backing layer can be any appropriate thickness that will provide a desired protective and support functions. A suitable thickness will generally be from about 1 to about 1000 microns. For example, from about 10 to about 300 microns. Topical administration may be in the form of a nail coating or lacquer. For example, an antifungal peptide can be formulated in a solution for topical administration that contains ethyl acetate (NF), isopropyl alcohol (USP), and butyl monoester of poly[methylvinyl ether/maleic acid] in isopropyl alcohol. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Liquid formulations can include a syrup (for example, an oral formulation), an intravenous formulation, an intranasal formulation, an ocular formulation (e.g. for treating an eye infection), an otic formulation (e.g. for treating an ear infection), an ointment, a cream, an aerosol, and the like. In some embodiments, a combination of various formulations can be administered.

Drops, such as eye drops or nose drops, may be formulated with one or more peptide(s) in an aqueous or non-aqueous base also comprising one or more dispersing agents, solubilizing agents or suspending agents. Drops can be delivered via a simple eye dropper-capped bottle, via a plastic bottle adapted to deliver liquid contents drop-wise, or via a specially shaped closure.

In some embodiments, the method of administration may last over a course of at least about 1 hour, 5 hours, 12 hours, 24 hours, 48 hours, 72 hours, 4 days, 5 days, 1 week, 2 weeks, 3 week, 4 weeks, 2 months, 3 months, 4 months, 5 months, 6 months, 7 months, 8 months, 9 months, 10 months, 11 months, 12 months, 2 years, 3 years, 4 years, 5 years, 6 years, 7 years, 8 years, 9 years, 10 years, 20 years, 25 years, 30 years, 35 years, 40 years, 45 years, 50 years, 55 years, 60 years, 65 years, 70 years, 75 years, or 80 years.

Administration of a peptide, pharmaceutically acceptable salt thereof, or a formulation comprising a peptide or salt thereof to a subject can be used to at least partially ameliorate a bacterial infection in a subject. Administration of a peptide, pharmaceutically acceptable, or formulation can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. In some embodiments, a treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

Administration of a peptide, pharmaceutically acceptable, or formulation can be performed at least 1, 2, 3, 4, 5, 6, 7, 8, 9, 10, 11, 12, 13, 14, 15, 16, 17, 18, 19, 20, 21, 22, 23, or 24 times a day. In some embodiments, administration of a peptide, pharmaceutically acceptable, or formulation can be performed at least 1, 2, 3, 4, 5, 6, 7, 8, 9, 10, 11, 12, 13, 14, 15, 16, 17, 18, 19, 20, or 21 times a week. In some embodiments, administration of a peptide, pharmaceutically acceptable, or formulation can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

In some embodiments, administration of the pharmaceutical formulation comprising a peptide or pharmaceutically acceptable salt occurs over a time period of from at least about 0.5 min to at least about 1 min, from at least about 1 min to at least about 2 min, from at least about 2 min to at least about 3 min, from at least about 3 min to at least about 4 min, from at least about 4 min to at least about 5 min, from at least about 5 min to at least about 6 min, from at least about 6 min to at least about 7 min, from at least about 7 min to at least about 8 min, from at least about 8 min to at least about 9 min, from at least about 9 min to at least about 10 min, from at least about 10 min to at least about 11 min, from at least about 11 min to at least about 12 min, from at least about 12 min to at least about 13 min, from at least about 13 min to at least about 14 min, from at least about 14 min to at least about 15 min, from at least about 15 min to at least about 16 min, from at least about 16 min to at least about 17 min, from at least about 17 min to at least about 18 min, from at least about 18 min to at least about 19 min, from at least about 19 min to at least about 20 min, from at least about 20 min to at least about 21 min, from at least about 21 min to at least about 22 min, from at least about 22 min to at least about 23 min, from at least about 23 min to at least about 24 min, from at least about 24 min to at least about 25 min, from at least about 25 min to at least about 26 min, from at least about 26 min to at least about 27 min, from at least about 27 min to at least about 28 min, from at least about 28 min to at least about 29 min, or from at least about 29 min to at least about 30 min.

A peptide disclosed herein, salt thereof, or a formulation containing a peptide or salt thereof can be administered to a subject in order to at least partially ameliorate a disease or condition. A subject can be in need of a treatment of a disease or condition. In some embodiments, a subject may have been previously diagnosed with a disease or condition described herein, and/or may be at risk of developing a disease or condition as described herein.

Coatings

Also disclosed herein are methods of producing a coating comprising a peptide disclosed herein, salt thereof, or a composition containing a peptide or salt thereof. A coating can be an antimicrobial coating that can be applied to a surface to remove contaminants from a surface, or to prevent contamination in the first instance. A coating can comprise an antimicrobial peptide disclosed herein. A coating can generally be prepared by contacting a coating material with a peptide disclosed herein, salt thereof, or a composition containing a peptide or salt thereof.

In some cases, a coating can be in the form of a film, sheet, liquid, or aerosol used to coat a biological or non-biological surface. A film can be prepared by coating material capable of producing a film with a peptide disclosed herein, salt thereof, or a composition containing a peptide or salt thereof. A coating material capable of producing a film can be an adhesive compound, such as a mucoadhesive, used to bind a compound to a biological surface. An exemplary mucoadhesive can be a highly negatively charged polymer such as polycarbophil. A coating material capable of producing a film can be adhered to a biological surface to treat or prevent an infection on a biological surface. For example, a peptide described herein can be formulated as a coating for adherence onto an open wound, thereby eliminating a need for a bandage by directly adhering an antimicrobial compound to a site of action. Further applications can include adhering a coating onto a transplanted organ to prevent infection by a pathogen during a transplant process.

In some cases, a coating can comprise a peptide disclosed herein, salt thereof, or a composition containing a peptide or salt thereof can be used to sterilize a surface. For example, a coating can be applied to surgical equipment, and any surface in contact with surgical equipment, prior to an operation. Such practice can mitigate a risk contamination of the surgical equipment during transport. Scientific equipment can also be coated with such a coating to prevent cross contamination of certain microbes that could interfere with a measurement to be taken with the equipment.

In some cases, a peptide can be the sole antimicrobial compound in a coating. In other instances, a coating can comprise other antimicrobial compounds such as those described herein. Metallic antimicrobial compounds such as silver nitrate can also be used in combination with a peptide scribed herein.

Further examples of the use of a coating containing a peptide described herein can include coating an article such as a medical device. In some cases, the medical device can be an implantable medical device. For example, a medical device such as a catheter or prosthetic limb can be coated with a coating as described above to prevent contamination during packaging, storage, or during a transplant operation.

An exemplary application of a coating as described herein can include coating of an implantable prosthetic. An "implantable prosthetic" can include a medical device manufactured to replace a missing biological structure, support a damaged biological structure, or enhance an existing biological structure. An implantable prosthetic can include, for example, sensory/neurological, cardiovascular, orthopedic, contraceptive, cosmetic, gastrointestinal, respiratory, and urological devices. Examples of such devices can include an intraocular lens, an intrastromal corneal ring segment; a cochlear implant; a tympanostomy tube; a neurostimulator; an artificial heart; an artificial heart valve; an implantable cardioverter-defibrillator; a cardiac pacemaker; a coronary stent; a variety of pins, rods, screws, or plates that can provide structural support; an intrauterine device; a breast implant; a nose prosthesis; an ocular prosthesis; an injectable filler; an implantable gastric stimulator; a diaphragmatic/phrenic nerve stimulator; a neurostimulator; a surgical mesh; a penile prosthesis; a replacement hip joint;

a replacement knee joint; a replacement shoulder joint; a replacement finger or toe joint; a replacement elbow joint; and the like.

A prosthetic can be a portion of a joint or limb, and can include pins, rods, screws, or plates suitable to reconstruct a joint or limb. In some cases, a prosthetic can be a partial reconstruction of a joint or limb. In some cases, a prosthetic can be a complete reconstruction of a joint of limb.

In some cases, an implantable prosthetic can be used to treat or prevent a disease or condition. Examples can include a cataract, glaucoma, a keratoconus, a visual impairment, otosclerosis, hearing loss, otitis media, epilepsy, Parkinson's disease, treatment-resistant depression, heart failure, cardiac arrhythmia, ventricular tachycardia, valvular heart disease, angina pectoris, atherosclerosis, a bone fracture, osteoarthritis, rheumatoid arthritis, avascular necrosis (AVN) or osteonecrosis (ON), congenital dislocation of the hip joint (CDH), hip dysplasia, acetabular dysplasia (shallow hip socket), frozen shoulder, loose shoulder, traumatized and malaligned joint, joint stiffness, scoliosis, spinal stenosis, chronic pain, unintended pregnancy, menorrhagia, skin trauma, gastroesophageal reflux disease, gastroparesis, respiratory failure, sleep apnea, urinary and fecal incontinence, and erectile dysfunction. In some cases, reconstruction or arthroplasty of a joint or other skeletal structure can be performed. Arthroplasty can include total or partial reconstruction. Examples of arthroplasty can include shoulder, hip, knee, ankle, finger, or other joints.

An article for implant such as an implantable prosthetic in contact with a coating containing a peptide, salt thereof, or pharmaceutical composition can be assembled as a composition containing an article and coating. An article such as an implantable prosthetic can be coated with a peptide, salt thereof, or pharmaceutical composition as described herein to obviate or minimize a risk of infection when the article is inserted into an animal such as a human. Alternatively, an article can be washed with a wash solution containing a debriding or disinfecting agent prior to insertion. In some cases, the wash can be a pharmaceutical formulation containing a peptide described herein.

Dosage

In some embodiments, the pharmaceutical formulations described herein is in the form of a unit dose. In some embodiments, a pharmaceutical formulation can be formulated to optimize pharmacokinetics/pharmacodynamics of a peptide or salt thereof contained therein.

In some embodiments, a peptide, pharmaceutically acceptable salt thereof, or pharmaceutical formulation comprising a peptide or salt thereof described herein can be administered at a dose of from about 1 milligram (mg) to about 1000 mg, from about 5 mg to about 1000 mg, from about 10 mg to about 1000 mg, from about 15 mg to about 1000 mg, from about 20 mg to about 1000 mg, from about 25 mg to about 1000 mg, from about 30 mg to about 1000 mg, from about 35 mg to about 1000 mg, from about 40 mg to about 1000 mg, from about 45 mg to about 1000 mg, from about 50 mg to about 1000 mg, from about 55 mg to about 1000 mg, from about 60 mg to about 1000 mg, from about 65 mg to about 1000 mg, from about 70 mg to about 1000 mg, from about 75 mg to about 1000 mg, from about 80 mg to about 1000 mg, from about 85 mg to about 1000 mg, from about 90 mg to about 1000 mg, from about 95 mg to about 1000 mg, from about 100 mg to about 1000 mg, from about 150 mg to about 1000 mg, from about 200 mg to about 1000 mg, from about 250 mg to about 1000 mg, from about 300 mg to about 1000 mg, from about 350 mg to about 1000 mg, from about 400 mg to about 1000 mg, from about 450 mg to about 1000 mg, from about 500 mg to about 1000 mg, from about 550 mg to about 1000 mg, from about 600 mg to about 1000 mg, from about 650 mg to about 1000 mg, from about 700 mg to about 1000 mg, from about 750 mg to about 1000 mg, from about 800 mg to about 1000 mg, from about 850 mg to about 1000 mg, from about 900 mg to about 1000 mg, or from about 950 mg to about 1000 mg.

In some embodiments, a peptide, pharmaceutically acceptable salt thereof, or pharmaceutical formulation comprising a peptide or salt thereof described herein can be administered at a dose of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 180, 181, 182, 183, 184, 184, 186, 187, 188, 189, 190, 191, 192, 193, 194, 195, 196, 197, 198, 199,200, 210,220, 230, 240, 250, 260, 270, 280, 290, 300, 310, 320, 330, 340, 350, 360, 370, 380, 390,400, 410,420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg.

In some embodiments, pharmaceutical formulation comprising a peptide or pharmaceutically acceptable salt is present at a concentration from at least about 0.01 micrograms per milliliter (µg/mL) to at least about 100 milligrams per milliliter (mg/mL). In some embodiments, the peptide or pharmaceutically acceptable salt is present at a concentration from at least about at least about 0.1 mg/mL to at least about 5 mg/mL. In some embodiments, the peptide or pharmaceutically acceptable salt is present at a concentration from at least about at least about 0.5 mg/mL to at least about 1 mg/mL. In some embodiments, the peptide or pharmaceutically acceptable salt is present at a concentration about 1 mg/mL. In some embodiments, the peptide or pharmaceutically acceptable salt is present at a concentration about 2 mg/mL. In some embodiments, the peptide or pharmaceutically acceptable salt is present at a concentration about 3 mg/mL. In some embodiments, the peptide or pharmaceutically acceptable salt is present at a concentration about 4 mg/mL. In some embodiments, the peptide or pharmaceutically acceptable salt is present at a concentration about 5 mg/mL. In some embodiments, the peptide or pharmaceutically acceptable salt is present at a concentration about 6 mg/mL. In some embodiments, the peptide or pharmaceutically acceptable salt is present at a concentration about 7 mg/mL. In some embodiments, the peptide or pharmaceutically acceptable salt is present at a concentration about 8 mg/mL. In some embodiments, the peptide or pharmaceutically acceptable salt is present at a concentration about 9 mg/mL. In some embodiments, the peptide or pharmaceutically acceptable salt is present at a concentration about 10 mg/mL. In some embodiments, the peptide or pharmaceutically acceptable salt is present at a concentration about 20 mg/mL. In some embodiments, the peptide or pharmaceutically acceptable salt is present at a concentration about 30 mg/mL. In some embodiments, the peptide or pharmaceutically acceptable salt is present at a concentration about 40 mg/mL. In some embodiments, the peptide or pharmaceutically acceptable salt is present at a concentration about 50 mg/mL. In some embodiments, the peptide or pharmaceutically acceptable salt is present at a concentration about 60 mg/mL. In some embodiments, the peptide or pharmaceutically acceptable salt is present at a concentration about 70 mg/mL. In some embodiments, the peptide or pharmaceutically acceptable salt is present at a concentration about 80 mg/mL. In some embodiments, the peptide or pharmaceutically acceptable salt is present at a concentration about 90 mg/mL. In some embodiments, the peptide or pharmaceutically acceptable salt is present at a concentration about 100 mg/mL.

In some embodiments, pharmaceutical formulation comprising a peptide or pharmaceutically acceptable salt can exhibit antimicrobial activity against an infection at a concentration from at least about 0.01 µg/mL to at least about 0.02 µg/mL, from at least about 0.02 µg/mL to at least about 0.03 µg/mL, from at least about 0.03 µg/mL to at least about 0.04 µg/mL, from at least about 0.04 µg/mL to at least about 0.05 µg/mL, from at least about 0.05 µg/mL to at least about 0.06 µg/mL, from at least about 0.06 µg/mL to at least about 0.07 µg/mL, from at least about 0.07 µg/mL to at least about 0.08 µg/mL, from at least about 0.08 µg/mL to at least about 0.09 µg/mL, from at least about 0.09 µg/mL to at least about 0.1 µg/mL, from at least about 0.1 µg/mL to at least about 0.2 µg/mL, from at least about 0.2 µg/mL to at least about 0.3 µg/mL, from at least about 0.3 µg/mL to at least about 0.4 µg/mL, from at least about 0.4 µg/mL to at least about 0.5 µg/mL, from at least about 0.5 µg/mL to at least about 0.6 µg/mL, from at least about 0.6 µg/mL to at least about 0.7 µg/mL, from at least about 0.7 µg/mL to at least about 0.8 µg/mL, from at least about 0.8 µg/mL to at least about 0.9 µg/mL, from at least about 0.9 µg/mL to at least about 1 µg/mL, from at least about 1 µg/mL to at least about 2 µg/mL, from at least about 2 µg/mL to at least about 3 µg/mL, from at least about 3 µg/mL to at least about 4 µg/mL, from at least about 4 µg/mL to at least about 5 µg/mL, from at least about 5 µg/mL to at least about 6 µg/mL, from at least about 6 µg/mL to at least about 7 µg/mL, from at least about 7 µg/mL to at least about 8 µg/mL, from at least about 8 µg/mL to at least about 9 µg/mL, from at least about 9 µg/mL to at least about 10 µg/mL, from at least about 10 µg/mL to at least about 20 µg/mL, from at least about 20 µg/mL to at least about 30 µg/mL, from at least about 30 µg/mL to at least about 40 µg/mL, from at least about 40 µg/mL to at least about 50 µg/mL, from at least about 50 µg/mL to at least about 60 µg/mL, from at least about 60 µg/mL to at least about 70 µg/mL, from at least about 70 µg/mL to at least about 80 µg/mL, from at least about 80 µg/mL to at least about 90 µg/mL, from at least about 90 µg/mL to at least about 0.1 mg/mL, from at least about 0.1 mg/mL to at least about 0.2 mg/mL, from at least about 0.2 mg/mL to at least about 0.3 mg/mL, from at least about 0.3 mg/mL to at least about 0.4 mg/mL, from at least about 0.4 mg/mL to at least about 0.5 mg/mL, from at least about 0.5 mg/mL to at least about 0.6 mg/mL, from at least about 0.6 mg/mL to at least about 0.7 mg/mL, from at least about 0.7 mg/mL to at least about 0.8 mg/mL, from at least about 0.8 mg/mL to at least about 0.9 mg/mL, from at least about 0.9 mg/mL to at least about 1 mg/mL, from at least about 1 mg/mL to at least about 2 mg/mL, from at least about 2 mg/mL to at least about 3 mg/mL, from at least about 3 mg/mL to at least about 4 mg/mL, from at least about 4 mg/mL to at least about 5 mg/mL, from at least about 5 mg/mL to at least about 6 mg/mL, from at least about 6 mg/mL to at least about 7 mg/mL, from at least about 7 mg/mL to at least about 8 mg/mL, from at least about 8 mg/mL to at least about 9 mg/mL, from at least about 9 mg/mL to at least about 10 mg/mL, from at least about 10 mg/mL to at least about 20 mg/mL, from at least about 20 mg/mL to at least about 30 mg/mL, from at least about 30 mg/mL to at least about 40 mg/mL, from at least about 40 mg/mL to at least about 50 mg/mL, from at least about 50 mg/mL to at least about 60 mg/mL, from at least about 60 mg/mL to at least about 70 mg/mL, from at least about 70 mg/mL to at least about 80 mg/mL, from at least about 80 mg/mL to at least about 90 mg/mL, or from at least about 90 mg/mL to at least about 100 mg/mL.

In some embodiments, effective amounts of a peptide or pharmaceutically acceptable salt for treating or preventing an infection can be a concentration from at least about 0.01 µg/mL to at least about 100 mg/mL. In some embodiments, effective amounts of a peptide or pharmaceutically acceptable salt for treating or preventing an infection is at a concentration from at least about at least about 0.1 mg/mL to at least about 5 mg/mL. In some embodiments, effective amounts of a peptide or pharmaceutically acceptable salt for treating or preventing an infection is at a concentration from at least about at least about 0.5 mg/mL to at least about 1 mg/mL.

In some embodiments, effective amounts of a peptide or pharmaceutically acceptable salt for treating or preventing an infection is at a concentration about 1 mg/mL. In some embodiments, the effective amounts of a peptide or pharmaceutically acceptable salt for treating or preventing an infection is at a concentration about 2 mg/mL. In some embodiments, the effective amounts of a peptide or pharmaceutically acceptable salt for treating or preventing an infection is at a concentration about 3 mg/mL. In some embodiments, the effective amounts of a peptide or pharmaceutically acceptable salt for treating or preventing an infection is at a concentration about 4 mg/mL. In some embodiments, the effective amounts of a peptide or pharmaceutically acceptable salt for treating or preventing an infection is at a concentration about 5 mg/mL. In some embodiments, the effective amounts of a peptide or pharmaceutically acceptable salt for treating or preventing an infection is at a concentration about 6 mg/mL. In some embodiments, the effective amounts of a peptide or pharmaceutically acceptable salt for treating or preventing an infection is at a concentration about 7 mg/mL. In some embodiments, the effective amounts of a peptide or pharmaceutically acceptable salt for treating or preventing an infection is at a concentration about 8 mg/mL. In some embodiments, the effective amounts of a peptide or pharmaceutically acceptable salt for treating or preventing an infection is at a concentration about 9 mg/mL. In some embodiments, the effective amounts of a peptide or pharmaceutically acceptable salt for treating or preventing an infection is at a concentration about 10 mg/mL.

In some embodiments, effective amounts of a peptide or pharmaceutically acceptable salt for treating or preventing an infection may be a concentration from at least about 0.01 µg/mL to at least about 0.02 µg/mL, from at least about 0.02 µg/mL to at least about 0.03 µg/mL, from at least about 0.03 µg/mL to at least about 0.04 µg/mL, from at least about 0.04 µg/mL to at least about 0.05 µg/mL, from at least about 0.05 µg/mL to at least about 0.06 µg/mL, from at least about 0.06 µg/mL to at least about 0.07 µg/mL, from at least about 0.07 µg/mL to at least about 0.08 µg/mL, from at least about 0.08 µg/mL to at least about 0.09 µg/mL, from at least about 0.09

μg/mL to at least about 0.1 μg/mL, from at least about 0.1 μg/mL to at least about 0.2 μg/mL, from at least about 0.2 μg/mL to at least about 0.3 μg/mL, from at least about 0.3 μg/mL to at least about 0.4 μg/mL, from at least about 0.4 μg/mL to at least about 0.5 μg/mL, from at least about 0.5 μg/mL to at least about 0.6 μg/mL, from at least about 0.6 μg/mL to at least about 0.7 μg/mL, from at least about 0.7 μg/mL to at least about 0.8 μg/mL, from at least about 0.8 μg/mL to at least about 0.9 μg/mL, from at least about 0.9 μg/mL to at least about 1 μg/mL, from at least about 1 μg/mL to at least about 2 μg/mL, from at least about 2 μg/mL to at least about 3 μg/mL, from at least about 3 μg/mL to at least about 4 μg/mL, from at least about 4 μg/mL to at least about 5 μg/mL, from at least about 5 μg/mL to at least about 6 μg/mL, from at least about 6 μg/mL to at least about 7 μg/mL, from at least about 7 μg/mL to at least about 8 μg/mL, from at least about 8 μg/mL to at least about 9 μg/mL, from at least about 9 μg/mL to at least about 10 μg/mL, from at least about 10 μg/mL to at least about 20 μg/mL, from at least about 20 μg/mL to at least about 30 μg/mL, from at least about 30 μg/mL to at least about 40 μg/mL, from at least about 40 μg/mL to at least about 50 μg/mL, from at least about 50 μg/mL to at least about 60 μg/mL, from at least about 60 μg/mL to at least about 70 μg/mL, from at least about 70 μg/mL to at least about 80 μg/mL, from at least about 80 μg/mL to at least about 90 μg/mL, from at least about 90 μg/mL to at least about 0.1 mg/mL, from at least about 0.1 mg/mL to at least about 0.2 mg/mL, from at least about 0.2 mg/mL to at least about 0.3 mg/mL, from at least about 0.3 mg/mL to at least about 0.4 mg/mL, from at least about 0.4 mg/mL to at least about 0.5 mg/mL, from at least about 0.5 mg/mL to at least about 0.6 mg/mL, from at least about 0.6 mg/mL to at least about 0.7 mg/mL, from at least about 0.7 mg/mL to at least about 0.8 mg/mL, from at least about 0.8 mg/mL to at least about 0.9 mg/mL, from at least about 0.9 mg/mL to at least about 1 mg/mL, from at least about 1 mg/mL to at least about 2 mg/mL, from at least about 2 mg/mL to at least about 3 mg/mL, from at least about 3 mg/mL to at least about 4 mg/mL, from at least about 4 mg/mL to at least about 5 mg/mL, from at least about 5 mg/mL to at least about 6 mg/mL, from at least about 6 mg/mL to at least about 7 mg/mL, from at least about 7 mg/mL to at least about 8 mg/mL, from at least about 8 mg/mL to at least about 9 mg/mL, from at least about 9 mg/mL to at least about 10 mg/mL, from at least about 10 mg/mL to at least about 20 mg/mL, from at least about 20 mg/mL to at least about 30 mg/mL, from at least about 30 mg/mL to at least about 40 mg/mL, from at least about 40 mg/mL to at least about 50 mg/mL, from at least about 50 mg/mL to at least about 60 mg/mL, from at least about 60 mg/mL to at least about 70 mg/mL, from at least about 70 mg/mL to at least about 80 mg/mL, from at least about 80 mg/mL to at least about 90 mg/mL, or from at least about 90 mg/mL to at least about 100 mg/mL.

In some embodiments, effective amounts of a peptide or pharmaceutically acceptable salt for treating or preventing an infection may be from at least about 1 microliter (μL) to at least about 2 μL, from at least about 2 μL to at least about 3 μL, from at least about 3 μL to at least about 4 μL, from at least about 4 μL to at least about 5 μL, from at least about 5 μL to at least about 6 μL, from at least about 6 μL to at least about 7 μL, from at least about 7 μL to at least about 8 μL, from at least about 8 μL to at least about 9 μL, from at least about 9 μL to at least about 10 μL, from at least about 10 μL to at least about 20 μL, from at least about 20 μL to at least about 30 μL, from at least about 30 μL to at least about 40 μL, from at least about 40 μL to at least about 50 μL, from at least about 50 μL to at least about 60 μL, from at least about 60 μL to at least about 70 μL, from at least about 70 μL to at least about 80 μL, from at least about 80 μL to at least about 90 μL, from at least about 90 μL to at least about 100 μL, from at least about 100 μL to at least about 200 μL, from at least about 200 μL to at least about 300 μL, from at least about 300 μL to at least about 400 μL, from at least about 400 μL to at least about 500 μL, from at least about 500 μL to at least about 600 μL, from at least about 600 μL to at least about 700 μL, from at least about 700 μL to at least about 800 μL, from at least about 800 μL to at least about 900 μL, from at least about 900 μL to at least about 1 milliliter (mL), from at least about 1 mL to at least about 2 mL, from at least about 2 mL to at least about 3 mL, from at least about 3 mL to at least about 4 mL, from at least about 4 mL to at least about 5 mL, from at least about 5 mL to at least about 6 mL, from at least about 6 mL to at least about 7 mL, from at least about 7 mL to at least about 8 mL, from at least about 8 mL to at least about 9 mL, from at least about 9 mL to at least about 10 mL, from at least about 10 mL to at least about 20 mL, from at least about 20 mL to at least about 30 mL, from at least about 30 mL to at least about 40 mL, from at least about 40 mL to at least about 50 mL, from at least about 50 mL to at least about 60 mL, from at least about 60 mL to at least about 70 mL, from at least about 70 mL to at least about 80 mL, from at least about 80 mL to at least about 90 mL, from at least about 90 mL to at least about 100 mL, from at least about 100 mL to at least about 200 mL, from at least about 200 mL to at least about 300 mL, from at least about 300 mL to at least about 400 mL, from at least about 400 mL to at least about 500 mL, from at least about 500 mL to at least about 600 mL, from at least about 600 mL to at least about 700 mL, from at least about 700 mL to at least about 800 mL, from at least about 800 mL to at least about 900 mL, from at least about 900 mL to at least about 1 liter (L), from at least about 1 L to at least about 2 L, from at least about 2 L to at least about 3 L, from at least about 3 L to at least about 4 L, from at least about 4 L to at least about 5 L, from at least about 5 L to at least about 6 L, from at least about 6 L to at least about 7 L, from at least about 7 L to at least about 8 L, from at least about 8 L to at least about 9 L, from at least about 9 L to at least about 10 L, from at least about 10 L to at least about 20 L, from at least about 20 L to at least about 30 L, from at least about 30 L to at least about 40 L, from at least about 40 L to at least about 50 L, from at least about 50 L to at least about 60 L, from at least about 60 L to at least about 70 L, from at least about 70 L to at least about 80 L, from at least about 80 L to at least about 90 L, from at least about 90 L to at least about 100 L, from at least about 100 L to at least about 200 L, from at least about 200 L to at least about 300 L, from at least about 300 L to at least about 400 L, from at least about 400 L to at least about 500 L, from at least about 500 L to at least about 600 L, from at least about 600 L to at least about 700 L, from at least about 700 L to at least about 800 L, from at least about 800 L to at least about 900 L, from at least about 900 L to at least about 1 kiloliter (kL), from at least about 1 kL to at least about 2 kL, from at least about 2 kL to at least about 3 kL, from at least about 3 kL to at least about 4 kL, from at least about 4 kL to at least about 5 kL, from at least about 5 kL to at least about 6 kL, from at least about 6 kL to at least about 7 kL, from at least about 7 kL to at least about 8 kL, from at least about 8 kL to at least about 9 kL, or from at least about 9 kL to at least about 10 kL Combination Administration Also contemplated are combination products that include one or more peptides disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein.

In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In some embodiments, a pharmaceutical formulation can comprise an additional agent. In some embodiments, an additional agent can be present in a therapeutically effective amount in a pharmaceutical formulation. In some embodiments, an additional pharmaceutical agent can be an antibiotic agent. An antibiotic agent can of the group consisting of aminoglycosides, ansamycins, carbacephem, carbapenems, cephalosporins (including first, second, third, fourth and fifth generation cephalosporins), lincosamides, macrolides, monobactams, nitrofurans, quinolones, penicillin, sulfonamides, polypeptides and tetracycline. Alternatively, or additionally an antibiotic agent may be effective against mycobacteria. In some embodiments, an antibiotic agent may be an aminoglycoside such as Amikacin, Gentamicin, Kanamycin, Neomycin, Netilmicin, Tobramycin or Paromomycin. According to one embodiment, an antibiotic agent may be an Ansamycin such as Geldanamycin and Herbimycin. In some embodiments, an antibiotic agent may be a carbacephem such as Loracarbef. In some embodiments, an antibiotic agent can be a carbapenem such as Ertapenem, Doripenem, Imipenem/Cilastatin or Meropenem.

In some embodiments, an antibiotic agent may be a beta lactam antibiotic or pharmaceutically acceptable salt thereof may include but are not limited to Cephalexin, Cephradine, Cefadroxil, Cefazolin, B-lactam antibiotic C, Cephalothin, Cefapirin, Cefprozil, Loracarbef, Cefuroxime, Cefoxitin, Cefotetan, Cefaclor, Cefamandole, Ceftriaxone, Cefdinir, Cefixime, Cefpodoxime, Cefditoren, Ceftibuten, Ceftazidime, Cefotaxime, Cefoperazone, Ceftizoxime, Cefepime, Cefiderocol, Cefpirome, Ceftaroline, Benzathine, Benzylpenicillin, Phenoxymethylpenicillin, Procaine penicillin, Pheneticillin, Cloxacillin, Dicloxacillin, Flucloxacillin, Methicillin, Nafcillin, Oxacillin, Temocillin, Amoxillin, Ampicillin, Mecillinam, Carbenicillin, Ticarillin, Carbenicillin, Ticarcillin, Azlocillin, Mezlocillin, Piperacillin, Biapenem, Doripenem, Ertapenem, Faropenem, Imipenem, Meropenem, Panipenem, Razupenem, Tebipenem, Thienamycin, Aztreonam, Tigermonam, Nocardicin A, Tabtoxinine beta-lactam, Clavulanic acid, Tazobactam, Sulbactam, or Avibactam. In some embodiments, an antibiotic agent may be a cephalosporins (first generation) such as Cefadroxil, Cefazolin, Cefalexin, Cefalotin or Cefalothin, or alternatively a Cephalosporins (second generation) such as Cefaclor, Cefamandole, Cefoxitin, Cefprozil or Cefuroxime. Alternatively, an antibiotic agent may be a Cephalosporins (third generation) such as Cefixime, Cefdinir, Cefditoren, Cefoperazone, Cefotaxime, Cefpodoxime, Ceftibuten, Ceftizoxime and Ceftriaxone or a Cephalosporins (fourth generation) such as Cefepime and Ceftobiprole. In some embodiments, an antibiotic agent may be a lincosamide such as Clindamycin and Azithromycin, or a macrolide such as Azithromycin, Clarithromycin, Dirithromycin, Erythromycin, Roxithromycin, Troleandomycin, Telithromycin and Spectinomycin. In some embodiments, an antibiotic agent may be a monobactams such as Aztreonam, or a nitrofuran such as Furazolidone or Nitrofurantoin. In some embodiments, an antibiotic agent may be a penicillin such as Amoxicillin, Ampicillin, Azlocillin, Carbenicillin, Cloxacillin, Dicloxacillin, Flucloxacillin, Mezlocillin, Nafcillin, Oxacillin, Penicillin G or V, Piperacillin, Temocillin and Ticarcillin. In some embodiments, an antibiotic agent may be a sulfonamide such as Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, and Trimethoprim-Sulfamethoxazole (Co-trimoxazole) (TMP-SMX). In some embodiments, an antibiotic agent may be a quinolone such as Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin. In some embodiments, an antibiotic agent may be a polypeptide such as Bacitracin, Colistin and Polymyxin B. In some embodiments, an antibiotic agent may be a tetracycline such as Demeclocycline, Doxycycline, Minocycline and Oxytetracycline. In some embodiments, an antibiotic agent may be effective against mycobacteria. An antibiotic agent may be Clofazimine, Lamprene, Dapsone, Capreomycin, Cycloserine, Ethambutol, Ethionamide, Isoniazid, Pyrazinamide, Rifampicin, Rifabutin, Rifapentine or Streptomycin. In some exemplary embodiments, an antibiotic agent can include Ceftobiprole, Ceftaroline, Clindamycin, Dalbavancin, Daptomycin, Linezolid, Mupirocin, Oritavancin, Tedizolid, Telavancin, Tigecycline, Vancomycin, an Aminoglycoside, a Carbapenem, Ceftazidime, Cefepime, Ceftobiprole, a Fluoroquinolone, Piperacillin, Ticarcillin, Methicillin, Linezolid, a Streptogramin, Tigecycline, Daptomycin, a salt of any of these, or any combination thereof.

In some embodiments, an additional pharmaceutical agent can be an antimicrobial agent disclosed herein. In some embodiments, an antimicrobial agent can be cysteamine or a salt thereof. While cysteamine can be typically used to treat conditions such as cystinosis that are not derived from an infection, the use of cysteamine as an antimicrobial compound has shown promise. For example, International Patent Application Publication No. WO 2010112848 describes the use of formulations containing cysteamine for as antimicrobial agents capable of inhibiting the formation of a bacterial biofilm for a broad range of bacterial strains, including *Pseudomonas* spp., *Staphylococcus* spp., *Haemophilus* spp., *Burkholderia* spp., *Streptococcus* spp., *Propionibacterium* spp.

In some embodiments, an additional pharmaceutical agent can be an antiviral agent. In some embodiments, an antiviral agent can be Acyclovir, Brivudine, Cidofovir, Docosanol, Famciclovir, Foscarnet, Fomivirsen, Ganciclovir, Idoxuridine, Penciclovir, Peramivir, Trifluridine, Valacyclovir, Vidarabine, Lamivudine, Ribavirin Amantadine, Rimantadine, a neuraminidase inhibitor, Oseltamivir, Zanamivir, a salt of any of these, or any combination thereof.

In some embodiments, an additional pharmaceutical agent can be an antineoplastic. In some embodiments, an antineoplastic can be selected from the group consisting of cyclophosphamide, methotrexate, 5-fluorouracil, doxorubicin, procarbazine, prednisolone, bleomycin, vinblastine, dacarbazine, cisplatin, epirubicin, a salt of any of these, and any combination thereof.

In some embodiments, a peptide disclosed herein, salt thereof, or a formulation containing a peptide or salt thereof can be an antiviral agent.

In some embodiments, a peptide, pharmaceutically acceptable, or formulation can be administered in combination with an antibiotic or an additional antiviral agent disclosed herein.

Non-limiting examples of additional agents can include a surfactant such as polyoxyethylene sorbitan fatty acid esters (polysorbates), sodium lauryl sulphate, sodium stearyl fumarate, polyoxyethylene alkyl ethers, sorbitan fatty acid esters, polyethylene glycols (PEG), polyoxyethylene castor oil derivatives, docusate sodium, sugar esters of fatty acids, and glycerides of fatty acids; a quaternary ammonium compound such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; small molecules such as imidazole, indoles, nitric oxide, triazoles, phenols, sulfides, polysaccharides, furanones, and bromopyrroles; amino acids and their derivatives such as L-leucine, cysteamine, and additional peptides described herein. In some cases, an additional agent can be curcumin, apple cider vinegar, oregano, garlic, berberine, activated charcoal, or a proteolytic enzyme.

Infection

Provided herein are pharmaceutical formulations comprising a peptide and method of treating or preventing a disease or condition comprising administering the pharmaceutical formulation. In some embodiments, the condition or disease is an infection. In other embodiments, the infection is a microbial infection. In some embodiments, the infection is a bacterial infection, viral infection, fungal infection, or a combination thereof.

In some cases, a peptide can at least partially adopt an α-helical structure. An α-helical structure can more effectively integrate into a membrane of the bacterial cell, thereby improving the ability of a peptide to disrupt the structural integrity of the bacterial membrane. In some cases, a peptide can adopt an α-helix upon synthesis. In some cases, a peptide can adopt an α-helix when in an aqueous environment. In some cases, a peptide can adopt an α-helix when contacted with a bacterial membrane.

In some embodiments, bacterial infection may be derived from a bacterial species selected from the group, but not exclusive to the group, consisting of: *Staphylococcus* spp., e.g. *Staphylococcus aureus* (e.g. *Staphylococcus aureus* NCTC 10442 and *Staphylococcus aureus* ATCC 25923), *Staphylococcus epidermidis*; *Chlamydia* spp., e.g. *Chlamydia trachomatis, Chlamydia pneumoniae, Chlamydia psittaci; Enterococcus* spp., e.g. *Enterococcus faecalis; Streptococcus pyogenes; Listeria* spp.; *Pseudomonas* spp.; *Mycobacterium* spp., e.g. *Mycobacterium tuberculosis* complex; *Enterobacter* spp.; *Campylobacter* spp.; *Salmonella* spp.; *Streptococcus* spp., e.g. *Streptococcus* Group A or B, *Streptococcus pneumoniae; Helicobacter* spp., e.g. *Helicobacter pylori, Helicobacter felis; Neisseria* spp., e.g. *Neisseria* gonorrhoea, *Neisseria meningitidis; Borrelia burgdorferi; Shigella* spp., e.g. *Shigella flexneri; Escherichia coli* (*E. coli* O157:H7 NCTC 12900); *Haemophilus* spp., e.g. *Haemophilus influenzae; Francisella tularensis; Bacillus* spp., e.g. *Bacillus* anthraces; Clostridia spp., e.g. *Clostridium botulinum, Clostridium difficile; Yersinia* spp., e.g. *Yersinia pestis; Treponema* spp.; *Burkholderia* spp., e.g. *Burkholderia cepacia* complex, *B. mallei, B pseudomallei; Propionibacterium* spp., e.g. *P. acnes, Acinetobacter* species, an *Actinomyces* species, a *Campylobacter* species, a *Candida* species, *Corynebacterium minutissium, Corynebacterium pseudodiphtheriae, Corynebacterium stratium, Corynebacterium* group G1, *Corynebacterium* group G2, Enterobacteriaceae, an *Enterococcus* species, *Klebsiella pneumoniae*, a *Moraxella* species, a non-tuberculous mycobacteria species, a *Porphyromonas* species, *Prevotella melaninogenicus, Salmonella typhimurium, Serratia marcescens Streptococcus agalactiae, Staphylococcus salivarius, Streptococcus mitis, Streptococcus sanguis, Streptococcus pneumoniae, Vibrio cholerae*, a *Coccidioides* species, or a *Cryptococcus* species. In some embodiments, a peptide or pharmaceutically acceptable salt thereof described herein can reduce infection of bacteria against at least one of *Staphylococcus aureus*, methicillin resistant *Staphylococcus aureus, Streptococcus pneumonia*, carbapenem-resistant Enteroacteriaceae, *Staphylococcus epidermidis, Staphylococcus salivarius, Corynebacterium minutissium, Corynebacterium pseudodiphtheriae, Corynebacterium stratium, Corynebacterium* group G1, *Corynebacterium* group G2, *Streptococcus* pneumonia, *Streptococcus* mitis, *Streptococcus sanguis, Escherichia coli, Klebsiella pneumoniae, Pseudomonas aeruginosa, Burkholderia cepacia, Serratia marcescens, Haemophilus influenzae, Moraxella* sp., *Neisseria meningitidis, Neisseria gonorrhoeae, Salmonella typhimurium, Actinomyces* spp., *Porphyromonas* spp., *Prevotella melaninogenicus, Helicobacter pylori, Helicobacter felis*, or *Campylobacter jejuni*. In some embodiments, the bacterial may be antibiotic-tolerant or antibiotics-resistant. A bacterial strain can also be an antibiotic-resistant variant or a bacterial strain described herein. In some embodiments, a bacterial strain can be resistant to an antibiotic described herein.

A microbial biofilm, also referred to as a biological biofilm, can be a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature, are commonly found in a wide range of environments. Biofilms are being increasingly recognized by the scientific and medical community as being implicated in many infections, and especially their contribution to the recalcitrance of infection treatment. Biofilms can be etiologic agents for a number of disease states in mammals and are involved in 80% of infections in humans. Examples can include skin and wound infections, middle-ear infections, gastrointestinal tract infections, peritoneal membrane infections, urogenital tract infections, oral soft tissue infections, formation of dental plaque, eye infections (including contact lens contamination), endocarditis, infections in cystic fibrosis, and infections of indwelling medical devices such as joint prostheses, dental implants, catheters and cardiac implants. Microbes in biofilms can be significantly more resistant to antimicrobial treatment than their planktonic counterparts. Biofilm formation is not limited solely to the ability of microbes to attach to a surface. Microbes growing in a biofilm can interact more between each other than with the actual physical substratum on which the biofilm initially developed.

The suggested mechanisms by which biofilm-associated microorganisms elicit diseases in their host can include the following: (i) delayed penetration of the antimicrobial agent through the biofilm matrix, (ii) detachment of cells or cell aggregates from indwelling medical device biofilms, (iii) production of endotoxins, (iv) resistance to the host immune system, (v) provision of a niche for the generation of resistant organisms through horizontal gene transfer of antimicrobial resistance &/or virulence determinant genes, and (vi) altered growth rate (i.e. metabolic dormancy).

In some embodiments, bacteria, fungi, and/or protozoa, with associated bacteriophages and other viruses described herein can secrete a biofilm. In some embodiments, bacteria, fungi, and/or protozoa, with associated bacteriophages and other viruses described herein can form a biofilm. A peptide, pharmaceutically acceptable salt thereof described herein, or a formulation comprising a peptide or salt thereof described herein can be administered to at least partially penetrate, inhibit formation of, or destroy a biological biofilm. In some embodiments, additional agents can be added to at least partially inhibit formation of, or destroy, a biological biofilm.

In some embodiments, the infection is a viral infection. In some embodiments, a virus can be a DNA virus, a RNA virus, or a reverse transcriptase (retro) virus. A virus can be a dsDNA (double stranded DNA) virus, a ssDNA (single stranded DNA) virus, a dsRNA (double stranded RNA) virus, a +ssRNA (+strand or sense single stranded RNA) virus, a −ssRNA (−strand or antisense RNA) virus, a ssRNA-RT (single stranded RNA reverse transcriptase) virus, or a dsDNA-RT (double stranded DNA reverse transcriptase) virus. As described herein, a peptide described herein can be engineered to disrupt the integrity of a viral envelope of an enveloped virus. Such a disruption can at least partially reduce a viability of a virus, which can ameliorate an infection brought about by a virus. A virus may be derived from the group, but not exclusive to the group, of a herpesvirus, a poxvirus, a hepadnavirus, a flavivirus, a togavirus, a coronavirus, hepatitis C, hepatitis D, an orthomyxovirus, a papillomavirus, a polyomaviridae, a parvovirus, a cytomegalovirus, an Epstein-Barr virus, a small pox virus, a cow pox virus, a sheep pox virus, an orf virus, a monkey pox virus, a vaccinia virus, a paramyxovirus, a retrovirus, an adenovirus, a rhabdovirus, a bunyavirus, a filovirus, an alphavirus, an arenavirus, a lentivirus, and any combination thereof. In some embodiments, the virus can be an enveloped virus. Examples of an enveloped viruses can include: a poxvirus, a hepadnavirus, a flavivirus, a togavirus, a coronavirus, hepatitis C, hepatitis D, an orthomyxovirus, a cytomegalovirus, an Epstein-Barr virus, a small pox virus, a cow pox virus, a sheep pox virus, an orf virus, a monkey pox virus, a vaccinia virus, a rhabdovirus, a bunyavirus, a filovirus, an alphavirus, an arenavirus, a lentivirus, and the like.

Also envisaged are treatments of fungal, protozoal, or other parasitic infections by administration of a peptide described herein, salt thereof, or formulation containing a peptide or salt thereof. In some embodiments, a pathogen can be a drug-resistant fungal, protozoal, or other parasitic organism.

A parasitic pathogen may be derived from a parasite selected from, but not limited to, the group consisting of *Trypanosoma* spp. (*Trypanosoma cruzi, Trypansosoma brucei*), *Leishmania* spp., *Giardia* spp., *Trichomonas* spp., *Entamoeba* spp., *Naegleria* spp., *Acanthanioeba* spp., *Schistosoma* spp., *Plasmodium* spp., *Cryptosporidium* spp., *Isospora* spp., *Balantidium* spp., *Loa, Ascaris lumbricoides, Dirofilaria immitis*, and *Toxoplasma* ssp., e.g. *Toxoplasma gondii*.

A fungal pathogen may be derived from a fungus (including yeast) selected from, but not limited to, the genera *Candida* spp., (e.g. *C. albicans*), *Epidermophyton* spp., *Exophiala* spp., *Microsporum* spp., *Trichophyton* spp., (e.g. *T. rubrum* and *T. interdigitale*), *Tinea* spp., *Aspergillus* spp., *Blastomyces* spp., *Blastoschizomyces* spp., *Coccidioides* spp., *Cryptococcus* spp. (e.g. *Cryptococcus neoformans*), *Histoplasma* spp., *Paracoccidiomyces* spp., *Sporotrix* spp., *Absidia* spp., *Cladophialophora* spp., *Fonsecaea* spp., *Phialophora* spp., *Lacazia* spp., *Arthrographis* spp., *Acremoniwn* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphiwn* spp., *Leptosphaeria* spp., *Malassezia* spp. (e.g *Malassezia furfur*), *Mucor* spp., *Neotestudina* spp., *Nocardia* spp., *Nocardiopsis* spp., *Paecilomyces* spp., *Phoma* spp., *Piedraia* spp., *Pneunwcystis* spp., *Pseudallescheria* spp., *Pyrenochaeta* spp., *Rhizoinucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Ulocladium* spp., *Ustilago* spp., *Verticillium* spp., and *Wangiella* spp.

A fungal, bacterial, or viral infection may be a systemic, topical, subcutaneous, cutaneous or mucosal infection. Topical fungal infections of nails and skin are generally caused by detinatophytes although some non-dermatophytes such as yeast can also cause skin infections. A dermatophyte infection may include a *Tinea* infection for example *Tinea barbae* (beard), *Tinea capitis* (head), *Tinea corporis* (body), *Tinea cruris* (groin), *Tinea faciei* (face), *Tinea manuum* (hand), *Tinea pedis* (foot) *Tinea unguium* (nail), *Tinea (Pityriasis) versicolor, Tinea incognito* or *Tinea nigra*. An infection may be derived from fungi of the genera *Epidermophyton, Microsporum* or *Trichophyton* spp. (e.g. *T. rubrum* and *T interdigitale*). Exemplary dermatophytes can include *Epidermophyton floccosum, Microsporum canis, Microsporum audouinii, Microsporum gypseum, Microsporum nanum, Microsporum ferrugineum, Microsporum distortum, Microsporum fulvum, Trichophyton rubrum, Trichophyton tnentagrophytes* var. *interdigitale, Trichophyton mentagrophytes* var. *nodulare, Trichophyton tonsurans, Trichophyton soudanese, Trichophyton violaceum, Trichophyton megnini, Trichophyton schoenlenii, Trichophyton gallinae, Trichophyton krajdenii, Trichophyton yaoundei, Trichophyton equinum, Trichophyton erinacei* and *Trichophyton verrucosum*. In some embodiments, a dermatophytic infection can be onychomycosis. The term "onychomycosis" can include, but is not limited to, distal lateral subungual, superficial white, proximal white subungual, secondary dystrophic, primary dystrophic, endonyx, candidal (e.g. onycholysis & chronic mucocutaneous disease) types of onychomycosis and *Tinea ungium*. Non-dermatophytic fungi associated with onychomycosis can include *Aspergillus* spp., *Cephalosporum* spp., *Fusarium oxysporum, Scopularis brevicaulis*, and *Scytalidium* spp.

Kits

Disclosed herein are kits. A kit can comprise a peptide, salt thereof, formulation, or composition described herein. In some aspects, a peptide, formulation, or composition can be packaged in a container. In some aspects, a kit can further comprise instructions that direct administration of a unit dose of a peptide or formulation to a subject. In some aspects, a kit can comprise a peptide disclosed herein and instructions for the use thereof.

Methods of making a kit can include placing a peptide, salt thereof, formulation, or composition described herein in a container for packaging. A method can further comprise an inclusion of instructions for use. In some cases, instructions for use can direct administration of a unit dose of a peptide or formulation to a subject.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". As used herein, the terms "comprising," "comprise" or "comprised," and variations thereof, in reference to elements of an item, formulation, apparatus, method, process, system, claim etc. are intended to be open-ended, meaning that the item, formulation, apparatus, method, process, system, claim etc. includes those elements and other elements can be included and still fall within the scope/definition of the described item, formulation, apparatus, method, process, system, claim etc. As used herein "another" may mean at least a second or more.

The term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "substantially" as used herein can refer to a value approaching 100% of a given value. For example, a peptide that is "substantially localized" in an organ can indicate that about 90% by weight of a peptide, salt, or metabolite is present in an organ relative to a total amount of a peptide, salt, or metabolite. In some cases, the term can refer to an amount that can be at least about 90%, 91%, 92%, 93%, 94%, 95%, 96%, 97%, 98%, 99%, 99.9%, or 99.99% of a total amount. In some cases, the term can refer to an amount that can be about 100% of a total amount.

The term "subject", "patient" or "individual" as used herein can encompass a mammal and a non-mammal. A mammal can be any member of the Mammalian class, including but not limited to a human, a non-human primates such as a chimpanzee, an ape or other monkey species; a farm animal such as cattle, a horse, a sheep, a goat, a swine; a domestic animal such as a rabbit, a dog (or a canine), and a cat (or a feline); a laboratory animal including a rodent, such as a rat, a mouse and a guinea pig, and the like. A non-mammal can include a bird, a fish and the like. In some embodiments, a subject can be a mammal. In some embodiments, a subject can be a human. In some instances, a human can be an adult. In some instances, a human can be a child. In some instances, a human can be age 0-17 years old. In some instances, a human can be age 18-130 years old. In some instances, a subject can be a male. In some instances, a subject can be a female. In some instances, a subject can be diagnosed with, or can be suspected of having, a condition or disease. In some instances a disease or condition can be a bacterial infection. A subject can be a patient. A subject can be an individual. In some instances, a subject, patient or individual can be used interchangeably.

The terms "treat," "treating", "treatment," "ameliorate" or "ameliorating" and other grammatical equivalents as used herein, can include alleviating, or abating a disease or condition symptoms, inhibiting a disease or condition, e.g., arresting the development of a disease or condition, relieving a disease or condition, causing regression of a disease or condition, relieving a condition caused by the disease or condition, or stopping symptoms of a disease or condition.

The term "preventing" can mean preventing additional symptoms, ameliorating or preventing the underlying metabolic causes of symptoms, and can include prophylaxis.

In some instances, "treat," "treating", "treatment," "ameliorate" or "ameliorating" and other grammatical equivalents can include prophylaxis. "Treat," "treating", "treatment," "ameliorate" or "ameliorating" and other grammatical equivalents can further include achieving a therapeutic benefit and/or a prophylactic benefit. Therapeutic benefit can mean eradication of the underlying disease being treated. Also, a therapeutic benefit can be achieved with the eradication of one or more of the physiological symptoms associated with the underlying disease such that an improvement can be observed in a subject notwithstanding that, in some embodiments, the subject can still be afflicted with the underlying disease.

As used herein, a "pharmaceutically acceptable excipient", "aqueous carrier" or "pharmaceutically acceptable aqueous carrier" refer to solvents or dispersion media, and the like, that are physiologically compatible and known to those skilled in the art. Examples of pharmaceutically acceptable carriers include one or more of water, saline, phosphate buffered saline, dextrose, glycerol, ethanol, and the like, as well as combinations thereof. Pharmaceutically acceptable carriers may further comprise minor amounts of auxiliary substances such as wetting or emulsifying agents, preservatives or buffers, which enhance the shelf life or effectiveness of the active agent.

The terms "effective amount", "therapeutically effective amount" or "pharmaceutically effective amount" as used herein, can refer to a sufficient amount of a compound being administered which will at least partially ameliorate a symptom of a disease or condition being treated.

The terms "compound", "agent", or "therapeutic agent" can be used to refer to a peptide as described herein. In some cases, the terms "additional compound", "additional agent", or "additional therapeutic agent" can be used to refer to a peptide as described herein. In some cases, the terms "additional compound", "additional agent", or "additional therapeutic agent" can be used to refer to a compound, agent, or therapeutic that may not be a peptide described herein. For example, an additional agent can include an antioxidant, an antibiotic, an antifungal, an antiviral, an antineoplastic, a neoadjuvant, and the like. In some instances, "compound, "agent", and "therapeutic agent" can be used interchangeably.

The terms "peptide" and "polypeptide" can be used interchangeably to encompass both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids. A peptide can comprise an overall charge based on pka of side chains of component amino acids. In some instances, a peptide can have an overall positive charge. In some instances, a peptide can have an overall negative charge. In some instances, a peptide can have an overall neutral charge. A peptide can furthermore exist as a zwitterion.

A peptide described herein can be useful as an antimicrobial peptide, for example, against bacteria, fungi, yeast, parasites, protozoa and viruses. The term, "antimicrobial peptide" can be used herein to define any peptide that has microbicidal and/or microbistatic activity and encompasses, non-exclusively, any peptide described as having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties.

The term "recombinant" can refer to a biomolecule, e.g., a gene or protein, that (1) can be removed from its naturally occurring environment, (2) can be isolated from all or a portion of a polynucleotide in which the gene may be found in nature, (3) can be operatively linked to a polynucleotide which it may not be linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism can be recombinant, for example, if it is synthesized from an mRNA synthesized from a recombinant gene present in the cell.

The term "homology" can refer to a % identity of a polypeptide to a reference polypeptide. As a practical matter, whether any particular polypeptide can be at least 50%, 60%, 70%, 80%, 85%, 90%, 92%, 95%, 96%, 97%, 98% or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters can be set such that the percentage of identity is calculated over the full length of the reference amino acid sequence and that gaps in homology of up to 5% of the total number of amino acid residues in the reference sequence are allowed.

For example, in a specific embodiment the identity between a reference sequence (query sequence, i.e., a sequence of the present invention) and a subject sequence, also referred to as a global sequence alignment, may be determined using the FASTDB computer program based on the algorithm of Brutlag et al. (Comp. App. Biosci. 6:237-245 (1990)). In some embodiments, parameters for a particular embodiment in which identity is narrowly construed, used in a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity can be corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned can be determined by results of the FASTDB sequence alignment. This percentage can be then subtracted from the percent identity, calculated by the FASTDB program using the specified parameters, to arrive at a final percent identity score. This final percent identity score can be used for the purposes of this embodiment. In some embodiments, only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 amino acid residue subject sequence can be aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

The terms "co-administration", "administered in combination with" and their grammatical equivalents or the like, as used herein, can encompass administration of selected therapeutic agents to a subject, and can include treatment regimens in which agents are administered by the same or different route of administration or at the same or different times. In some embodiments, a peptide disclosed herein can be co-administered with other agents. These terms can encompass administration of two or more agents to a subject so that both agents and/or their metabolites are present in the subject at the same time. They can include simultaneous administration, administration at different times, and/or administration in a composition in which both agents are present. Thus, in some embodiments, a peptide and an additional agent(s) can be administered in a single composition. In some embodiments, a peptide and an additional agent(s) can be admixed in the composition. In some embodiments, a same peptide or agent can be administered via a combination of different routes of administration. In some embodiments, each agent administered can be in a therapeutically effective amount.

As used herein, the term "bioavailability" can denote the degree to which a drug such as a peptide, salt, metabolite, or other substance becomes available to the target tissue after administration.

Parameters often used in pharmacokinetic (PK) studies can include Tmax, Cmax, UC(0-∞), AUC(0-t), and T½ and CL/F. "Tmax" can refer to the time to reach the maximal plasma concentration ("Cmax") after administration of a therapeutic; "AUC(0-∞)" can refer to the area under the plasma concentration versus time curve from time 0 to infinity; "AUC(0-t)" can refer to the area under the plasma concentration versus time curve from time 0 to time t; "T½" can refer to a half-life of a therapeutic in blood plasma; "T½, elim" can refer to the half-life of elimination of the therapeutic from circulation; and "CL/F" can refer to an apparent clearance rate of a therapeutic.

As used herein, the terms "biofilm", "microbial film", "microbial biofilm", "bacterial film", refers to any film comprising microorganisms and their excretions.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art.

Experimental evolution coupled with whole genome sequencing (WGS) is a powerful strategy to characterize genetic mechanisms of resistance. Propagation of a bacterial population in the presence of an antibiotic will eventually select those clones that are capable of surviving the antibiotic exposure, and WGS of these populations or clones will reveal genetic causes of the resistance phenotype. This method is especially powerful when studying cationic peptides, as multiple mutations may be needed to evolve resistance to them.

Despite challenging several Gram-negative and Gram-positive pathogens with WLBU2 in vitro and in animal models, only P. aeruginosa has been observed to develop resistance to WLBU2 after long periods of exposure. Identifying the genes and the subsequent mutations that confer resistance to antimicrobial compounds provides a more comprehensive understanding of the modes of action of these antimicrobial compounds and how resistance to them evolves. Further, these discoveries can increase our ability to predict the emergence of antimicrobial resistance (AMR) in clinical scenarios.

Resistance to WLBU2 is rare because of its effectiveness and because it requires a specific combination of mutations. Therefore, a large mutation supply is needed to generate the narrow range of combinations of resistance determinants. A large mutation supply can be generated by an increase in mutation rate, large population sizes, and/or long periods of exposure. Due to the effectiveness of WLBU2 at killing and keeping bacteria population sizes small, increased mutation rates or prolonged subinhibitory exposure are the means for the bacteria to generate a larger mutation supply. Experimental evolution coupled with genomic sequencing was used to define mechanisms of resistance to WLBU2.

Example 1: Evolutionary Resistance Using Laboratory Strains

Methods

Experimental evolution: Three independent evolution experiments were conducted. The ancestor strains were propagated in a rich medium modified from M9 ("M9+") containing 0.37 millimolar (mM) $CaCl_2$, 8.7 mM $MgSO_4$, 42.2 mM $Na_2HPO_4$, 22 mM $KH_2PO_4$, 21.7 mM NaCl, 18.7 mM $NH_4Cl$ and 0.2 grams per liter (g/L) glucose and supplemented with 20 milliliters per liter (mL/L) MEM essential amino acids (Gibco 11130051), 10 mL/L MEM nonessential amino acids (Gibco 11140050), and 10 mL each trace mineral solution A, B, and C (Corning 25021-3Cl).

In the first experiment, a single clone of A. baumannii ATCC 17978 and P. aeruginosa PA14 were selected and propagated independently for 24 hours in M9+ in the absence of antibiotics. Each population was then sub-cultured into 10 replicate populations. Ten of the populations (5 planktonic and 5 biofilm) were propagated every 24 hours in increasing concentrations of WLBU2 (SEQ ID NO: 1) starting at 0.5× the minimum inhibitory concentration (MIC). The WLBU2 (SEQ ID NO: 1) was doubled after 72 hours until no population survived the treatment. As a control, the same number of strains were propagated (both planktonically and in biofilm) in the absence of antibiotics (e.g., WLBU2 (SEQ ID NO: 1)). Ten populations (5 planktonic and 5 biofilm) were propagated in increasing convention of the cationic peptide polymyxin B.

In the second experiment, 5 planktonic populations and 5 biofilm populations under the same conditions described above, and a mutator strain of P. aeruginosa (PA14 mutS: T114P), obtained from Flynn et al. ("Evolution of Ecological Diversity in Biofilms of Pseudomonas aeruginosa by Altered Cyclic Diguanylate Signaling." J. Bacteriol., 2016, 198:2608-2618). Additionally, 3 planktonic populations and 3 biofilm populations of the hypermutant strain in the absence of antibiotic (e.g., WLBU2 (SEQ ID NO: 1)) pressure were propagated. Hypermutant strains of bacteria, such as P. aeruginosa, can develop in patients, and may be characterized as having increased mutation rates, e.g., up to 1,000-fold, as compared to wild-type bacteria, such as P. aeruginosa (see, e.g., Maciá, Maria D et al. "Hypermutation is a key factor in development of multiple-antimicrobial resistance in Pseudomonas aeruginosa strains causing chronic lung infections." Antimicrobial agents and chemotherapy vol. 49, 8 (2005): 3382-6).

In the third experiment, 5 planktonic populations of the non-hypermutant laboratorial strain P. aeruginosa PA14 were propagated under subinhibitory concentrations of WLBU2 (SEQ ID NO: 1) for 10 days. The populations that survived the treatment with 1×MIC of WLBU2 (SEQ ID NO: 1) were propagated for 2 days.

All the experimental evolutions were performed using 18 millimeter (mm) glass tubes as shown in FIG. 1. The planktonic propagations were serially passaged through 50 uL into 5 mL of M9+(dilution factor 100) which corresponds to approximately 6.66 generations per day. For the biofilm populations, a polystyrene bead (Polysciences, Inc., Warrington, PA) was transferred to fresh media containing 3 sterile beads. Each bead was rinsed in phosphate buffered saline (PBS) before the transfer to reduce the transfer planktonic cells. Each day, black and white marked beads were alternated, ensuring that the bacteria were growing on the bead for 24 hours, which corresponds to 6 to 7.5 generations/day.

In all three experiments, 1 mL of the surviving populations at days 1, 3, 4, 6, 7, 9, 10 and 12 were frozen in 9% of dimethyl sulfoxide (DMSO) (before and after increases in antibiotics).

Phenotypic characterization: antimicrobial susceptibility and aggregation assay: The MIC to WLBU2 (SEQ ID NO: 1) and polymyxin B of the whole populations and 4 clones were determined by broth microdilution according to the Clinical and Laboratory Standards Instituted guidelines (CLSI 2019), in which each bacterial sample was tested in 2-fold increasing concentrations of each antibiotic. WLBU2 (SEQ ID NO: 1) was provided by Peptilogics (Peptilogics, Pittsburgh, PA) and polymyxin B was provided by Alfa Aesar (Alfa Aesar, Wardhill, Mass.). The experiments were performed with three replicates of the antibiotics.

To determine the aggregation ability of the 4 clones selected in the subinhibitory experiment, two replicates (R1 and R2) of each clone and the ancestral strain were grown in 5 mL of M9$^+$ for 24 hours at 37 degrees Celsius (° C.) in a roller drum at 200 revolutions per minute (RPM). After 24 hours, the whole culture of each clone was transferred to a 13 mm glass tube, and the tubes were allowed to settle over 24 hours at 4° C. without shaking. Replicate 1 (R1) of each clone was vortexed for 30 seconds and the optical density at 600 nanometers ($OD_{600}$) was measured. From R2, 200 µl of the upper fraction was carefully taken without vortexing and the $OD_{600}$ was measured. The aggregation percentage was estimated as $100 \times ((1-OD_{600}\ R2)/(1-OD_{600}\ R1))$. This experiment was performed with five replicates both in the absence and presence (4 µg/ml) of WLBU2 (SEQ ID NO: 1).

Genome Sequencing: Whole population genome sequencing of the population that survived the treatment in each experiment, as well as control lines, was performed with coverage of 148.01±42.80 reads. This includes 3 biofilm and 2 planktonic populations of mutator populations surviving WLBU2 (SEQ ID NO: 1) treatments and 4 biofilm and 3 planktonic populations evolved in the absence of the antibiotic (WLBU 2 (SEQ ID NO: 1)) (12 total populations). In addition, 2 populations and 4 clones that survived subinhibitory WLBU2 (SEQ ID NO: 1) treatment were sequenced, as well as one untreated control population (2 populations, 4 clones). Finally, 3 biofilm and 3 planktonic populations of *A. baumannii* that were propagated in presence of polymyxin B were sequenced, as well as 3 planktonic and 3 biofilm populations (12 populations total).

Each population or clone was revived from a freezer stock in the growth conditions under which they were isolated and grew for 24 hours. DNA was extracted using Qiagen DNAeasy Blood and Tissue kit (Qiagen, Hiden, Germany). The sequencing library was prepared according to the protocol Baym et al. ("Inexpensive multiplexed library preparation for megabase-sized genomes". *PLoS One* 2015, 10:e0128036) using Illumnia Nextera Kit (Illumina Inc., San Diego, Calif.) and sequenced using Illumnia NextSeq500.

Data Processing: The variants were called using the breseq software package v0.31.0 using the default parameters and the -p flag when required for identifying polymorphism in populations after all sequences were first quality filtered and trimmed with the Trimmomatic software v0/36 using the criteria: LEADING:20 TRAILING:20 SLIDING-WINDOW:4:20 MINLEN:70 (Deatherage et al. "Identification of mutations in laboratory-evolved microbes from next-generation sequencing data using breseq." Methods Mol. Biol., 2014, 1151:165-188; Bolger et al. "Trimmomatic: a flexible trimmer for Illumina sequence data," Bioinformatics 2014, 30:2114-2120). The version of *A. baumannii* ATCC 17978-mff (GCF_001077675.1 downloaded from the NCBI RefSeq database, 17 Mar. 2017) was used as the reference genome for variant calling. Two additional plasmid sequences were added in the *A. baumannii* strain (NC009083, NC_009084) to the chromosome NZ_CP012004 and plasmid NZ_CP012005. The version of *P. aeruginosa* UCBPP-PA14 was downloaded from RefSeq on 25 Aug. 2020. False positives were removed as described: mutations were removed if they never reached a cumulative frequency across time points 25%, or if mutations were also found in the ancestor's genome. The mutS clone used was a merodiploid bearing both the ancestral and the mutated mutS gene. As breseq can fail to detect mutations when analyzing repeated sequences, the mutS locus was manually visualized with the bam files generated by breseq using the Integrative genomics viewer software, confirming that the mutation was present in the ancestral clone and in all evolved populations sequenced at ca. 50% frequency.

Results

For identifying mechanisms of resistance to WLBU2 (SEQ ID NO: 1), laboratory strains of *A. baumannii* ATCC 17978 and *P. aeruginosa* PA14 that had no prior exposure to WLBU2 (SEQ ID NO: 1) were propagated. Large populations of bacteria were treated with increasing concentrations of antibiotics ((WLBU2 (SEQ ID NO: 1)) over 12 days (FIG. 1). Both strains were serially passaged (bottleneck of ~107 colony forming units (cfu)) in WLBU2 (SEQ ID NO: 1) concentrations, initially at half the MIC and increasing concentrations two-fold every three days, up to four times the MIC. The same number of populations were propagated in the absence of WLBU2 (SEQ ID NO: 1) to distinguish between adaptation to the environment and WLBU2 (SEQ ID NO: 1) related mutations. As biofilm formation can influence the evolution of resistance, both planktonic and biofilm cultures were propagated. For testing the general capability of the experimental design for selecting populations, resistant to cationic peptides, populations of *A. baumannii* in each lifestyle with increasing concentrations of polymyxin B were propagated. While all planktonic populations and four out of the five biofilm populations survived in 4-times the MIC of polymyxin B, mainly through mutations in the pmrABC operon and in genes modifying lipid A, no populations of *A. baumannii* and *P. aeruginosa* survived exposure of the MIC of WLBU2 (SEQ ID NO: 1). This suggested that there may be a narrow genetic pathway to gain WLBU2 (SEQ ID NO: 1) resistance that could require more than one mutation. Two factors that increase the likelihood of developing resistance were determined to be: i) the mutation supply determined by population size and the mutation rate and ii) the strength of selection imposed by the antibiotic. For exemplary calculation, a conservative mutation rate of 0.001 mutations per genome per generation, and a Poisson distribution of mutations in the genome, this experiment had a cumulative probability of approximately 0.35 for *A. baumannii* and 0.29 for *P. aeruginosa* that any given nucleotide had been mutated at least once following three days of growth (approximately 36 generations) in subinhibitory concentrations, i.e. before being exposed to lethal concentrations (Table 2). In Table 2, the mean mutations per nucleotide and the cumulative probability of a mutation per nucleotide knowing the mutation rate was calculated using the length of the chromosome, the number of divisions/days, and the length of the exposure before facing inhibitory concentrations of antibiotic (WLBU2 (SEQ ID NO: 1)). Thus, it was possible that the correct mutation or combination of mutations needed to survive the antibiotic (WLBU2 (SEQ ID NO: 1)) treatment had not occurred before facing inhibitory concentrations. The following experiments focused on *P. aeruginosa* to increase the number of sample mutations to determine how resistance could emerge to WLBU2 (SEQ ID NO: 1). Two approaches were pursued to increase the number of mutations sampled in *P. aeruginosa* populations to cultivate resistance to WLBU2 (SEQ ID NO: 1): increasing the mutation rate and extending the duration of subinhibitory exposure as provided in FIG. 2.

TABLE 2

Mutation supply and distribution of mutations in the three different experiments.

|  | Previously used protocol | Adapted protocols | |
|---|---|---|---|
|  |  | Hypermutator ancestor | Extended subinhibitory exposure |
| Strain | PA14 | PA14 mutS: T114P | PA14 |
| Mutation rate (mutation/genome/division)[a] | 0.001 | 0.1 | 0.001 |
| Length of exposure (days)[b] | 3 | 3 | 110 |
| Total cell divisions[c] | $2.98 \times 10^9$ | $2.98 \times 10^9$ | $9.91 \times 10^9$ |
| Total mutations[d] | $2.98 \times 10^6$ | $2.98 \times 10^8$ | $9.91 \times 10^6$ |
| Mean mutation per nucleotide, cumulatively[e] | 0.458 | 45.8 | 1.52 |
| Cumulative propbabilty of a mutation per nucleotide[f] | 36.8% | 100% | 73.6% |
| Results |  |  |  |
| Populations that survived entire experiment (%) | 0% | 50% | 40% |

Figure 2:
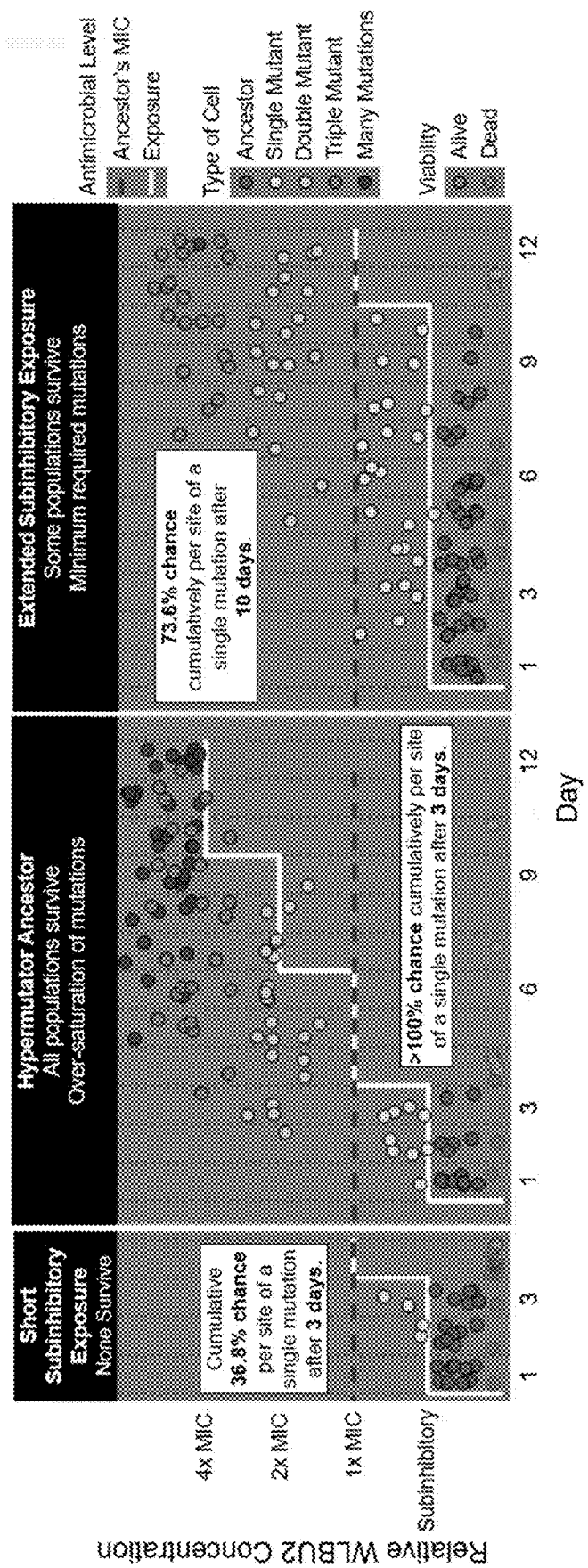
FIG. 2 is a schematic overview of the experimental set up. Wild-type *P. aeruginosa* PA14 (WT) was exposed to different WLBU2 (SEQ ID NO: 1) treatments. In the left panel, populations were grown in subinhibitory concentrations of WLBU2 (SEQ ID NO: 1) for 3 days and then the concentration was doubled to inhibitory concentrations that caused extinction. The middle panel used a hypermutator PA14 strain with a 100-fold greater mutation rate than WT. In the right panel, the WT was propagated for 10 days in subinhibitory concentrations of WLBU2 (SEQ ID NO: 1), increasing the mutation supply by augmenting the number of mutation supply by augmenting the number of generations. Dots simulate the expected number of mutants as calculated in Table 2.
Figure 3A:
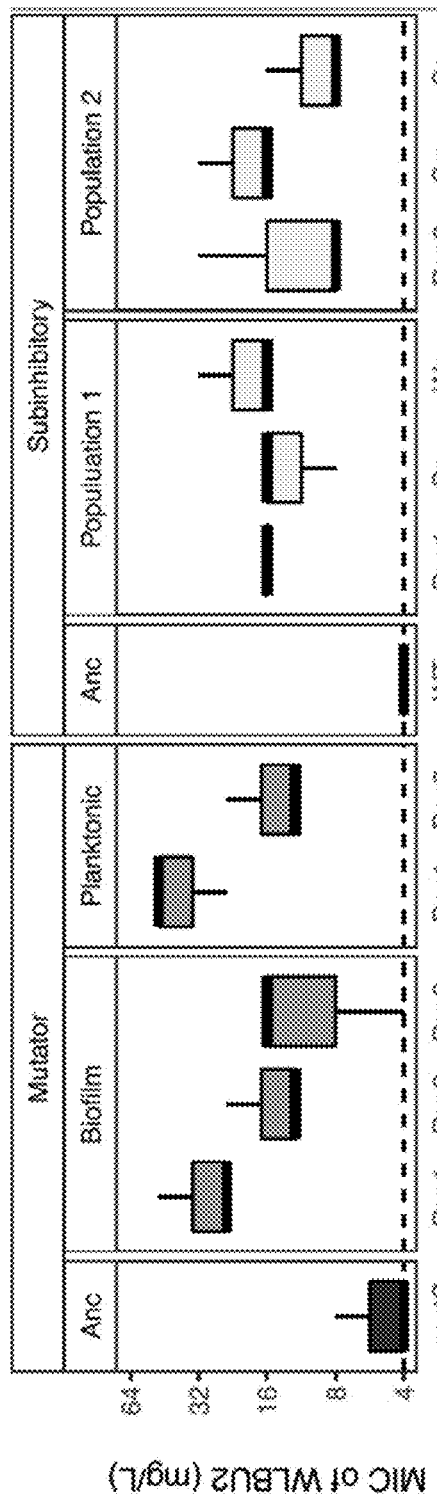
FIG. 3A provides box plots depicting resistance levels of populations evolved in the presence of WLBU2 (SEQ ID NO: 1) at minimum inhibitory concentrations (MIC) (mg/L). The boxplots show the median and quartiles for 3 replicates. Populations evolved from mutS mutator genotype are in dark grey and resistance clones isolated from WT ancestor are in light grey. All populations significantly exceeded WT resistance ($p<0.05$, one-way ANOVA with post-hoc pairwise testing). Dotted lines denote the MIC of the ancestor and grey lines note the maximum concentration of WLBU2 (SEQ ID NO: 1) that populations were challenged to during the evolution experiment.

[a]Calculated in Harris et al. "Polygenic Adaptation and Clonal Interference Enable Sustained Diversity in Experimental *Pseudomonas aeruginosa* Populations", *Molecular biology and Evolution*, 2021, 38(12): 5359-5375.
[b]Days propagated before facing inhibitory concentrations of WLBU2 (SEQ ID NO: 1)
[c]Calculated as the sum of cell divisions to regrow the population each day following dilution into fresh culture
[d]Total cell divisions multiplied by mutation rate
[e]Total mutations divided by chromosome size
[f]Based on Poisson distribution of the mutations Increasing mutation supply by using hypermutator strain promotes evolution resistance: A method to increase mutation supply during evolution experiments was to use an ancestral strain with a higher mutation rate. These mutator genotypes commonly evolve during chronic infections of *P. aeruginosa* and therefore relevant to antimicrobial resistance (AMR) evolution. The strain of *P. aeruginosa* PA14 with a defect in mismatch repair (mutS T112P) was selected, producing a mutation rate of approximately 100 times higher than the ancestor and showing a level of resistance to WLBU2 (SEQ ID NO: 1) of 5.3±2.3 mg/L as seen in FIG. 3A. Under the same experimental conditions described above, each nucleotide experiences greater than 40 mutations over the first three days of growth under subinhibitory conditions. Five mutator populations were propagated in each lifestyle combination following the previously described protocol. Two planktonic and three biofilm populations survived this treatment, resulting in 3 to 7.5-fold increase in resistance relative to the ancestor as seen in FIG. 2A. The other 5 populations did not survive when facing the MIC of WLBU2 (SEQ ID NO: 1).

The genomes were sequenced from the five surviving populations to a depth of 148.01±42.80 reads and detected a total of 98 mutations at frequencies greater than 0.1, including fixed mutations. As the ancestor was a mutator strain, it was difficult to infer what mutations were the drivers of the resistance phenotype and which were hitchhikers. The instances of gene-level parallel (repeated) evolutions were focused on as strong candidates, because mutations in the same gene found independently derived lineages provide strong evidence of selection on this trait. Further, the large population size and high mutation supply empowers selection to enrich the most beneficial genotypes.

Figure 3B:
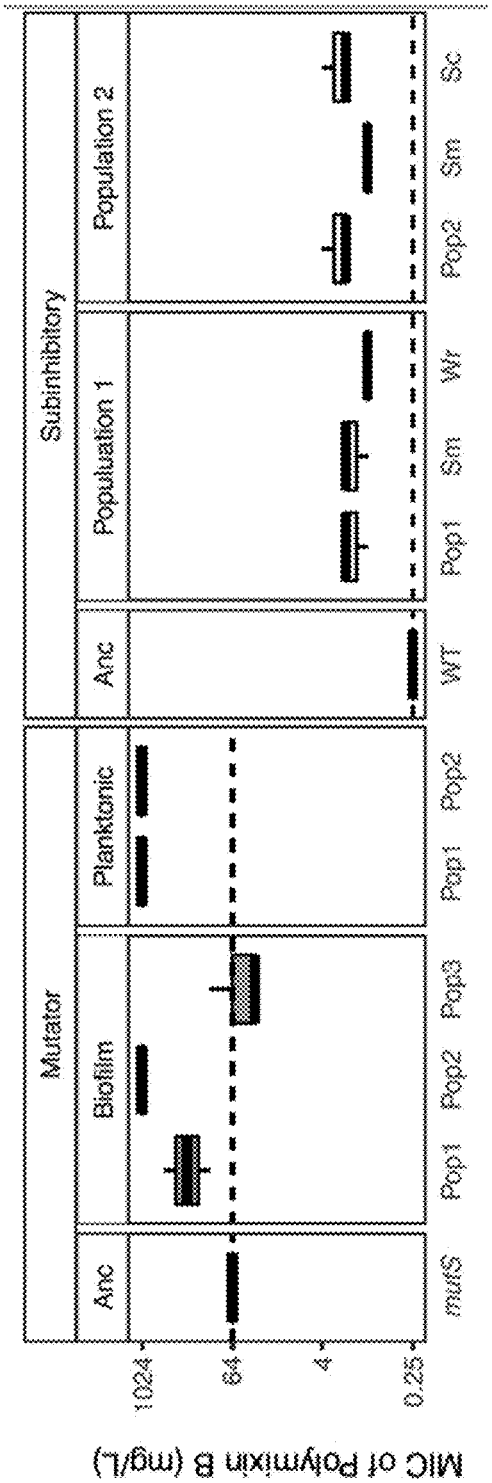
FIG. 3B provides box plots depicting resistance levels of populations evolved in the presence of polymyxin B as MIC (mg/L). Dotted lines denote the MIC of the ancestor.
Figure 4:
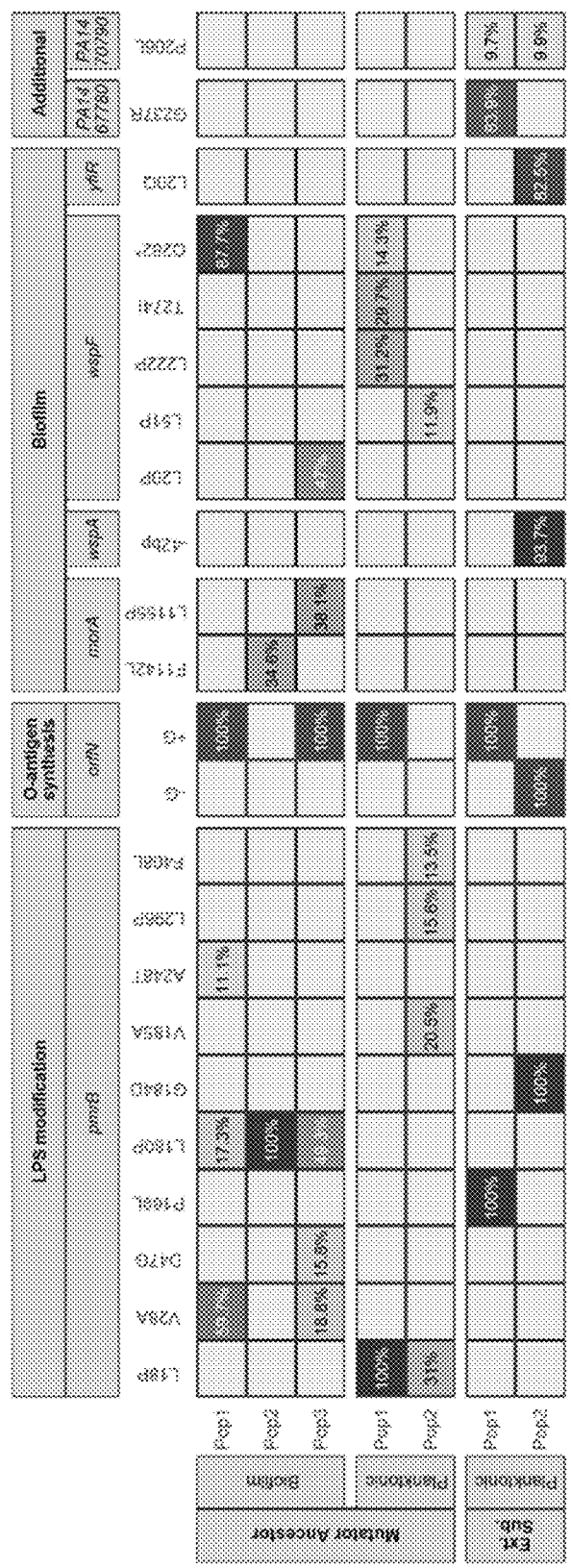
FIG. 4 is a diagram showing the whole genome sequencing (WGS) of the populations revealing mutations in a few genes selected in parallel to high frequencies in all populations, suggesting that a minimum of two mutations among 3 are key functional categories that may be required to increase resistance to WLBU2 (SEQ ID NO: 1). While most fixed mutations were seen in the mutator-derived populations, genetic hitchhiking was more likely these conditions. Parallel and high frequency mutations were focused as both were seen in the extended subinhibitory phase and mutator-founded experiments (indicative of adaptive targets and driver mutations).

Only four genes, orfN, pmrB, wspF, and morA, were mutated in more than one population exposed to WLBU2 (SEQ ID NO: 1) and not in the populations evolving in absence of the antibiotics, indicating roles of these mutations in evading antibiotic treatment (FIG. 4). Exemplary sequences of orfN, pmrB, and wspF, are provided in Table 3. The two-component regulator pmrB governs several modifications of lipopolysaccharides (LPS) and may confer to resistance to other cationic peptide. Four of the five WLBU2 (SEQ ID NO: 1) resistant populations show cross-resistance to polymyxin B, increasing their MIC from 2 to greater than or equal to 4-fold as seen in FIG. 3B. The wspF gene encodes a methylesterase that regulates activity of the surface-sensing Wsp cluster that in turns activates the diguanylate cyclase WspR and biofilm production. The morA gene encodes multiple sensor domains that control diguanylate cyclase and phosphodiesterase domains acting on the second messenger cyclic di-GMP. This MorA gene product promotes biofilm production at high levels and motility at low levels. These bio-film associated mutations strongly indicate that production of aggregates or biofilm plays a role in resisting WLBU2 (SEQ ID NO: 1).

TABLE 3

Sequences for pmrB, orfN and wspF

| SEQ ID NO: | Sequence | Gene | Protein |
|---|---|---|---|
| 26 | MHFLRRPISL RQRLILTIGA ILLVFELISV FWLWHESTEQ IQLFEQALRD NRNNDRHIIR EIREAVASLI VPGVFMVSLT LFICYQAVRR ITRPLAELQK ELEARTADNL TPIAIHSATL EIEAVVSALN DLVSRLTSTL DNERLFTADV AHELRTPLAG VRLHLELLAK THHIDVAPLV ARLDQMMESV SQLLQLARAG QSESSGNYQH VKLLEDVILP SYDELSTMLD QRQQTLLLPE SAADITVQGD ATLLRMLLRN LVENAHRYSP QGSNIMIKLQ EDDGAVMAVE DEGPGIDESK CGELSKAFVR MDSRYGGIGL GLSIVSRITQ LHHGQFFLQN RQETSGTRAW VRLKKDQYVA NQI | pmrB | histidine kinase (*E. coli*) |

TABLE 3-continued

Sequences for pmrB, orfN and wspF

| SEQ ID NO: | Sequence | Gene | Protein |
|---|---|---|---|
| 27 | MMNLWLLLPA VAALSLLLTA GLRRYAIARS LIDVPNARSS HQVPTPTGGG VAIVLSFLLA VLLAAILGAV KPDLATGILG AGIGIALLGF LDDHGHIAAR WRLLGHFAGA CWLLYWLGGL PALAFFGLVV DLGWVGHIAA AFYLVWMLNL YNFMDGIDGI ASVEAVCVCV GAALLVVVSG VGSDEASQGV WLAALLAAAV TGFLFWNFPP ARIFMGDAGS GFLGVIIGGL SLQAAWVSPQ LFWGWLILLG VFIVDATLTL LRRLLRGDKV YEAHRSHAYQ YASRHYGRHL PVTLAVGGIN IFWLLPLALL VAAGKIDGML ALLIGYLPLA FLALRFKAGV LESRAA | orfN | putative group 4 glycosyl transferase (E. coli) |
| 28 | MKIAIVNDMP LAVEALRRAL AFEPAHQLVW VAANGAEAVQ RSAEYTPDLI LMDLFMPVMD GVEATRRIMA DSPCAIVIVT GDSQQNVHRV FEAMGHGALD VVDTPALGVG NPADAAAPLL RKITNIGWLI GERNKRERPA PAAQRAAVSR KSLVAIGSSA GGPAALEVLL KALPRDFTPA IVLVQHVDEV FAAGMAEWLG SVSGHTVRLA RQGETPQSGT VLLAGTNHHL RLLKDGTLAY TAEPVNEIYR PSIDVFFESV AQYWSGDAVG VLLTGMGRYG AQGLKLMRQQ GYVTIAQDQR SSAVYGMPKA AAAIDAAAHI LALDAIAPRL LEIFTP | wspF | protein-glutamate methylesterase/protein-glutamine glutaminase (E. coli) |
| 29 | MSRAAVPSVR RRLLVNLLVG FVLCWLSVAA LTYHLSLKQV NRLFDDDMVD FGEAALRLLD LATEDQAGED GSITEIIERS REAIQGLPLL RRESALGYAL WRDGQPLLSS LNLPPEITAQ GPGFSTVEAQ GTHWRVLQLN IDGFQIWISE NLIYRQHTMN LLLFYSLFPL LLALPLLGGL VWFGVARGLA PLREVQAEVQ QRSARHLQPI AVEAVPLEIR GLIDELNLLL ERLRTALEAE RRLTSDAAHE IRTPLASLRT HAQVALRSED PKAHARGLLQ VSRSVERIST LMEQILLLAR LDGDALLEQF HPVNLATLAE DVLSELARQA IDKDIELSLH QETVYVMGID LWLKAMVGNL VGNALRYTPA GGQVEIRVEN RAQHAVLRVR DNGPGVALEE QQAIFTRFYR SPATSSGEGS GLGLPIVKRI VELHFGSIGL GKGLEGKGLE VQVFLPKTQP DATRPPARGP DSGRSHI | pmrB | histidine kinase (P. aeruginosa) |
| 30 | MMNLWLLLPA VAALSLLLTA GLRRYAIARS LIDVPNARSS HQVPTPRGGG VAIVLSFLLA VLLAAILGAV KPDLATGILG AGIGIALLGF LDDHGHIAAR WRLLGHFAGA CWLLYWLGGL PALAFFGLVV DLGWVGHIAA AFYLVWMLNL YNFMDGIDGI ASVEAVCVCV GAALLVVVSG VGSDEASQGV WLAALLAAAV TGFLFWNFPP ARIFMGDAGS GFLGVIIGGL SLQAAWVSPQ LFWGWLILLG VFIVDATLTL LRRLLRGDKV YEAHRSHAYQ YASRHYGRHL PVTLAVGGIN IFWLLPLALL VAAGKIDGML ALLIGYLPLA FLALRFKAGV LESRAA | orfN | putative group 4 glycosyl transferase (P. aeruginosa) |
| 31 | MRIGIVNDMP LAVEALRRAL AFEPQHQIVW VASNGAEAVT QCAADTPDVV LMDLLMPVMD GVEATRRIMA ESPCAIVIVT VDIEQNVHRV FEAMGYGALD AVNTPALGIG NPQTAAAPLL RKIQNVGWLI GQRDNRGKVQ VVPPKAGGAR QRLVAIGASA GGPASLAVLL KQLPASFNAA VVLVQHVDEV FAAGMAEWLA SESKLPVRLA RDGEPPIPGQ ILLAGTNNHI RLLRNGSLVY TAEPRSFVYR PSIDVFFESV ANYWRGDAVG VLLTGMGRDG AQGLKQMRER GFLTIAQDQA SCAVYGMPKA AAAIDAAVQI LSLEKIAPRL AEVFD | wspF | protein-glutamate methylesterase/protein-glutamine glutaminase (P. aeruginosa) |

Extending the exposure of subinhibitory concentrations: The mutator genotype of *P. aeruginosa* facilitated the evolution of resistance to WLBU2 (SEQ ID NO: 1) as seen in FIG. 2A, but isolating clones without other background mutations was challenging because of their increased mutation rate. The parallelism in orfN, morA, wspF and pmrB was a strong indicator of the fitness benefits of these mutations as seen in FIG. 4. Because resistance could evolve by increasing the mutation supply, increasing the number of generations in subinhibitory concentrations of WLBU2 (SEQ ID NO: 1) was tested as it may increase the chance for the WT (non-mutator) ancestor of acquiring mutations needed to survive inhibitory concentrations.

Figure 6:
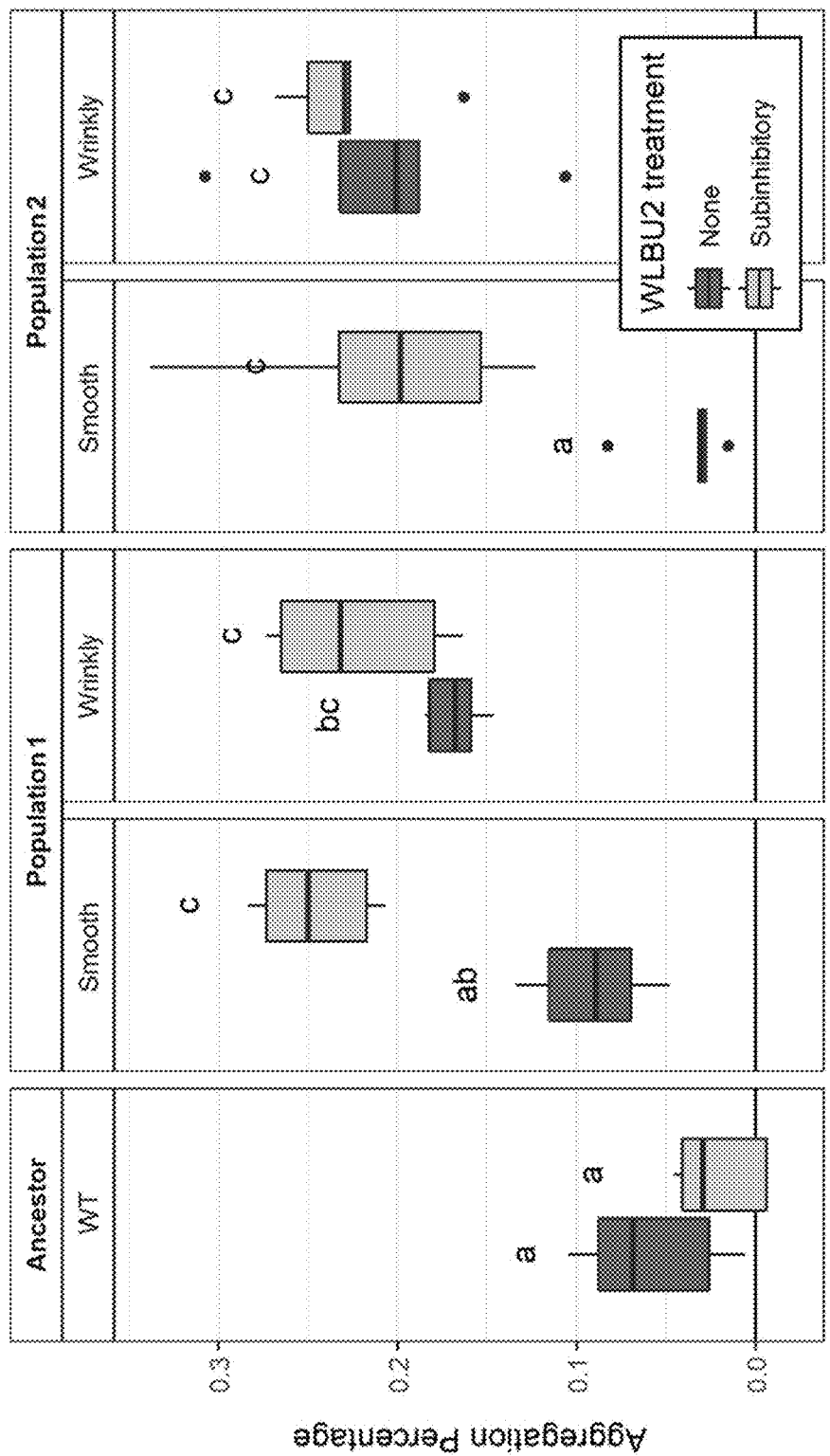
FIG. 6 provides box plots showing aggregation of PA14 and resistant clones. The resistant Wrinkly (Wr) and Small (Sc) clones (associated with wsp mutations) aggregated more than WT regardless of WLBU2 treatment, while the Smooth (Sm) populations of each clone settled for 24 hours at 4° C., n=5. Means sharing a letter are not significantly different (Sidak-adjusted least-square means for multiple comparisons, $p<005$). Bars show 95% confidence intervals of least-square means.

Five planktonic populations of wild-type *P. aeruginosa* PA14 was propagated for 10 days under subinhibitory concentrations of WLBU2 (SEQ ID NO: 1), followed by 2 days at inhibitory concentrations. It was estimated the probability that any given nucleotide would be mutated during this regime was 0.74, with mean mutations per site of 1.52. As a control, three populations were propagated in the absence of WLBU2 (SEQ ID NO: 1) to distinguish between broth and WLBU2 (SEQ ID NO: 1) adaptive mutations. Only two populations survived the prolonged subinhibitory treatment. Those two populations showed a 3 to 4-fold increase in resistance to WLBU2 (SEQ ID NO: 1) and a 2 to 3-fold increase to polymyxin B as seen in FIG. 2. Different colony morphologies were also detected within each population at the end of the experiment. Population 1 included rugose or wrinkly (Wr) colonies in addition to the smooth (Sm) morphology of the ancestor, and population 2 contained both Sm and small (Sc) colonies as seen in FIG. 5. Small colony variants may be associated with aggregation, increased biofilm formation, and worse outcomes in chronic infections. The clones were tested to determine if they produced more biofilm by measuring aggregation in the presence of absence of WLBU2 (SEQ ID NO: 1). The Sc and Wr clones settled in clumps more than the WT both in absence and presence of WLBU2 (SEQ ID NO: 1), while Sm colonies only clustered more in the presence of the peptide as seen in FIG. 6.

WGS of the two surviving populations and representative clones of each colony type revealed that all acquired mutations were in the pmrB gene, as well as mutations known to increase biofilm production (FIGS. 4 and 7). The two small colony variants acquired mutations in wspA or wspF in the Wsp pathway seen previously in the mutator experiment, while one resistant Sm clone acquired orfN and pmrB mutations as well as yfiR mutations, another gene known to activate c-di-GMP synthesis. These biofilm-activating mutations were selected during the planktonic propagation of the populations, suggesting that forming aggregates may be a key step for resistance to WLBU2 (SEQ ID NO: 1). In addition, both resistant populations and the two clones with smooth morphology had mutations in the orfN gene, which is involved in the synthesis of the O-antigen. Further, one Wr isolated had a mutation in the wbpM gene, which also contributes to O-antigen biosynthesis. The only mutations common to both prolonged subinhibitory selection and the mutator lineages exposed to WLBU2 (SEQ ID NO: 1) occurred in pmrB, orfN and wspF, providing evidence of fitness benefits of these mutations affecting both LPS composition and biofilm production in the presence of WLBU2 (SEQ ID NO: 1) and summarized in Table 4. Each column in Table 4 shows the frequency (in parentheses) of the mutations present in each population or clone. Only mutations evolved in the populations exposed to WLBU2 (SEQ ID NO: 1) above 5% frequency and not present in the untreated controls are shown.

TABLE 4

Shared mutations selected across experiments

| | mutS Strain | | | | | WT Strain, subinhibitory treatment | | | | | |
| --- | --- | --- | --- | --- | --- | --- | --- | --- | --- | --- | --- |
| | Biofilm | | | Planktonic | | Population 1 | | | Population 2 | | |
| Gene | Pop1 | Pop2 | Pop3 | Pop1 | Pop2 | Pop1 | S | W | Pop2 | S | Sc |
| orfN | — | — | — | (10)G→(9)G (138/1017 nt) | — | (10)G→(9)G (138/1017 nt) | (10)G→(9)G (138/1017 nt) | — | (10)G→(9)G (138/1017 nt) | (10)G→(9)G (138/1017 nt) | — |
| pmrB | V28L (59.7) L18P (17.3) A248T (11.1) | L180P (100) | L180P (49.3) V28A (18.8) D47G (15.8) F44L (8.5) L318P (7.1) | L18P (100) | L18P (31.0) V185A (20.5) L296P (15.6) F408P (13.5) | P169L (100) | P169L | P169L | G184D (100) | G184D | G184D |
| wspF | Q282* (87.7) | L20P (24.2) | L20P (47.0) | L222P (31.2) T274I (29.7) Q282* (14.3) | L51P (11.9) L199P (7.8) Q319 (6.6) G283D (6.4) G280D (5.3) S159L (5.3) Q299* (5.2) | — | — | S159L | — | — | — |

WLBU2 (e.g., SEQ ID NO: 1) is an engineered AMP derived from natural LL-37 peptide. Cationic peptide WLBU2 (SEQ ID NO: 1) has effectiveness against a range of bacterial species in multiple conditions and absence of clear genetic mechanisms for resistance. The experiments described herein provide support for the multiple mutation model and also showed that the pathway to resistance is plausible for mutator strains or ones already containing one or more contributing mutations.

When mutations are not a limiting factor, WGS of propagated populations evolving in the presence of an antibiotic defines a single new mutation, then that mutation causes the new resistant and heritable phenotype. When those mutations are found in parallel in independent propagated lines that were propagated under different conditions (for instance biofilm or planktonic) or even different subtle different strains, and they do not appear in the controls propagated in the absence of antibiotic, those mutations are causing the heritable resistant phenotype.

Parallel evolution of mutations in pmrB and orfN genes were detected across four independent lineages. PmrB forms part of two-component regulatory system that modifies the lipid-A composition including its negative charge, a mechanism that may be associated with cationic peptide resistance in several species. In combination with pmrB variants, mutations in orfN and wbpM were found in WLBU2 (SEQ ID NO: 1) resistant populations and clones. OrfN and wbpM form part of the operon that synthesizes the LPS O-antigen, and mutations in orfN may increase antibiotic resistance by reducing membrane permeability. Mutations in wspA, wspF, and yfiR that increase aggregation and/or biofilm production, likely through increased cyclic-di-GMP that in turn increases production of the cationic Pel polysaccharide. The role of this positively charged component of a biofilm matrix interacting with a peptide (e.g., WLBU2 (SEQ ID NO: 1)) provided insight in the defense mechanism. Mutations in the phosphodiesterase domain of morA were repeatedly selected in mutator populations with a probable similar effect on cyclic-di-GMP and Pel-mediated biofilm production. Aggregation by secretion of a biofilm polymer may be a mechanism of WLBU2 (SEQ ID NO: 1) resistance or tolerance.

Combining experimental evolution and whole population genome sequencing described herein showed that WLBU2 (SEQ ID NO: 1) needs at least two or more mutations that affect the outer membrane and/or aggregation for resistance to evolve. Further biochemical assays showed the actual role of each mutation in the resistance phenotype.

Additional exemplary data, exemplary procedural or other details supplementary to those set forth herein (such as source code, supplemental figures, and supplemental tables) from Santos-Lopez et al., "Experimental evolution to identify undescribed mechanisms of resistance to a novel cationic peptide antibiotic." *BioRxiv*, (doi:10.1101/2020.12.16.423161), specifically are incorporated herein by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A method of treating an infection caused by a bacteria selected from *Klebsiella pneumoniae, Acinetobacter baumannii, Pseudomonas aeruginosa* and *Escherichia coli*, the bacteria comprising a mutation in a pmrB gene, a wspF gene, or a combination thereof, or a hypermutator bacteria strain of the bacteria, in a subject, comprising:

obtaining a sample of the bacteria of the bacterial infection from the subject;

administering to the subject a formulation comprising an antimicrobial peptide or salt thereof in a therapeutically effective amount to treat the bacterial infection, wherein the antimicrobial peptide comprises SEQ ID NO: 1; and monitoring a bacterial species obtained from the patient at one or more times after administration of the formulation for development of one or more additional mutations in at least one gene affecting an outer membrane of the bacteria species and/or aggregation of the bacteria species, wherein:

one or more of the mutations is in the pmrB gene, wherein the pmrB gene encodes a histidine kinase, wherein the mutations in the pmrB gene occur in at least one codon of the pmrB gene, and wherein each of the one or more mutations occur in the histidine kinase at a position in SEQ ID NO: 29 individually selected from the group consisting of 18, 28, 44, 47, 180, 185, 248, 296, 318, 408, and equivalent positions thereof, and/or one or more of the mutations is in the wspF gene, wherein the wspF gene encodes a protein-glutamate methylesterase, wherein the at least one mutation in the wspF gene occurs in one or more codons of the wspF gene, and wherein each of the at least one mutation occurs in the protein-glutamate methylesterase at a position in SEQ ID NO: 31, or an equivalent position thereof.

2. The method of claim 1, further comprising before and/or during administering the formulation to the patient, determining if bacteria obtained from the patient comprises a mutation in at least one gene affecting an outer membrane of the bacteria species and/or aggregation of the bacteria species.

3. The method of claim 1, wherein if one or more mutations in at least one gene affecting an outer membrane of the bacteria species and/or aggregation of the bacteria species is present in the bacteria, the subject is administered a dose of the formulation comprising the antimicrobial peptide or salt thereof in amounts exceeding a minimum inhibitory concentration (MIC) for the bacterial species.

4. The method of claim 1, wherein if the bacterial species develops resistance to the formulation comprising the antimicrobial peptide or salt thereof, or develops one or more additional mutations in at least one gene affecting an outer membrane of the bacteria species and/or aggregation of the bacteria species, discontinuing administering of the formulation to the subject.

5. The method of claim 1, wherein one or more of the mutations is in the pmrB gene, wherein the pmrB gene encodes a histidine kinase, wherein the mutations in the pmrB gene occur in at least one codon of the pmrB gene, and wherein each of the one or more mutations occur in the histidine kinase at a position in SEQ ID NO: 29 individually selected from the group consisting of 18, 28, 44, 47, 180, 185, 248, 296, 318, 408, and equivalent positions thereof.

6. The method of claim 5, wherein one or more of the mutations in the pmrB gene includes one or more of: V28L, L18P, A248T, L180P, V28A, D47G, F44L, L318P, V185A, L296P, and F408P.

7. The method of claim 1, wherein one or more of the mutations is in the wspF gene, wherein the wspF gene encodes a protein-glutamate methylesterase, wherein the at least one mutation in the wspF gene occurs in one or more codons of the wspF gene, and wherein each of the at least one mutation occurs in the protein-glutamate methylesterase at a position in SEQ ID NO: 31, or an equivalent position thereof.

8. The method of claim 7, wherein one or more of the mutations in the wspF gene includes one or more of: L20P, L51P, S159L, L199P, L222P, T274I, G280D, and G283D.

9. The method of claim 1, wherein the bacterial species is a bacterial species with a higher mutation rate as compared to the bacterial species ancestor (non-mutator) strain.

10. The method of claim 1, further comprising determining that the bacterial species is resistant to Polymyxin B prior to administering the formulation comprising the antimicrobial peptide or salt thereof, wherein the bacterial species further comprises a mutation in a pmrABC operon gene.

11. The method of claim 1, wherein the formulation comprising the antimicrobial peptide or salt thereof reduces the level of bacteria that comprises the mutation in the pmrABC operon gene, relative to a wildtype pmrABC operon gene present in a wild type bacteria species, to an extent comparable to a reduction of a level of the bacteria that comprises the wildtype pmrABC operon gene by the formulation comprising the antimicrobial peptide or salt thereof, as determined by an in vitro assay.

12. A method of treating an infection caused by *Pseudomonas aeruginosa*, the bacteria comprising a mutation in a pmrB gene, a wspF gene, an orfN gene, or a combination thereof, or a hypermutator bacteria strain of the bacteria, in a subject, comprising:
obtaining a sample of the bacteria of the bacterial infection from the subject;
administering to the subject a formulation comprising an antimicrobial peptide or salt thereof in a therapeutically effective amount to treat the bacterial infection, wherein the antimicrobial peptide comprises SEQ ID NO: 1; and
monitoring a bacterial species obtained from the patient at one or more times after administration of the formulation for development of one or more additional mutations in at least one gene affecting an outer membrane of the bacteria species and/or aggregation of the bacteria species, wherein:
one or more of the mutations is in the pmrB gene, wherein the pmrB gene encodes a histidine kinase, wherein the mutations in the pmrB gene occur in at least one codon of the pmrB gene, and wherein each of the one or more mutations occur in the histidine kinase at a position in SEQ ID NO: 29 individually selected from the group consisting of 18, 28, 44, 47, 180, 185, 248, 296, 318, and 408,
one or more of the mutations is in the orfN gene, wherein the orfN gene encodes a putative group 4 glycosyl transferase, wherein the at least one mutation in the orfN gene is in at least one codon of the orfN gene, and wherein the at least one mutation occurs in the putative group 4 glycosyl transferase at position 10 in SEQ ID NO: 30, and/or
one or more of the mutations is in the wspF gene, wherein the wspF gene encodes a protein-glutamate methylesterase, wherein the at least one mutation in the wspF gene occurs in one or more codons of the wspF gene, and wherein each of the at least one mutation occurs in the protein-glutamate methylesterase at a position in SEQ ID NO: 31.

13. The method of claim 12, wherein one or more of the mutations is in the pmrB gene, wherein the pmrB gene encodes a histidine kinase, wherein the mutations in the pmrB gene occur in at least one codon of the pmrB gene, and wherein each of the one or more mutations occur in the histidine kinase at a position in SEQ ID NO: 29 individually selected from the group consisting of 18, 28, 44, 47, 180, 185, 248, 296, 318, and 408.

14. The method of claim 12, wherein one or more of the mutations in the pmrB gene includes one or more of: V28L, L18P, A248T, L180P, V28A, D47G, F44L, L318P, V185A, L296P, and F408P.

15. The method of claim 12, wherein one or more of the mutations is in the wspF gene, wherein the wspF gene encodes a protein-glutamate methylesterase, wherein the at least one mutation in the wspF gene occurs in one or more codons of the wspF gene, and wherein each of the at least one mutation occurs in the protein-glutamate methylesterase at a position in SEQ ID NO: 31.

16. The method of claim 15, wherein one or more of the mutations in the wspF gene includes one or more of: L20P, L51P, S159L, L199P, L222P, T274I, G280D, and G283D.

17. The method of claim 12, wherein one or more of the mutations is in the orfN gene, wherein the orfN gene encodes a putative group 4 glycosyl transferase, wherein the at least one mutation in the orfN gene is in at least one codon of the orfN gene, and wherein the at least one mutation occurs in the putative group 4 glycosyl transferase at position 10 in SEQ ID NO: 30.

18. The method of claim 12, wherein the mutation in the orfN gene results in at least two different changes in the glycosyl transferase, wherein one of the at least two mutations comprise (10) G to (9) G.

* * * * *